United States Patent
Trudeau et al.

(10) Patent No.: US 11,147,682 B2
(45) Date of Patent: Oct. 19, 2021

(54) INTERVERTEBRAL IMPLANTS, INSTRUMENTS, AND METHODS

(71) Applicant: Pioneer Surgical Technology, Inc., Marquette, MI (US)

(72) Inventors: Jeffrey L. Trudeau, Marquette, MI (US); Michael D. Kakuk, Skandia, MI (US); Stephen John Horvath, Leander, TX (US); Katie S. Barron, Negaunee, MI (US); Michael Sibley Carter, Austin, TX (US); Brent E. Skaw, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 16/124,935

(22) Filed: Sep. 7, 2018

(65) Prior Publication Data
US 2019/0076266 A1 Mar. 14, 2019

Related U.S. Application Data

(60) Provisional application No. 62/555,966, filed on Sep. 8, 2017.

(51) Int. Cl.
*A61F 2/44* (2006.01)
*A61F 2/28* (2006.01)
(Continued)

(52) U.S. Cl.
CPC .............. *A61F 2/4455* (2013.01); *A61F 2/28* (2013.01); *A61F 2/30965* (2013.01); *A61F 2/442* (2013.01); *A61F 2/447* (2013.01); *A61F 2/4611* (2013.01); *A61F 2/4603* (2013.01); *A61F 2002/2835* (2013.01);
(Continued)

(58) Field of Classification Search
CPC . A61F 2/4611; A61F 2/447; A61F 2002/4629
See application file for complete search history.

(56) References Cited

U.S. PATENT DOCUMENTS

| | | |
|---|---|---|
| 1,168,770 A | 1/1916 | Wagner |
| 1,816,446 A | 7/1931 | Stapf |

(Continued)

FOREIGN PATENT DOCUMENTS

| | | |
|---|---|---|
| AU | 2006200017 | 2/2006 |
| CA | 1146301 A | 5/1983 |

(Continued)

OTHER PUBLICATIONS

US 6,117,172 A, 09/2000, Ripamonti (withdrawn)
(Continued)

*Primary Examiner* — Ellen C Hammond
(74) *Attorney, Agent, or Firm* — Fitch, Even, Tabin & Flannery LLP

(57) ABSTRACT

In accordance with one aspect, a spinal implant for fusing vertebral bones is provided that includes a monolithic body for being inserted between bones. The body has a through opening of the body for receiving bone growth material and a wall of the body extending about the through opening. The wall includes nubs extending into the through opening that increase the surface area of the wall available for bone on-growth.

39 Claims, 38 Drawing Sheets

(51) Int. Cl.
*A61F 2/30* (2006.01)
*A61F 2/46* (2006.01)

(52) U.S. Cl.
CPC ............... *A61F 2002/3008* (2013.01); *A61F 2002/30011* (2013.01); *A61F 2002/3092* (2013.01); *A61F 2002/30148* (2013.01); *A61F 2002/30593* (2013.01); *A61F 2002/30807* (2013.01); *A61F 2002/30838* (2013.01); *A61F 2002/30843* (2013.01); *A61F 2002/30891* (2013.01); *A61F 2002/30904* (2013.01); *A61F 2002/30985* (2013.01); *A61F 2002/4622* (2013.01); *A61F 2002/4627* (2013.01); *A61F 2220/0025* (2013.01); *A61F 2310/00023* (2013.01)

(56) References Cited

U.S. PATENT DOCUMENTS

| | | |
|---|---|---|
| 3,196,463 A | 7/1965 | Farneth |
| 3,413,741 A | 12/1968 | Fagan et al. |
| 3,648,691 A | 3/1972 | Lumb |
| 3,707,107 A | 12/1972 | Bieri |
| 3,739,684 A | 6/1973 | Vitkevich |
| 3,867,728 A | 2/1975 | Stubstad et al. |
| 3,875,595 A | 4/1975 | Froning et al. |
| 3,969,773 A | 7/1976 | Menschik |
| 3,975,778 A | 8/1976 | Newton, III |
| 4,021,382 A | 5/1977 | Stoy |
| 4,081,402 A | 3/1978 | Levy |
| 4,147,764 A | 4/1979 | Levy |
| 4,309,777 A | 1/1982 | Patil |
| 4,349,921 A | 9/1982 | Kuntz |
| 4,374,523 A | 2/1983 | Yoon |
| 4,401,112 A | 8/1983 | Rezaian |
| 4,454,612 A | 6/1984 | McDaniel |
| 4,566,466 A | 1/1986 | Ripple |
| 4,569,338 A | 2/1986 | Edwards |
| 4,629,464 A | 12/1986 | Takata |
| 4,636,217 A | 1/1987 | Ogilvie |
| 4,650,490 A | 3/1987 | Figgie, III |
| 4,657,550 A | 4/1987 | Daher |
| 4,696,290 A | 9/1987 | Steffee |
| 4,714,469 A | 12/1987 | Kenna |
| 4,717,556 A | 1/1988 | Kawamura |
| 4,728,561 A | 3/1988 | Crocker |
| 4,759,766 A | 7/1988 | Buettner-Janz |
| 4,759,769 A | 7/1988 | Hedman |
| 4,798,585 A | 1/1989 | Inoue |
| 4,799,372 A | 1/1989 | Marcon |
| 4,800,874 A | 1/1989 | David |
| 4,834,757 A | 5/1989 | Brantigan |
| 4,863,476 A | 9/1989 | Shepperd |
| 4,863,477 A | 9/1989 | Monson |
| 4,865,603 A | 9/1989 | Noiles |
| 4,878,914 A | 11/1989 | Miwa |
| 4,878,915 A | 11/1989 | Brantigan |
| 4,899,761 A | 2/1990 | Brown |
| 4,917,704 A | 4/1990 | Frey |
| 4,932,969 A | 6/1990 | Frey |
| 4,932,975 A | 6/1990 | Main |
| 4,936,848 A | 6/1990 | Bagby |
| 4,946,378 A | 8/1990 | Hirayama |
| 4,997,432 A | 3/1991 | Keller |
| 5,002,576 A | 3/1991 | Fuhrmann |
| 5,011,495 A | 4/1991 | Hollinger |
| 5,034,011 A | 7/1991 | Howland |
| 5,035,716 A | 7/1991 | Downey |
| 5,047,055 A | 9/1991 | Bao |
| 5,059,193 A | 10/1991 | Kuslich |
| 5,071,437 A | 12/1991 | Steffee |
| 5,084,057 A | 1/1992 | Green |
| 5,108,399 A | 4/1992 | Eitenmuller |
| 5,108,438 A | 4/1992 | Stone |
| 5,123,926 A | 6/1992 | Pisharodi |
| 5,127,920 A | 7/1992 | MacArthur |
| 5,133,759 A | 7/1992 | Turner |
| 5,133,772 A | 7/1992 | Hack |
| 5,137,534 A | 8/1992 | Sumita |
| 5,147,404 A | 9/1992 | Downey |
| 5,152,791 A | 10/1992 | Hakamatsuka |
| 5,171,278 A | 12/1992 | Pisharodi |
| 5,171,281 A | 12/1992 | Parsons |
| 5,171,327 A | 12/1992 | Koch |
| 5,176,710 A | 1/1993 | Hahn |
| 5,185,177 A | 2/1993 | Kijima |
| 5,192,326 A | 3/1993 | Bao |
| 5,213,112 A | 5/1993 | Niwa |
| 5,258,031 A | 11/1993 | Salib |
| 5,258,043 A | 11/1993 | Stone |
| 5,269,809 A | 12/1993 | Hayhurst |
| 5,271,385 A | 12/1993 | Bailey |
| 5,273,742 A | 12/1993 | Gould |
| 5,275,600 A | 1/1994 | Allard |
| 5,300,073 A | 4/1994 | Ray |
| 5,306,307 A | 4/1994 | Senter |
| 5,306,308 A | 4/1994 | Gross |
| 5,306,309 A | 4/1994 | Wagner |
| 5,314,477 A | 5/1994 | Marnay |
| 5,320,625 A | 6/1994 | Bertin |
| 5,320,644 A | 6/1994 | Baumgartner |
| 5,322,675 A | 6/1994 | Hakamatsuka |
| 5,334,205 A | 8/1994 | Cain |
| 5,370,697 A | 12/1994 | Baumgartner |
| 5,401,269 A | 3/1995 | Buttner-Janz |
| 5,425,772 A | 6/1995 | Brantigan |
| 5,425,773 A | 6/1995 | Boyd |
| 5,443,512 A | 8/1995 | Parr |
| 5,443,514 A | 8/1995 | Steffee |
| 5,458,642 A | 10/1995 | Beer |
| 5,458,643 A | 10/1995 | Oka |
| 5,462,362 A | 10/1995 | Yuhta |
| 5,474,558 A | 12/1995 | Neubardt |
| 5,480,449 A | 1/1996 | Hamilton |
| 5,496,318 A | 3/1996 | Howland |
| 5,507,816 A | 4/1996 | Bullivant |
| 5,514,180 A | 5/1996 | Heggeness |
| 5,519,982 A | 5/1996 | Herber |
| 5,522,894 A | 6/1996 | Draenert |
| 5,522,899 A | 6/1996 | Michelson |
| 5,525,363 A | 6/1996 | Herber |
| 5,531,794 A | 7/1996 | Takagi |
| 5,534,028 A | 7/1996 | Bao |
| 5,542,949 A | 8/1996 | Yoon |
| 5,549,679 A | 8/1996 | Kuslich |
| 5,556,431 A | 9/1996 | Buttner-Janz |
| 5,556,433 A | 9/1996 | Gabriel |
| 5,562,736 A | 10/1996 | Ray |
| 5,562,738 A | 10/1996 | Boyd |
| 5,569,442 A | 10/1996 | Fulmer |
| 5,571,189 A | 11/1996 | Kuslich |
| 5,571,493 A | 11/1996 | Fulmer |
| 5,593,409 A | 1/1997 | Michelson |
| 5,595,563 A | 1/1997 | Moisdon |
| 5,597,379 A | 1/1997 | Haines |
| 5,609,635 A * | 3/1997 | Michelson .............. A61F 2/442 623/17.16 |
| 5,609,636 A | 3/1997 | Kohrs |
| 5,609,643 A | 3/1997 | Colleran |
| 5,614,205 A | 3/1997 | Usala |
| 5,643,264 A | 7/1997 | Sherman |
| 5,645,596 A | 7/1997 | Kim |
| 5,645,597 A | 7/1997 | Krapiva |
| 5,645,598 A | 7/1997 | Brosnahan, III |
| 5,645,599 A | 7/1997 | Samani |
| 5,653,762 A | 8/1997 | Pisharodi |
| 5,658,332 A | 8/1997 | Ducheyne |
| 5,658,336 A | 8/1997 | Pisharodi |
| 5,658,337 A | 8/1997 | Kohrs |
| 5,665,122 A | 9/1997 | Kambin |
| 5,669,909 A | 9/1997 | Zdeblick |
| 5,674,295 A | 10/1997 | Ray |
| 5,674,296 A | 10/1997 | Bryan |
| 5,676,701 A | 10/1997 | Yuan |

(56) References Cited

U.S. PATENT DOCUMENTS

| | | |
|---|---|---|
| 5,676,702 A | 10/1997 | Ratron |
| 5,676,976 A | 10/1997 | Lee |
| 5,681,316 A | 10/1997 | Deorio |
| 5,681,872 A | 10/1997 | Erbe |
| 5,683,465 A | 11/1997 | Shinn |
| 5,683,667 A | 11/1997 | Fulmer |
| 5,693,100 A | 12/1997 | Pisharodi |
| 5,702,450 A | 12/1997 | Bisserie |
| 5,702,451 A | 12/1997 | Biedermann |
| 5,713,899 A | 2/1998 | Marnay |
| 5,713,904 A | 2/1998 | Errico |
| 5,716,415 A | 2/1998 | Steffee |
| 5,716,416 A | 2/1998 | Lin |
| 5,728,762 A | 3/1998 | Reich |
| 5,755,797 A | 5/1998 | Baumgartner |
| 5,755,798 A | 5/1998 | Papavero |
| 5,766,252 A | 6/1998 | Henry |
| 5,772,661 A | 6/1998 | Michelson |
| 5,776,198 A | 7/1998 | Rabbe |
| 5,776,199 A | 7/1998 | Michelson |
| 5,782,832 A | 7/1998 | Larsen |
| 5,782,971 A | 7/1998 | Constantz |
| 5,783,217 A | 7/1998 | Lee |
| 5,797,909 A | 8/1998 | Michelson |
| 5,797,963 A | 8/1998 | McDevitt |
| 5,800,547 A | 9/1998 | Schaefer |
| 5,820,632 A | 10/1998 | Constantz |
| 5,824,093 A | 10/1998 | Ray |
| 5,824,094 A | 10/1998 | Serhan |
| 5,824,331 A | 10/1998 | Usala |
| 5,836,948 A | 11/1998 | Zucherman |
| 5,860,973 A | 1/1999 | Michelson |
| 5,860,977 A | 1/1999 | Zucherman |
| 5,860,980 A | 1/1999 | Axelson, Jr. |
| 5,865,845 A | 2/1999 | Thalgott |
| 5,865,846 A | 2/1999 | Bryan |
| 5,876,404 A | 3/1999 | Zucherman |
| 5,885,299 A | 3/1999 | Winslow |
| 5,888,223 A | 3/1999 | Bray, Jr. |
| 5,888,224 A | 3/1999 | Beckers |
| 5,888,226 A | 3/1999 | Rogozinski |
| 5,893,889 A | 4/1999 | Harrington |
| 5,893,890 A | 4/1999 | Pisharodi |
| 5,895,428 A | 4/1999 | Berry |
| 5,888,227 A | 5/1999 | Cottle |
| 5,899,941 A | 5/1999 | Nishijima |
| 5,914,356 A | 6/1999 | Erbe |
| 5,919,235 A | 7/1999 | Husson |
| 5,922,339 A | 7/1999 | Usala |
| 5,931,777 A | 8/1999 | Sava |
| 5,939,039 A | 8/1999 | Sapieszko |
| 5,964,807 A | 10/1999 | Gan |
| 5,969,020 A | 10/1999 | Shalaby |
| 5,972,031 A | 10/1999 | Biedermann |
| 5,976,186 A | 11/1999 | Bao |
| 5,980,572 A | 11/1999 | Kim |
| 5,984,967 A | 11/1999 | Zdeblick |
| 5,989,289 A | 11/1999 | Coates |
| 6,001,130 A | 12/1999 | Bryan |
| 6,004,326 A | 12/1999 | Castro |
| 6,013,591 A | 1/2000 | Ying |
| 6,019,793 A | 2/2000 | Perren |
| 6,022,376 A | 2/2000 | Assell |
| 6,022,377 A | 2/2000 | Nuelle |
| 6,025,538 A | 2/2000 | Yaccarino, III |
| 6,027,742 A | 2/2000 | Lee |
| 6,037,519 A | 3/2000 | McKay |
| 6,039,761 A | 3/2000 | Li |
| 6,039,762 A | 3/2000 | McKay |
| 6,039,763 A | 3/2000 | Shelokov |
| 6,042,582 A | 4/2000 | Ray |
| 6,048,342 A | 4/2000 | Zucherman |
| 6,053,916 A | 4/2000 | Moore |
| 6,063,088 A | 5/2000 | Winslow |
| 6,066,175 A | 5/2000 | Henderson |
| 6,068,630 A | 5/2000 | Zucherman |
| 6,068,974 A | 5/2000 | Klann |
| RE36,758 E | 6/2000 | Fitz |
| 6,074,390 A | 6/2000 | Zucherman |
| 6,080,155 A | 6/2000 | Michelson |
| 6,080,158 A | 6/2000 | Lin |
| 6,090,112 A | 7/2000 | Zucherman |
| 6,093,205 A | 7/2000 | McLeod |
| 6,093,207 A | 7/2000 | Pisharodi |
| 6,096,038 A | 8/2000 | Michelson |
| 6,096,039 A | 8/2000 | Stoltenberg |
| 6,110,210 A | 8/2000 | Norton |
| 6,113,639 A | 9/2000 | Ray |
| 6,117,456 A | 9/2000 | Lee |
| 6,127,597 A | 10/2000 | Beyar |
| 6,132,465 A | 10/2000 | Ray |
| 6,136,031 A | 10/2000 | Middleton |
| 6,139,548 A | 10/2000 | Errico |
| 6,139,579 A | 10/2000 | Steffee |
| 6,143,031 A | 11/2000 | Knothe |
| 6,143,033 A | 11/2000 | Paul |
| 6,146,421 A | 11/2000 | Gordon |
| 6,146,422 A | 11/2000 | Lawson |
| 6,149,652 A | 11/2000 | Zucherman |
| 6,149,688 A | 11/2000 | Brosnahan |
| 6,152,926 A | 11/2000 | Zucherman |
| RE37,005 E | 12/2000 | Michelson |
| 6,156,038 A | 12/2000 | Zucherman |
| 6,156,067 A | 12/2000 | Bryan |
| 6,162,252 A | 12/2000 | Kuras |
| 6,179,874 B1 | 1/2001 | Cauthen |
| 6,183,471 B1 | 2/2001 | Zucherman |
| 6,183,518 B1 | 2/2001 | Ross |
| 6,187,046 B1 | 2/2001 | Yamamoto |
| 6,187,048 B1 | 2/2001 | Milner |
| 6,190,387 B1 | 2/2001 | Zucherman |
| 6,190,414 B1 | 2/2001 | Young |
| 6,193,756 B1 | 2/2001 | Studer |
| 6,193,757 B1 | 2/2001 | Foley |
| 6,206,924 B1 | 3/2001 | Timm |
| 6,207,218 B1 | 3/2001 | Layrolle |
| 6,210,422 B1 | 4/2001 | Douglas |
| 6,210,442 B1 | 4/2001 | Wing |
| 6,214,368 B1 | 4/2001 | Lee |
| 6,224,607 B1 | 5/2001 | Michelson |
| 6,224,630 B1 | 5/2001 | Bao |
| 6,231,881 B1 | 5/2001 | Usala |
| 6,235,030 B1 | 5/2001 | Zucherman |
| 6,238,397 B1 | 5/2001 | Zucherman |
| 6,240,926 B1 | 6/2001 | ChinGan |
| 6,245,108 B1 | 6/2001 | Biscup |
| 6,251,140 B1 | 6/2001 | Marino |
| 6,261,587 B1 | 7/2001 | Usala |
| 6,264,695 B1 | 7/2001 | Stoy |
| 6,270,498 B1 | 8/2001 | Michelson |
| 6,270,977 B1 | 8/2001 | Klann |
| 6,277,149 B1 | 8/2001 | Boyle |
| 6,280,444 B1 | 8/2001 | Zucherman |
| 6,280,475 B1 | 8/2001 | Bao |
| 6,280,478 B1 | 8/2001 | Richter |
| 6,283,968 B1 | 9/2001 | Mehdizadeh |
| 6,283,998 B1 | 9/2001 | Eaton |
| 6,287,341 B1 | 9/2001 | Lee |
| 6,290,724 B1 | 9/2001 | Marino |
| 6,296,665 B1 | 10/2001 | Strnad |
| 6,302,913 B1 | 10/2001 | Ripamonti |
| 6,309,400 B2 | 10/2001 | Beaupre |
| 6,312,472 B1 | 11/2001 | Hall |
| 6,315,795 B1 | 11/2001 | Scarborough |
| 6,315,797 B1 | 11/2001 | Middleton |
| 6,315,994 B2 | 11/2001 | Usala |
| 6,332,882 B1 | 12/2001 | Zucherman |
| 6,332,883 B1 | 12/2001 | Zucherman |
| 6,344,061 B1 | 2/2002 | Leitao |
| 6,346,123 B1 | 2/2002 | McKay |
| 6,348,071 B1 | 2/2002 | Steffee |
| 6,350,462 B1 | 2/2002 | Hakamatsuka |
| 6,352,557 B1 | 3/2002 | Ferree |
| 6,352,707 B1 | 3/2002 | Usala |

(56) References Cited

U.S. PATENT DOCUMENTS

| | | |
|---|---|---|
| 6,364,883 B1 | 4/2002 | Santilli |
| 6,368,350 B1 | 4/2002 | Erickson |
| 6,371,987 B1 | 4/2002 | Weiland |
| 6,371,990 B1 | 4/2002 | Ferree |
| 6,375,682 B1 | 4/2002 | Fleischmann |
| 6,379,355 B1 | 4/2002 | Zucherman |
| 6,395,031 B1 | 5/2002 | Foley |
| 6,395,032 B1 | 5/2002 | Gauchet |
| 6,402,784 B1 | 6/2002 | Wardlaw |
| 6,402,785 B1 | 6/2002 | Zdeblick |
| 6,419,676 B1 | 7/2002 | Zucherman |
| 6,419,677 B2 | 7/2002 | Zucherman |
| 6,419,704 B1 | 7/2002 | Ferree |
| 6,428,544 B1 | 8/2002 | Ralph |
| 6,428,575 B2 | 8/2002 | Koo |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph |
| 6,436,140 B1 | 8/2002 | Liu |
| 6,436,141 B2 | 8/2002 | Castro |
| 6,436,142 B1 | 8/2002 | Paes |
| 6,436,146 B1 | 8/2002 | Hassler |
| 6,440,168 B1 | 8/2002 | Cauthen |
| 6,440,170 B1 | 8/2002 | Jackson |
| 6,441,073 B1 | 8/2002 | Tanaka |
| 6,451,019 B1 | 9/2002 | Zucherman |
| 6,451,020 B1 | 9/2002 | Zucherman |
| 6,454,806 B1 | 9/2002 | Cohen |
| 6,458,159 B1 | 10/2002 | Thalgott |
| 6,458,162 B1 | 10/2002 | Koblish |
| 6,478,796 B2 | 11/2002 | Zucherman |
| 6,478,801 B1 | 11/2002 | Ralph |
| 6,478,822 B1 | 11/2002 | Leroux |
| 6,478,823 B1 | 11/2002 | Michelson |
| 6,482,233 B1 | 11/2002 | Aebi |
| 6,488,716 B1 | 12/2002 | Huang |
| 6,500,132 B1 | 12/2002 | Li |
| 6,500,178 B2 | 12/2002 | Zucherman |
| 6,500,549 B1 | 12/2002 | Deppisch et al. |
| 6,503,279 B1 | 1/2003 | Webb |
| 6,508,839 B1 | 1/2003 | Lambrecht |
| 6,514,256 B2 | 2/2003 | Zucherman |
| 6,517,580 B1 | 2/2003 | Ramadan |
| 6,520,993 B2 | 2/2003 | James |
| 6,524,341 B2 | 2/2003 | Laeng |
| 6,527,803 B1 | 3/2003 | Crozet |
| 6,527,804 B1 | 3/2003 | Gauchet |
| 6,527,810 B2 | 3/2003 | Johnson |
| 6,530,955 B2 | 3/2003 | Boyle |
| 6,533,786 B1 | 3/2003 | Needham |
| 6,533,799 B1 | 3/2003 | Bouchier |
| 6,537,320 B1 | 3/2003 | Michelson |
| 6,540,785 B1 | 4/2003 | Gill |
| 6,547,823 B2 | 4/2003 | Scarborough |
| 6,562,047 B2 | 5/2003 | Ralph |
| 6,565,566 B1 | 5/2003 | Wagner |
| 6,569,396 B1 | 5/2003 | Yanagi |
| 6,575,975 B2 | 6/2003 | Brace |
| 6,579,318 B2 | 6/2003 | Varga |
| 6,579,320 B1 | 6/2003 | Gauchet |
| 6,579,321 B1 | 6/2003 | Gordon |
| 6,582,453 B1 | 6/2003 | Tran |
| 6,582,466 B1 | 6/2003 | Gauchet |
| 6,592,624 B1 | 7/2003 | Fraser |
| 6,602,291 B1 | 8/2003 | Ray |
| 6,607,559 B2 | 8/2003 | Ralph |
| 6,610,089 B1 | 8/2003 | Liu |
| 6,610,091 B1 | 8/2003 | Reiley |
| 6,610,093 B1 | 8/2003 | Pisharodi |
| 6,620,091 B1 | 8/2003 | Reiley |
| 6,626,944 B1 | 9/2003 | Taylor |
| 6,635,059 B2 | 10/2003 | Randall |
| 6,641,614 B1 | 11/2003 | Wagner |
| 6,648,903 B1 | 11/2003 | Pierson |
| 6,652,533 B2 | 11/2003 | Oneil |
| 6,669,697 B1 | 12/2003 | Pisharodi |
| 6,669,730 B2 | 12/2003 | Ralph |
| 6,673,113 B2 | 1/2004 | Ralph |
| 6,676,703 B2 | 1/2004 | Biscup |
| 6,679,915 B1 | 1/2004 | Cauthen |
| 6,682,562 B2 | 1/2004 | Viart |
| 6,689,165 B1 | 2/2004 | Jacob et al. |
| 6,699,246 B2 | 3/2004 | Zucherman |
| 6,699,247 B2 | 3/2004 | Zucherman |
| 6,713,079 B2 | 3/2004 | Usala |
| 6,719,794 B2 | 4/2004 | Gerber |
| 6,730,315 B2 | 5/2004 | Usala |
| 6,733,531 B1 | 5/2004 | Trieu |
| 6,733,535 B2 | 5/2004 | Michelson |
| 6,736,817 B2 | 5/2004 | Troxell |
| 6,743,257 B2 | 6/2004 | Castro |
| 6,746,484 B1 | 6/2004 | Liu |
| 6,758,849 B1 | 7/2004 | Michelson |
| 6,758,862 B2 | 7/2004 | Berry |
| 6,767,367 B1 | 7/2004 | Michelson |
| 6,770,074 B2 | 8/2004 | Michelson |
| 6,770,095 B2 | 8/2004 | Grinberg |
| 6,770,096 B2 | 8/2004 | Bolger |
| 6,776,860 B2 | 8/2004 | Arai |
| 6,783,550 B2 | 8/2004 | MacArthur |
| 6,790,455 B2 | 9/2004 | Chu |
| 6,793,678 B2 | 9/2004 | Hawkins |
| 6,796,983 B1 | 9/2004 | Zucherman |
| 6,824,565 B2 | 11/2004 | Muhanna |
| 6,827,740 B1 | 12/2004 | Michelson |
| 6,830,570 B1 | 12/2004 | Frey |
| 6,833,006 B2 | 12/2004 | Foley |
| 6,835,206 B2 | 12/2004 | Jackson |
| 6,840,961 B2 | 1/2005 | Tofighi |
| 6,841,255 B2 | 1/2005 | Deppisch et al. |
| 6,843,805 B2 | 1/2005 | Webb |
| 6,846,327 B2 | 1/2005 | Khandkar |
| 6,858,041 B2 | 2/2005 | Richter |
| 6,863,689 B2 | 3/2005 | Ralph |
| 6,872,208 B1 | 3/2005 | McBride |
| 6,887,272 B2 | 5/2005 | Shinomiya |
| 6,890,355 B2 | 5/2005 | Michelson |
| 6,893,464 B2 | 5/2005 | Kiester |
| 6,899,716 B2 | 5/2005 | Cragg |
| 6,905,512 B2 | 6/2005 | Paes |
| 6,923,810 B1 | 8/2005 | Michelson |
| 6,923,830 B2 | 8/2005 | Michelson |
| 6,926,737 B2 | 8/2005 | Jackson |
| 6,936,071 B1 | 8/2005 | Marnay |
| 6,942,670 B2 | 9/2005 | Heldreth |
| 6,942,698 B1 | 9/2005 | Jackson |
| 6,949,251 B2 | 9/2005 | Dalal |
| 6,951,561 B2 | 10/2005 | Warren |
| 6,964,687 B1 | 11/2005 | Bernard |
| 6,966,931 B2 | 11/2005 | Huang |
| 6,974,479 B2 | 12/2005 | Trieu |
| 6,974,480 B2 | 12/2005 | Messerli |
| 6,979,353 B2 | 12/2005 | Bresina |
| 6,981,975 B2 | 1/2006 | Michelson |
| 6,984,246 B2 | 1/2006 | Huang |
| 6,986,789 B2 | 1/2006 | Schultz |
| 6,987,136 B2 | 1/2006 | Erbe |
| 6,991,653 B2 | 1/2006 | White |
| 6,991,654 B2 | 1/2006 | Foley |
| 7,001,433 B2 | 2/2006 | Songer |
| 7,018,416 B2 | 3/2006 | Hanson |
| 7,033,393 B2 | 4/2006 | Gainor |
| 7,033,394 B2 | 4/2006 | Michelson |
| 7,041,137 B2 | 5/2006 | Fulton |
| 7,041,138 B2 | 5/2006 | Lange |
| 7,044,972 B2 | 5/2006 | Mathys, Jr. |
| 7,056,341 B2 | 6/2006 | Crozet |
| 7,060,073 B2 | 6/2006 | Frey |
| 7,063,725 B2 | 6/2006 | Foley |
| RE39,196 E | 7/2006 | Ying |

(56) References Cited

U.S. PATENT DOCUMENTS

| | | |
|---|---|---|
| 7,074,240 B2 | 7/2006 | Pisharodi |
| 7,083,749 B2 | 8/2006 | Lin |
| 7,087,540 B2 | 8/2006 | Heide |
| 7,101,375 B2 | 9/2006 | Zucherman |
| 7,118,598 B2 | 10/2006 | Michelson |
| 7,122,057 B2 | 10/2006 | Beam |
| 7,125,425 B2 | 10/2006 | Foley |
| 7,135,042 B2 | 11/2006 | Stoll |
| 7,137,997 B2 | 11/2006 | Paul |
| 7,141,068 B2 | 11/2006 | Ross |
| 7,156,874 B2 | 1/2007 | Paponneau |
| 7,156,876 B2 | 1/2007 | Moumene |
| 7,169,183 B2 | 1/2007 | Liu |
| 7,172,627 B2 | 2/2007 | Fiere et al. |
| 7,201,751 B2 | 4/2007 | Zucherman |
| 7,217,293 B2 | 5/2007 | Branch, Jr. |
| 7,223,289 B2 | 5/2007 | Trieu |
| 7,226,480 B2 | 6/2007 | Thalgott |
| 7,230,039 B2 | 6/2007 | Trieu |
| 7,235,079 B2 | 6/2007 | Jensen |
| 7,238,203 B2 | 7/2007 | Bagga |
| 7,261,505 B2 | 8/2007 | Ernst |
| 7,264,621 B2 | 9/2007 | Coates |
| D553,742 S | 10/2007 | Park |
| D553,743 S | 10/2007 | Park |
| D553,744 S | 10/2007 | Park |
| D553,745 S | 10/2007 | Park |
| 7,303,583 B1 | 12/2007 | Schar |
| 7,318,841 B2 | 1/2008 | Tofighi |
| 7,326,251 B2 | 2/2008 | McCombe |
| 7,338,525 B2 | 3/2008 | Ferree |
| 7,445,634 B2 | 11/2008 | Trieu |
| 7,445,637 B2 | 11/2008 | Taylor |
| 7,455,692 B2 | 11/2008 | Michelson |
| 7,479,160 B2 | 1/2009 | Branch |
| 7,500,978 B2 | 3/2009 | Gorensek |
| 7,527,803 B2 | 5/2009 | Park et al. |
| 7,618,458 B2 | 11/2009 | Biedermann |
| 7,622,129 B1 | 11/2009 | Haberstroh et al. |
| 7,641,690 B2 | 1/2010 | Abdou |
| 7,648,509 B2 | 1/2010 | Stark |
| 7,662,182 B2 | 2/2010 | Zubok |
| 7,662,186 B2 | 2/2010 | Bagga |
| 7,682,397 B2 | 3/2010 | Berry |
| 7,717,958 B2 | 5/2010 | Cragg |
| 7,763,078 B2 | 7/2010 | Peterman |
| RE41,584 E | 8/2010 | Ying |
| 7,776,095 B2 | 8/2010 | Peterman |
| 7,794,465 B2 | 9/2010 | Marik |
| 7,819,920 B2 | 10/2010 | Assaker |
| 7,824,427 B2 | 11/2010 | Perez-Cruet |
| 7,833,246 B2 | 11/2010 | Mitchell |
| 7,833,283 B2 | 11/2010 | Webster et al. |
| 7,837,732 B2 | 11/2010 | Zucherman |
| 7,842,071 B2 | 11/2010 | Hawkes |
| 7,846,210 B2 | 12/2010 | Perez-Cruet |
| 7,850,732 B2 | 12/2010 | Heinz |
| 7,850,736 B2 | 12/2010 | Heinz |
| 7,857,840 B2 | 12/2010 | Krebs |
| 7,875,080 B2 | 1/2011 | Puno |
| 7,879,104 B2 | 2/2011 | Dewey |
| 7,883,542 B2 | 2/2011 | Zipnick |
| 7,892,239 B2 | 2/2011 | Warnick |
| 7,901,458 B2 | 3/2011 | DeRidder |
| 7,909,859 B2 | 3/2011 | Mosca |
| 7,909,871 B2 | 3/2011 | Abdou |
| 7,918,876 B2 | 4/2011 | Mueller |
| 7,918,891 B1 | 4/2011 | Curran |
| 7,922,765 B2 | 4/2011 | Reiley |
| 7,938,834 B2 | 5/2011 | Roush |
| 7,951,203 B2 | 5/2011 | McCombe |
| 7,976,550 B2 | 7/2011 | Trudeau |
| 7,988,708 B2 | 8/2011 | Yeh |
| 7,988,734 B2 | 8/2011 | Peterman |
| 8,002,831 B2 | 8/2011 | Burd |
| 8,002,837 B2 | 8/2011 | Stream |
| 8,012,156 B2 | 9/2011 | MarquezAlvarez |
| 8,012,208 B2 | 9/2011 | Lechmann |
| 8,025,678 B2 | 9/2011 | Reynolds |
| 8,029,755 B2 | 10/2011 | Ahn |
| 8,038,678 B2 | 10/2011 | Schmieding |
| 8,043,293 B2 | 10/2011 | Warnick |
| 8,062,375 B2 | 11/2011 | Glerum |
| 8,083,799 B2 | 12/2011 | Baynham |
| 8,105,382 B2 | 1/2012 | Olmos |
| 8,118,872 B2 | 2/2012 | Trudeau |
| 8,128,856 B2 | 3/2012 | Chou |
| 8,133,232 B2 | 3/2012 | Levy |
| 8,137,402 B2 | 3/2012 | Eckman |
| 8,142,508 B1 | 3/2012 | Bruffey |
| 8,157,845 B2 | 4/2012 | Warnick |
| 8,163,026 B2 | 4/2012 | Gray |
| 8,172,905 B2 | 5/2012 | Baynham |
| 8,187,334 B2 | 5/2012 | Curran |
| 8,192,356 B2 | 6/2012 | Miles |
| 8,192,357 B2 | 6/2012 | Miles |
| 8,216,316 B2 | 7/2012 | Kirschman |
| 8,221,479 B2 | 7/2012 | Glazer |
| 8,241,359 B2 | 8/2012 | Davis |
| 8,241,360 B2 | 8/2012 | Bao |
| 8,246,655 B2 | 8/2012 | Jackson |
| 8,246,686 B1 | 8/2012 | Curran |
| 8,262,701 B2 | 9/2012 | Rathbun |
| 8,262,731 B2 | 9/2012 | Songer |
| 8,262,737 B2 | 9/2012 | Bagga |
| 8,303,660 B1 | 11/2012 | Abdou |
| 8,308,767 B2 | 11/2012 | Hochschuler |
| 8,308,805 B2 | 11/2012 | Lynn |
| 8,343,224 B2 | 1/2013 | Lynn |
| 8,361,156 B2 | 1/2013 | Curran |
| 8,372,084 B2 | 2/2013 | Pernsteiner |
| 8,388,684 B2 | 3/2013 | Bao |
| 8,409,213 B2 | 4/2013 | Trudeau |
| 8,409,290 B2 | 4/2013 | Zamani |
| 8,425,529 B2 | 4/2013 | Milz et al. |
| 8,425,559 B2 | 4/2013 | Tebbe |
| 8,425,610 B2 | 4/2013 | Guyer |
| 8,444,650 B2 | 5/2013 | Warnick |
| 8,449,583 B2 | 5/2013 | Krebs |
| 8,486,147 B2 | 7/2013 | deVilliers |
| 8,486,149 B2 | 7/2013 | Saidha |
| 8,540,769 B2 | 9/2013 | Janowski |
| 8,597,050 B2 | 12/2013 | Flaherty |
| 8,597,357 B2 | 12/2013 | Trudeau |
| 8,597,604 B2 | 12/2013 | Ahn |
| 8,603,141 B2 | 12/2013 | Hochschuler |
| 8,603,172 B2 | 12/2013 | Fuji |
| 8,609,122 B2 | 12/2013 | Lamberti |
| 8,617,247 B2 | 12/2013 | Lechmann |
| 8,641,764 B2 | 2/2014 | Gately |
| 8,663,331 B2 | 3/2014 | McClellan, III |
| 8,664,202 B2 | 3/2014 | Lamberti |
| 8,672,976 B2 | 3/2014 | Kilpela |
| 8,685,031 B2 | 4/2014 | Kleiner |
| 8,690,917 B2 | 4/2014 | Suh |
| 8,700,198 B2 | 4/2014 | Conway |
| 8,709,088 B2 | 4/2014 | Kleiner |
| 8,715,350 B2 | 5/2014 | Janowski |
| 8,734,521 B2 | 5/2014 | Freeman |
| 8,758,409 B2 | 6/2014 | Hochschuler |
| 8,858,637 B2 | 10/2014 | Milz |
| 8,870,957 B2 | 10/2014 | Vraney |
| 8,888,854 B2 | 11/2014 | Glerum |
| 8,906,028 B2 | 12/2014 | Kleiner |
| 8,940,317 B2 | 1/2015 | Lamberti |
| D723,682 S | 3/2015 | Kleiner |
| 9,072,609 B2 | 7/2015 | Kovarik |
| 9,132,021 B2 | 9/2015 | Mermuys |
| 9,233,011 B2 | 1/2016 | Trudeau |
| D750,249 S | 2/2016 | Grimberg |
| 9,358,122 B2 | 6/2016 | Soo |
| 9,387,092 B2 | 7/2016 | Mermuys |
| 9,408,717 B2 | 8/2016 | Perrow |
| 9,445,914 B2 | 9/2016 | Milz |

(56) References Cited

U.S. PATENT DOCUMENTS

| | | | |
|---|---|---|---|
| 9,545,269 B2 | 1/2017 | Kilpela | |
| 9,549,822 B2 | 1/2017 | Wimberley | |
| 9,561,961 B2 | 2/2017 | Capistron | |
| 9,687,359 B2 | 6/2017 | Perrow | |
| 9,693,872 B2 | 7/2017 | Trudeau | |
| 9,700,430 B2 | 7/2017 | Perrow | |
| 9,883,949 B2 | 2/2018 | Mermuys | |
| 10,105,240 B2 | 10/2018 | Defelice | |
| D833,012 S | 11/2018 | Jones et al. | |
| D833,611 S | 11/2018 | Jones et al. | |
| D833,612 S | 11/2018 | Jones et al. | |
| D835,279 S | 12/2018 | Jones et al. | |
| D835,788 S | 12/2018 | Jones et al. | |
| D840,036 S | 2/2019 | Jones et al. | |
| 2001/0010021 A1 | 7/2001 | Boyd | |
| 2001/0012938 A1 | 8/2001 | Zucherman | |
| 2001/0014826 A1 | 8/2001 | Biedermann | |
| 2001/0016733 A1 | 8/2001 | Frey | |
| 2001/0016772 A1 | 8/2001 | Lee | |
| 2001/0016773 A1 | 8/2001 | Serhan | |
| 2001/0016776 A1 | 8/2001 | Zuckerman | |
| 2001/0020476 A1 | 9/2001 | Gan | |
| 2001/0027343 A1 | 10/2001 | Keller | |
| 2001/0031965 A1 | 10/2001 | Zucherman | |
| 2001/0032019 A1 | 10/2001 | VanDyke | |
| 2001/0032020 A1 | 10/2001 | Besselink | |
| 2001/0047208 A1 | 11/2001 | Michelson | |
| 2001/0049560 A1 | 12/2001 | Paul | |
| 2001/0051829 A1 | 12/2001 | Middleton | |
| 2002/0013600 A1 | 1/2002 | Scribner | |
| 2002/0013624 A1 | 1/2002 | Michelson | |
| 2002/0022883 A1 | 2/2002 | Burg | |
| 2002/0022888 A1 | 2/2002 | Serhan | |
| 2002/0026244 A1 | 2/2002 | Trieu | |
| 2002/0029082 A1 | 3/2002 | Muhanna | |
| 2002/0029083 A1 | 3/2002 | Zuckerman | |
| 2002/0035400 A1 | 3/2002 | Bryan | |
| 2002/0045942 A1 | 4/2002 | Ham | |
| 2002/0045944 A1 | 4/2002 | Muhanna | |
| 2002/0049447 A1 | 4/2002 | Li | |
| 2002/0049498 A1 | 4/2002 | Yuksel | |
| 2002/0065560 A1 | 5/2002 | Varga | |
| 2002/0082608 A1 | 6/2002 | Reiley | |
| 2002/0082700 A1 | 6/2002 | Bianchi | |
| 2002/0082701 A1 | 6/2002 | Zdeblick | |
| 2002/0087212 A1 | 7/2002 | James | |
| 2002/0087480 A1 | 7/2002 | Sauriol | |
| 2002/0091390 A1 | 7/2002 | Michelson | |
| 2002/0099444 A1 | 7/2002 | Boyd | |
| 2002/0106393 A1 | 8/2002 | Bianchi | |
| 2002/0107571 A1 | 8/2002 | Foley | |
| 2002/0107572 A1 | 8/2002 | Foley | |
| 2002/0107573 A1 | 8/2002 | Steinberg | |
| 2002/0111683 A1 | 8/2002 | Ralph | |
| 2002/0111687 A1 | 8/2002 | Ralph | |
| 2002/0115742 A1 | 8/2002 | Trieu | |
| 2002/0120269 A1 | 8/2002 | Lange | |
| 2002/0120270 A1 | 8/2002 | Trieu | |
| 2002/0120334 A1 | 8/2002 | Crozet | |
| 2002/0120336 A1 | 8/2002 | Santilli | |
| 2002/0127720 A1 | 9/2002 | Erbe | |
| 2002/0143319 A1 | 10/2002 | Brock | |
| 2002/0143400 A1 | 10/2002 | Biscup | |
| 2002/0151894 A1 | 10/2002 | Melkent | |
| 2002/0151979 A1 | 10/2002 | Lambrecht | |
| 2002/0156528 A1 | 10/2002 | Gau | |
| 2002/0165550 A1 | 11/2002 | Frey | |
| 2002/0165612 A1 | 11/2002 | Gerber | |
| 2002/0165613 A1 | 11/2002 | Lin | |
| 2002/0165616 A1 | 11/2002 | Heide | |
| 2002/0177897 A1 | 11/2002 | Michelson | |
| 2003/0003127 A1 | 1/2003 | Brown | |
| 2003/0009226 A1 | 1/2003 | Graf | |
| 2003/0009227 A1 | 1/2003 | Lambrecht | |
| 2003/0014113 A1 | 1/2003 | Ralph | |
| 2003/0014115 A1 | 1/2003 | Ralph | |
| 2003/0023306 A1 | 1/2003 | Liu | |
| 2003/0023311 A1 | 1/2003 | Trieu | |
| 2003/0028197 A1 | 2/2003 | Hanson | |
| 2003/0028249 A1 | 2/2003 | Baccelli | |
| 2003/0028251 A1 | 2/2003 | Mathews | |
| 2003/0034329 A1 | 2/2003 | Chou | |
| 2003/0040796 A1 | 2/2003 | Ferree | |
| 2003/0040798 A1 | 2/2003 | Michelson | |
| 2003/0040799 A1 | 2/2003 | Boyd | |
| 2003/0040802 A1 | 2/2003 | Errico | |
| 2003/0045939 A1 | 3/2003 | Casutt | |
| 2003/0055427 A1 | 3/2003 | Graf | |
| 2003/0060891 A1 | 3/2003 | Shah | |
| 2003/0069586 A1 | 4/2003 | Errico | |
| 2003/0069642 A1 | 4/2003 | Ralph | |
| 2003/0069643 A1 | 4/2003 | Ralph | |
| 2003/0073998 A1 | 4/2003 | Pagliuca | |
| 2003/0074075 A1 | 4/2003 | Thomas | |
| 2003/0074076 A1 | 4/2003 | Ferree | |
| 2003/0078579 A1 | 4/2003 | Ferree | |
| 2003/0078590 A1 | 4/2003 | Errico | |
| 2003/0078662 A1 | 4/2003 | Ralph | |
| 2003/0083748 A1 | 5/2003 | Lee | |
| 2003/0093155 A1 | 5/2003 | Lambrecht | |
| 2003/0100950 A1 | 5/2003 | Moret | |
| 2003/0100951 A1 | 5/2003 | Serhan | |
| 2003/0120351 A1 | 6/2003 | Tofighi | |
| 2003/0130667 A1 | 7/2003 | Lin | |
| 2003/0130737 A1 | 7/2003 | McGahan | |
| 2003/0135275 A1 | 7/2003 | Garcia | |
| 2003/0135276 A1 | 7/2003 | Eckman | |
| 2003/0135277 A1 | 7/2003 | Bryan | |
| 2003/0135278 A1 | 7/2003 | Eckman | |
| 2003/0135279 A1 | 7/2003 | Michelson | |
| 2003/0139812 A1 | 7/2003 | Garcia | |
| 2003/0139813 A1 | 7/2003 | Messerli | |
| 2003/0139816 A1 | 7/2003 | Michelson | |
| 2003/0149438 A1 | 8/2003 | Nichols | |
| 2003/0149483 A1 | 8/2003 | Michelson | |
| 2003/0149484 A1 | 8/2003 | Michelson | |
| 2003/0176921 A1 | 9/2003 | Lawson | |
| 2003/0181981 A1 | 9/2003 | Lemaire | |
| 2003/0195514 A1 | 10/2003 | Trieu | |
| 2003/0195629 A1 | 10/2003 | Pafford | |
| 2003/0204260 A1 | 10/2003 | Ferree | |
| 2003/0204261 A1 | 10/2003 | Eisermann | |
| 2003/0204362 A1 | 10/2003 | Beresford | |
| 2003/0208203 A1 | 11/2003 | Lim | |
| 2003/0216810 A1 | 11/2003 | Ralph | |
| 2003/0220691 A1 | 11/2003 | Songer | |
| 2003/0229358 A1 | 12/2003 | Errico | |
| 2003/0233146 A1 | 12/2003 | Grinberg | |
| 2003/0236520 A1 | 12/2003 | Lim | |
| 2004/0002763 A1 | 1/2004 | Phillips | |
| 2004/0002764 A1 | 1/2004 | Gainor | |
| 2004/0006394 A1 | 1/2004 | Lipman | |
| 2004/0010316 A1 | 1/2004 | William | |
| 2004/0024462 A1 | 2/2004 | Ferree | |
| 2004/0024463 A1 | 2/2004 | Thomas | |
| 2004/0030390 A1 | 2/2004 | Ferree | |
| 2004/0030391 A1 | 2/2004 | Ferree | |
| 2004/0030392 A1 | 2/2004 | Lambrecht | |
| 2004/0034426 A1 | 2/2004 | Errico | |
| 2004/0038445 A1 | 2/2004 | Lowrey | |
| 2004/0044410 A1 | 3/2004 | Ferree | |
| 2004/0049280 A1 | 3/2004 | Cauthen | |
| 2004/0052829 A1 | 3/2004 | Shimp | |
| 2004/0068321 A1 | 4/2004 | Ferree | |
| 2004/0073315 A1 | 4/2004 | Justin et al. | |
| 2004/0082999 A1 | 4/2004 | Mathys | |
| 2004/0093082 A1 | 5/2004 | Ferree | |
| 2004/0093083 A1 | 5/2004 | Branch | |
| 2004/0093088 A1 | 5/2004 | Ralph | |
| 2004/0098129 A1 | 5/2004 | Lin | |
| 2004/0102846 A1 | 5/2004 | Keller | |
| 2004/0115172 A1 | 6/2004 | Bianchi | |
| 2004/0117018 A1 | 6/2004 | Michelson | |
| 2004/0117019 A1 | 6/2004 | Trieu | |

(56) References Cited

U.S. PATENT DOCUMENTS

| | | |
|---|---|---|
| 2004/0117022 A1 | 6/2004 | Marnay |
| 2004/0127990 A1 | 7/2004 | Bartish |
| 2004/0127993 A1 | 7/2004 | Kast |
| 2004/0127994 A1 | 7/2004 | Kast |
| 2004/0133132 A1 | 7/2004 | Chappuis |
| 2004/0133207 A1 | 7/2004 | Abdou |
| 2004/0133278 A1 | 7/2004 | Marino |
| 2004/0133280 A1 | 7/2004 | Trieu |
| 2004/0143331 A1 | 7/2004 | Errico |
| 2004/0143332 A1 | 7/2004 | Krueger |
| 2004/0148027 A1 | 7/2004 | Errico |
| 2004/0148028 A1 | 7/2004 | Ferree |
| 2004/0153065 A1 | 8/2004 | Lim |
| 2004/0153157 A1 | 8/2004 | Keller |
| 2004/0153158 A1 | 8/2004 | Errico |
| 2004/0153159 A1 | 8/2004 | Cauthen |
| 2004/0158328 A1 | 8/2004 | Eisermann |
| 2004/0162616 A1 | 8/2004 | Simonton |
| 2004/0162618 A1 | 8/2004 | Mujwid |
| 2004/0167520 A1 | 8/2004 | Zucherman |
| 2004/0167534 A1 | 8/2004 | Errico |
| 2004/0167536 A1 | 8/2004 | Errico |
| 2004/0167538 A1 | 8/2004 | Gerber |
| 2004/0167626 A1 | 8/2004 | Geremakis |
| 2004/0167628 A1 | 8/2004 | Foley |
| 2004/0167637 A1 | 8/2004 | Biscup |
| 2004/0176843 A1 | 9/2004 | Zubok |
| 2004/0176845 A1 | 9/2004 | Zubok |
| 2004/0176848 A1 | 9/2004 | Zubok |
| 2004/0176853 A1 | 9/2004 | Sennett |
| 2004/0181282 A1 | 9/2004 | Zucherman |
| 2004/0186573 A1 | 9/2004 | Ferree |
| 2004/0186577 A1 | 9/2004 | Ferree |
| 2004/0186579 A1 | 9/2004 | Callaway |
| 2004/0193272 A1 | 9/2004 | Zubok |
| 2004/0199251 A1 | 10/2004 | McCombe |
| 2004/0199252 A1 | 10/2004 | Sears |
| 2004/0199255 A1 | 10/2004 | Mathieu |
| 2004/0204760 A1 | 10/2004 | Fitz |
| 2004/0210226 A1 | 10/2004 | Trieu |
| 2004/0210312 A1 | 10/2004 | Neumann |
| 2004/0214326 A1 | 10/2004 | Cousins et al. |
| 2004/0220568 A1 | 11/2004 | Zucherman |
| 2004/0220670 A1 | 11/2004 | Eisermann |
| 2004/0225295 A1 | 11/2004 | Zubok |
| 2004/0243239 A1 | 12/2004 | Taylor |
| 2004/0243240 A1 | 12/2004 | Beaurain |
| 2004/0249471 A1 | 12/2004 | Bindseil |
| 2005/0004672 A1 | 1/2005 | Pafford |
| 2005/0010292 A1 | 1/2005 | Carrasco |
| 2005/0015150 A1 | 1/2005 | Lee |
| 2005/0015154 A1 | 1/2005 | Lindsey |
| 2005/0021030 A1 | 1/2005 | Pagliuca |
| 2005/0021042 A1 | 1/2005 | Marnay |
| 2005/0021143 A1 | 1/2005 | Keller |
| 2005/0021144 A1 | 1/2005 | Malberg |
| 2005/0021149 A1 | 1/2005 | Borruto |
| 2005/0027360 A1 | 2/2005 | Webb |
| 2005/0031704 A1 | 2/2005 | Ahn |
| 2005/0033305 A1 | 2/2005 | Schultz |
| 2005/0033437 A1 | 2/2005 | Bao |
| 2005/0033438 A1 | 2/2005 | Schultz |
| 2005/0038445 A1 | 2/2005 | Errico |
| 2005/0038515 A1 | 2/2005 | Kunzler |
| 2005/0038516 A1 | 2/2005 | Spoonamore |
| 2005/0043796 A1 | 2/2005 | Grant |
| 2005/0043798 A1 | 2/2005 | Eckman |
| 2005/0049589 A1 | 3/2005 | Jackson |
| 2005/0049590 A1 | 3/2005 | Alleyne |
| 2005/0049707 A1 | 3/2005 | Ferree |
| 2005/0055029 A1 | 3/2005 | Marik |
| 2005/0055097 A1 | 3/2005 | Grunberg |
| 2005/0060034 A1 | 3/2005 | Berry |
| 2005/0060035 A1 | 3/2005 | Errico |
| 2005/0065604 A1 | 3/2005 | Stoll |
| 2005/0070918 A1 | 3/2005 | Zwirnmann |
| 2005/0071005 A1 | 3/2005 | Carli |
| 2005/0071010 A1 | 3/2005 | Crozet |
| 2005/0071011 A1 | 3/2005 | Ralph |
| 2005/0071012 A1 | 3/2005 | Serhan |
| 2005/0080488 A1 | 4/2005 | Schultz |
| 2005/0085911 A1 | 4/2005 | Link |
| 2005/0085917 A1 | 4/2005 | Marnay |
| 2005/0096745 A1 | 5/2005 | Andre |
| 2005/0101955 A1 | 5/2005 | Zucherman |
| 2005/0107789 A1 | 5/2005 | Sweeney |
| 2005/0107881 A1 | 5/2005 | Alleyne |
| 2005/0113842 A1 | 5/2005 | Bertagnoli |
| 2005/0118230 A1 | 6/2005 | Hill |
| 2005/0119752 A1 | 6/2005 | Williams |
| 2005/0125062 A1 | 6/2005 | Biedermann |
| 2005/0125066 A1 | 6/2005 | McAfee |
| 2005/0131541 A1 | 6/2005 | Trieu |
| 2005/0143735 A1 | 6/2005 | Kyle |
| 2005/0143738 A1 | 6/2005 | Zucherman |
| 2005/0143820 A1 | 6/2005 | Zucherman |
| 2005/0143822 A1 | 6/2005 | Paul |
| 2005/0143824 A1 | 6/2005 | Richelsoph |
| 2005/0143826 A1 | 6/2005 | Zucherman |
| 2005/0149048 A1 | 7/2005 | Leport |
| 2005/0154463 A1 | 7/2005 | Trieu |
| 2005/0154464 A1 | 7/2005 | Humphreys |
| 2005/0154466 A1 | 7/2005 | Humphreys |
| 2005/0154468 A1 | 7/2005 | Rivin |
| 2005/0165398 A1 | 7/2005 | Reiley |
| 2005/0165485 A1 | 7/2005 | Trieu |
| 2005/0177237 A1 | 8/2005 | Shappley |
| 2005/0177238 A1 | 8/2005 | Khandkar |
| 2005/0177245 A1 | 8/2005 | Leatherbury |
| 2005/0182416 A1 | 8/2005 | Lim |
| 2005/0192670 A1 | 9/2005 | Zubok |
| 2005/0192671 A1 | 9/2005 | Bao |
| 2005/0196420 A1 | 9/2005 | Zucherman |
| 2005/0203512 A1 | 9/2005 | Hawkins |
| 2005/0203538 A1 | 9/2005 | Lo |
| 2005/0209603 A1 | 9/2005 | Zucherman |
| 2005/0209698 A1 | 9/2005 | Gordon |
| 2005/0216084 A1 | 9/2005 | Fleischmann |
| 2005/0216087 A1 | 9/2005 | Zucherman |
| 2005/0228383 A1 | 10/2005 | Zucherman |
| 2005/0228384 A1 | 10/2005 | Zucherman |
| 2005/0228498 A1 | 10/2005 | Andres |
| 2005/0228501 A1 | 10/2005 | Miller |
| 2005/0240182 A1 | 10/2005 | Zucherman |
| 2005/0245937 A1 | 11/2005 | Winslow |
| 2005/0251267 A1 | 11/2005 | Winterbottom |
| 2005/0256581 A1 | 11/2005 | Songer |
| 2005/0261768 A1 | 11/2005 | Trieu |
| 2005/0266581 A1 | 12/2005 | Droit |
| 2005/0267587 A1 | 12/2005 | Lin |
| 2005/0267588 A1 | 12/2005 | Lin |
| 2005/0267589 A1 | 12/2005 | Lin |
| 2005/0273166 A1 | 12/2005 | Sweeney |
| 2005/0278026 A1 | 12/2005 | Gordon |
| 2005/0281856 A1 | 12/2005 | McGlohorn |
| 2005/0283245 A1 | 12/2005 | Gordon et al. |
| 2006/0004447 A1 | 1/2006 | Mastrorio |
| 2006/0004453 A1 | 1/2006 | Bartish |
| 2006/0004454 A1 | 1/2006 | Ferree |
| 2006/0020341 A1 | 1/2006 | Schneid |
| 2006/0020342 A1 | 1/2006 | Ferree |
| 2006/0030860 A1 | 2/2006 | Peterman |
| 2006/0030943 A1 | 2/2006 | Peterman |
| 2006/0041314 A1 | 2/2006 | Millard |
| 2006/0041614 A1 | 2/2006 | Oe |
| 2006/0069436 A1 | 3/2006 | Sutton |
| 2006/0085076 A1 | 4/2006 | Krishna |
| 2006/0089646 A1 | 4/2006 | Bonutti |
| 2006/0089654 A1 | 4/2006 | Lins |
| 2006/0095043 A1 | 5/2006 | Martz |
| 2006/0095136 A1 | 5/2006 | McLuen |
| 2006/0116767 A1 | 6/2006 | Magerl |
| 2006/0129238 A1 | 6/2006 | Paltzer |
| 2006/0129244 A1 | 6/2006 | Ensign |

(56) References Cited

U.S. PATENT DOCUMENTS

| | | |
|---|---|---|
| 2006/0136062 A1 | 6/2006 | Dinello |
| 2006/0142858 A1 | 6/2006 | Colleran |
| 2006/0149258 A1 | 7/2006 | Sousa |
| 2006/0149388 A1 | 7/2006 | Smith |
| 2006/0155295 A1 | 7/2006 | Supper |
| 2006/0167549 A1 | 7/2006 | Mathys, Jr. |
| 2006/0178744 A1 | 8/2006 | De Villiers |
| 2006/0178745 A1 | 8/2006 | Bartish |
| 2006/0195103 A1 | 8/2006 | Padget |
| 2006/0195190 A1 | 8/2006 | Lechmann |
| 2006/0195191 A1 | 8/2006 | Sweeney |
| 2006/0212122 A1 | 9/2006 | Perera |
| 2006/0217807 A1 | 9/2006 | Peterman |
| 2006/0217812 A1 | 9/2006 | Lambrecht |
| 2006/0224159 A1 | 10/2006 | Anderson |
| 2006/0229623 A1 | 10/2006 | Bonutti |
| 2006/0229627 A1 | 10/2006 | Hunt |
| 2006/0235414 A1 | 10/2006 | Lim |
| 2006/0235426 A1 | 10/2006 | Lim et al. |
| 2006/0235521 A1 | 10/2006 | Zucherman |
| 2006/0235527 A1 | 10/2006 | Buettner-Janz |
| 2006/0235528 A1 | 10/2006 | Buettner-Janz |
| 2006/0235531 A1 | 10/2006 | Buettner-Janz |
| 2006/0241597 A1 | 10/2006 | Mitchell |
| 2006/0241614 A1 | 10/2006 | Bruneau |
| 2006/0241761 A1 | 10/2006 | Gately |
| 2006/0241770 A1 | 10/2006 | Rhoda |
| 2006/0247657 A1 | 11/2006 | Trieu |
| 2006/0247665 A1 | 11/2006 | Ferree |
| 2006/0247772 A1 | 11/2006 | McKay |
| 2006/0247776 A1 | 11/2006 | Kim |
| 2006/0247784 A1 | 11/2006 | Kim |
| 2006/0253121 A1 | 11/2006 | Gorensek |
| 2006/0253132 A1 | 11/2006 | Evans |
| 2006/0259037 A1 | 11/2006 | Hartmann |
| 2006/0271194 A1 | 11/2006 | Zucherman |
| 2006/0293662 A1 | 12/2006 | Boyer |
| 2006/0293663 A1 | 12/2006 | Walkenhorst |
| 2006/0293752 A1 | 12/2006 | Moumene |
| 2007/0027544 A1 | 2/2007 | McCord |
| 2007/0027547 A1 | 2/2007 | Rydell |
| 2007/0032568 A1 | 2/2007 | Lin |
| 2007/0055246 A1 | 3/2007 | Zucherman |
| 2007/0055275 A1 | 3/2007 | Schaller |
| 2007/0055376 A1 | 3/2007 | Michelson |
| 2007/0073398 A1 | 3/2007 | Fabian |
| 2007/0093838 A1 | 4/2007 | Khodadadyan-Klostermann |
| 2007/0093850 A1 | 4/2007 | Harris et al. |
| 2007/0100212 A1 | 5/2007 | Pimenta |
| 2007/0100348 A1 | 5/2007 | Cauthen |
| 2007/0100454 A1 | 5/2007 | Burgess |
| 2007/0100455 A1 | 5/2007 | Parsons |
| 2007/0118226 A1 | 5/2007 | Lambrecht |
| 2007/0142843 A1 | 6/2007 | Dye |
| 2007/0161992 A1 | 7/2007 | Kwak |
| 2007/0162001 A1 | 7/2007 | Chin |
| 2007/0162128 A1 | 7/2007 | Deridder |
| 2007/0162131 A1 | 7/2007 | Friedman |
| 2007/0162138 A1 | 7/2007 | Heinz |
| 2007/0191837 A1 | 8/2007 | Trieu |
| 2007/0191954 A1 | 8/2007 | Hansell |
| 2007/0191959 A1 | 8/2007 | Hartmann |
| 2007/0213461 A1 | 9/2007 | Hu |
| 2007/0213641 A1 | 9/2007 | Francis |
| 2007/0213732 A1 | 9/2007 | Khanna |
| 2007/0213826 A1 | 9/2007 | Smith |
| 2007/0225726 A1 | 9/2007 | Dye |
| 2007/0233076 A1 | 10/2007 | Trieu |
| 2007/0233143 A1 | 10/2007 | Josse |
| 2007/0233153 A1 | 10/2007 | Shipp |
| 2007/0270961 A1 | 11/2007 | Ferguson |
| 2007/0288005 A1 | 12/2007 | Arnin |
| 2007/0293948 A1 | 12/2007 | Bagga |
| 2007/0293949 A1 | 12/2007 | Salerni |
| 2008/0009880 A1 | 1/2008 | Warnick |
| 2008/0009945 A1 | 1/2008 | Pacheco |
| 2008/0015588 A1 | 1/2008 | Hawkes |
| 2008/0015597 A1 | 1/2008 | Whipple |
| 2008/0021454 A1 | 1/2008 | Chao |
| 2008/0021456 A1 | 1/2008 | Gupta |
| 2008/0065219 A1 | 3/2008 | Dye |
| 2008/0071372 A1 | 3/2008 | Butler |
| 2008/0077153 A1 | 3/2008 | Pernsteiner |
| 2008/0077241 A1 | 3/2008 | Nguyen |
| 2008/0091211 A1 | 4/2008 | Gately |
| 2008/0103598 A1 | 5/2008 | Trudeau |
| 2008/0109081 A1 | 5/2008 | Bao |
| 2008/0114367 A1 | 5/2008 | Meyer |
| 2008/0114456 A1 | 5/2008 | Dewey |
| 2008/0140082 A1 | 6/2008 | Erdem |
| 2008/0154377 A1* | 6/2008 | Voellmicke ............. A61F 2/447 623/17.16 |
| 2008/0177271 A1 | 7/2008 | Yeh |
| 2008/0183211 A1 | 7/2008 | Lamborne |
| 2008/0188897 A1 | 8/2008 | Krebs |
| 2008/0188940 A1 | 8/2008 | Cohen |
| 2008/0195209 A1 | 8/2008 | Garcia |
| 2008/0200985 A1 | 8/2008 | Robie |
| 2008/0208342 A1 | 8/2008 | Hanson |
| 2008/0221695 A1 | 9/2008 | Jacofsky |
| 2008/0234828 A1 | 9/2008 | Wagner |
| 2008/0243252 A1 | 10/2008 | Hansen |
| 2008/0288073 A1 | 11/2008 | Renganath |
| 2008/0288076 A1 | 11/2008 | Soo |
| 2008/0288081 A1 | 11/2008 | Scrafton |
| 2008/0306488 A1 | 12/2008 | Altarac |
| 2008/0306489 A1 | 12/2008 | Altarac |
| 2008/0306538 A1 | 12/2008 | Moore |
| 2008/0306596 A1 | 12/2008 | Jones |
| 2008/0306598 A1 | 12/2008 | Hansen |
| 2009/0024174 A1 | 1/2009 | Stark |
| 2009/0030519 A1 | 1/2009 | Falahee |
| 2009/0036927 A1 | 2/2009 | Vestgaarden |
| 2009/0043390 A1 | 2/2009 | Meisel |
| 2009/0054901 A1 | 2/2009 | Oh |
| 2009/0062917 A1 | 3/2009 | Foley |
| 2009/0099610 A1 | 4/2009 | Johnson |
| 2009/0099661 A1 | 4/2009 | Bhattacharya |
| 2009/0105824 A1 | 4/2009 | Jones |
| 2009/0105825 A1 | 4/2009 | Foreman |
| 2009/0131986 A1 | 5/2009 | Lee |
| 2009/0138053 A1 | 5/2009 | Assell |
| 2009/0164020 A1 | 6/2009 | Janowski |
| 2009/0164023 A1 | 6/2009 | Devine |
| 2009/0185904 A1 | 7/2009 | Landberg |
| 2009/0216238 A1 | 8/2009 | Stark |
| 2009/0228054 A1 | 9/2009 | Hoffman |
| 2009/0234395 A1 | 9/2009 | Hoffman |
| 2009/0240333 A1 | 9/2009 | Trudeau |
| 2009/0240336 A1 | 9/2009 | Vander |
| 2009/0248163 A1 | 10/2009 | King |
| 2009/0259261 A1 | 10/2009 | Reiley |
| 2009/0276049 A1 | 11/2009 | Weiland |
| 2009/0281580 A1 | 11/2009 | Emannuel |
| 2009/0287254 A1 | 11/2009 | Nayet |
| 2009/0299479 A1 | 12/2009 | Jones |
| 2010/0003102 A1 | 1/2010 | Nagaiwa |
| 2010/0010496 A1 | 1/2010 | Isaza |
| 2010/0016974 A1 | 1/2010 | Janowski |
| 2010/0070039 A1 | 3/2010 | Guyer |
| 2010/0076559 A1 | 3/2010 | Bagga |
| 2010/0106190 A1 | 4/2010 | Linares |
| 2010/0106200 A1 | 4/2010 | Stark |
| 2010/0131011 A1 | 5/2010 | Stark |
| 2010/0171306 A1 | 7/2010 | Gillot |
| 2010/0191337 A1 | 7/2010 | Zamani |
| 2010/0198267 A1 | 8/2010 | Vaidya |
| 2010/0204798 A1 | 8/2010 | Gerbec |
| 2010/0228296 A1 | 9/2010 | Vraney |
| 2010/0249797 A1 | 9/2010 | Trudeau |
| 2010/0268228 A1 | 10/2010 | Petersen |
| 2010/0280619 A1 | 11/2010 | Yuan |
| 2011/0040362 A1 | 2/2011 | Godara |
| 2011/0045087 A1 | 2/2011 | Kerr |

(56) References Cited

U.S. PATENT DOCUMENTS

| | | |
|---|---|---|
| 2011/0054373 A1 | 3/2011 | Reiley |
| 2011/0054621 A1 | 3/2011 | Lim |
| 2011/0087294 A1 | 4/2011 | Reiley |
| 2011/0087296 A1 | 4/2011 | Reiley |
| 2011/0093078 A1 | 4/2011 | Puno |
| 2011/0098816 A1 | 4/2011 | Jacob |
| 2011/0098817 A1 | 4/2011 | Eckhardt |
| 2011/0106163 A1 | 5/2011 | Hochschuler |
| 2011/0106259 A1 | 5/2011 | Lindenmann |
| 2011/0112642 A1 | 5/2011 | Tohmeh |
| 2011/0118785 A1 | 5/2011 | Reiley |
| 2011/0118790 A1 | 5/2011 | Reiley |
| 2011/0118841 A1 | 5/2011 | Reiley |
| 2011/0144752 A1 | 6/2011 | Defelice |
| 2011/0144766 A1 | 6/2011 | Kale |
| 2011/0160772 A1 | 6/2011 | Arcenio |
| 2011/0166602 A1 | 7/2011 | Malek |
| 2011/0172774 A1 | 7/2011 | Varela |
| 2011/0184472 A1 | 7/2011 | Niederberger |
| 2011/0208309 A1 | 8/2011 | Peterson |
| 2011/0230970 A1 | 9/2011 | Lynn |
| 2011/0245923 A1 | 10/2011 | Cobb |
| 2011/0251689 A1 | 10/2011 | Seifert |
| 2011/0264218 A1 | 10/2011 | Asaad |
| 2011/0270402 A1 | 11/2011 | Frey |
| 2011/0282453 A1 | 11/2011 | Greenhalgh |
| 2011/0282454 A1 | 11/2011 | Ullrich |
| 2011/0295372 A1 | 12/2011 | Peterman |
| 2011/0301710 A1 | 12/2011 | Mather |
| 2011/0307042 A1 | 12/2011 | Decarmine |
| 2011/0313531 A1 | 12/2011 | Lechmann |
| 2011/0319946 A1 | 12/2011 | Levy |
| 2011/0319998 A1 | 12/2011 | ONeil |
| 2011/0320000 A1 | 12/2011 | ONeil |
| 2012/0010715 A1 | 1/2012 | Spann |
| 2012/0010717 A1 | 1/2012 | Spann |
| 2012/0029641 A1 | 2/2012 | Curran |
| 2012/0035730 A1 | 2/2012 | Spann |
| 2012/0071984 A1 | 3/2012 | Michelson |
| 2012/0083885 A1 | 4/2012 | Thibodeau |
| 2012/0130494 A1 | 5/2012 | DeLurio |
| 2012/0158144 A1 | 6/2012 | Ullrich |
| 2012/0172934 A1 | 7/2012 | Fisher |
| 2012/0179261 A1 | 7/2012 | Soo |
| 2012/0185045 A1 | 7/2012 | Morris |
| 2012/0191191 A1 | 7/2012 | Trieu |
| 2012/0203344 A1 | 8/2012 | Trudeau |
| 2012/0232349 A1 | 9/2012 | Perrow |
| 2012/0232664 A1 | 9/2012 | Ulrich |
| 2012/0239150 A1 | 9/2012 | Ullrich |
| 2012/0239151 A1 | 9/2012 | Ulrich |
| 2012/0239152 A1 | 9/2012 | Ullrich |
| 2012/0239153 A1 | 9/2012 | Ullrich |
| 2012/0239154 A1 | 9/2012 | Ullrich |
| 2012/0245694 A1 | 9/2012 | Ullrich |
| 2012/0265306 A1 | 10/2012 | Trieu |
| 2012/0265307 A1 | 10/2012 | Guyer |
| 2012/0265311 A1 | 10/2012 | Mather |
| 2012/0277869 A1 | 11/2012 | Siccardi |
| 2012/0277870 A1 | 11/2012 | Wolters |
| 2012/0277876 A1 | 11/2012 | Ullrich |
| 2012/0283834 A1 | 11/2012 | Gottlieb |
| 2012/0283838 A1 | 11/2012 | Rhoda |
| 2012/0290091 A1 | 11/2012 | Kirschman |
| 2012/0303123 A1 | 11/2012 | Robie |
| 2012/0303127 A1 | 11/2012 | Ullrich |
| 2012/0303128 A1 | 11/2012 | Ullrich |
| 2012/0303129 A1 | 11/2012 | Bagga |
| 2012/0310287 A1 | 12/2012 | Bao |
| 2012/0310354 A1 | 12/2012 | Ullrich |
| 2012/0316650 A1 | 12/2012 | Ullrich |
| 2012/0316653 A1 | 12/2012 | Ullrich |
| 2013/0006363 A1 | 1/2013 | Ullrich |
| 2013/0018466 A1 | 1/2013 | Yu |
| 2013/0030534 A1 | 1/2013 | DeLurio |
| 2013/0204372 A1 | 8/2013 | Mohar |
| 2013/0217838 A1 | 8/2013 | Defelice |
| 2013/0282120 A1 | 10/2013 | Refai et al. |
| 2014/0172103 A1 | 6/2014 | O'Neil |
| 2014/0249631 A1 | 9/2014 | Weiman |
| 2014/0277434 A1 | 9/2014 | Weeber |
| 2014/0277487 A1 | 9/2014 | Davenport |
| 2015/0061195 A1 | 3/2015 | Defelice |
| 2015/0265414 A1* | 9/2015 | Mermuys .............. A61F 2/4611 623/17.16 |
| 2015/0274588 A1 | 10/2015 | Defelice |
| 2015/0328665 A1 | 11/2015 | Defelice |
| 2015/0351915 A1 | 12/2015 | Defelice |
| 2016/0051371 A1 | 2/2016 | Defelice |
| 2016/0106551 A1 | 4/2016 | Grimberg |
| 2016/0166284 A1 | 6/2016 | Hacking |
| 2016/0199193 A1 | 7/2016 | Willis |
| 2016/0213821 A1* | 7/2016 | Melkent .................. A61L 27/58 |
| 2016/0278934 A1 | 9/2016 | Mermuys |
| 2016/0338851 A1* | 11/2016 | Ashleigh ............... A61F 2/4611 |
| 2017/0000619 A1 | 1/2017 | Milz |
| 2017/0057015 A1 | 3/2017 | Defelice |
| 2017/0112549 A1 | 4/2017 | Kilpela |
| 2017/0156880 A1 | 6/2017 | Halverson |
| 2017/0239061 A1 | 8/2017 | Parry |
| 2017/0239066 A1* | 8/2017 | Walsh ..................... A61F 2/447 |
| 2017/0296354 A1 | 10/2017 | Trudeau |
| 2017/0304070 A1 | 10/2017 | Perrow |
| 2017/0312089 A1 | 11/2017 | Duarte |
| 2017/0319355 A1 | 11/2017 | Perrow |
| 2018/0071113 A1* | 3/2018 | Melkent ................. A61F 2/4455 |
| 2018/0104063 A1 | 4/2018 | Asaad |
| 2019/0358058 A1* | 11/2019 | Trieu ..................... A61F 2/4455 |
| 2019/0388232 A1* | 12/2019 | Purcell .................... A61F 2/447 |
| 2020/0237526 A1* | 7/2020 | Wilson ............... A61B 17/7059 |

FOREIGN PATENT DOCUMENTS

| | | |
|---|---|---|
| CA | 2395609 | 8/2001 |
| CA | 2482403 | 9/2003 |
| CA | 2548780 A1 | 7/2005 |
| CN | 1697633 | 11/2005 |
| DE | 9000094 U1 | 1/1991 |
| DE | 29612269 U1 | 9/1996 |
| DE | 19818956 A1 | 11/1998 |
| DE | 19738052 A1 | 3/1999 |
| DE | 29911422 U1 | 8/1999 |
| DE | 19816832 C1 | 1/2000 |
| DE | 10130825 | 3/2002 |
| DE | 10309702 | 9/2004 |
| DE | 202005005405 | 6/2005 |
| EP | 0042271 A1 | 12/1981 |
| EP | 0179695 | 4/1986 |
| EP | 0346129 A1 | 12/1989 |
| EP | 0760687 A1 | 3/1997 |
| EP | 0773008 A1 | 5/1997 |
| EP | 0834295 A1 | 4/1998 |
| EP | 0919209 A1 | 6/1999 |
| EP | 1104665 A1 | 6/2001 |
| EP | 1132061 A2 | 9/2001 |
| EP | 1138285 | 10/2001 |
| EP | 1205160 | 5/2002 |
| EP | 1212992 A2 | 6/2002 |
| EP | 1346695 A1 | 9/2003 |
| EP | 1698305 | 9/2006 |
| EP | 2085056 | 8/2009 |
| EP | 2623069 A1 | 8/2013 |
| EP | 2349107 | 12/2016 |
| EP | 2273952 | 2/2018 |
| FR | 2372622 | 6/1978 |
| FR | 2703580 A1 | 10/1994 |
| FR | 2723841 | 3/1996 |
| FR | 2732841 | 10/1996 |
| FR | 2754170 A1 | 4/1998 |
| FR | 2787014 | 6/2000 |
| FR | 2797179 | 2/2001 |
| FR | 2799116 | 4/2001 |
| FR | 2801782 A1 | 6/2001 |
| FR | 2805985 | 9/2001 |

(56) References Cited

FOREIGN PATENT DOCUMENTS

| | | |
|---|---|---|
| FR | 2824261 A1 | 11/2002 |
| FR | 2827157 | 1/2003 |
| FR | 2841124 A1 | 12/2003 |
| JP | 63300758 A2 | 12/1988 |
| JP | 1308557 A2 | 12/1989 |
| JP | 02111358 | 4/1990 |
| JP | 2215461 A2 | 8/1990 |
| JP | 2224659 A2 | 9/1990 |
| JP | 2224660 A2 | 9/1990 |
| JP | 03275055 A | 12/1991 |
| JP | 03275056 A | 12/1991 |
| JP | 04303444 A | 10/1992 |
| JP | 05277141 A | 10/1993 |
| JP | 06285099 | 10/1994 |
| JP | H0731673 A | 2/1995 |
| JP | 08098850 A | 4/1996 |
| JP | 08098851 A2 | 4/1996 |
| JP | 11009618 A | 1/1999 |
| JP | 11137585 A | 5/1999 |
| JP | 2000210316 | 8/2000 |
| JP | 2001054564 A | 2/2001 |
| JP | 2003180814 A | 7/2003 |
| JP | 2008284348 A | 11/2008 |
| WO | 9000037 A1 | 1/1990 |
| WO | 9011740 | 10/1990 |
| WO | 9100713 A1 | 1/1991 |
| WO | 9105521 | 5/1991 |
| WO | 9116867 | 11/1991 |
| WO | 9316664 | 9/1993 |
| WO | 9428824 A2 | 12/1994 |
| WO | 9500082 | 1/1995 |
| WO | 9512369 A1 | 5/1995 |
| WO | 9601598 | 1/1996 |
| WO | 9611642 | 4/1996 |
| WO | 9627339 | 9/1996 |
| WO | 9717285 A1 | 5/1997 |
| WO | 9805274 | 2/1998 |
| WO | 9819617 | 5/1998 |
| WO | 9855053 | 12/1998 |
| WO | 9911203 | 3/1999 |
| WO | 9920208 A1 | 4/1999 |
| WO | 9922675 | 5/1999 |
| WO | 9930651 | 6/1999 |
| WO | 0013619 A1 | 3/2000 |
| WO | 0038574 | 7/2000 |
| WO | 0042953 | 7/2000 |
| WO | 0049977 A1 | 8/2000 |
| WO | 0059412 | 10/2000 |
| WO | 200066011 | 11/2000 |
| WO | 0132100 | 5/2001 |
| WO | 0137728 | 5/2001 |
| WO | 0115638 A1 | 8/2001 |
| WO | 0158369 A1 | 8/2001 |
| WO | 0168003 | 9/2001 |
| WO | 0195818 A1 | 12/2001 |
| WO | 0209626 | 2/2002 |
| WO | 200238086 | 5/2002 |
| WO | 02087480 | 11/2002 |
| WO | 03005887 | 1/2003 |
| WO | 03011343 A1 | 2/2003 |
| WO | 03030956 A2 | 4/2003 |
| WO | 03035129 | 5/2003 |
| WO | 03099171 A1 | 12/2003 |
| WO | 03099172 | 12/2003 |
| WO | 2004000177 A1 | 12/2003 |
| WO | 2005009298 | 2/2005 |
| WO | 2005041818 | 5/2005 |
| WO | 2005051240 | 6/2005 |
| WO | 2005055869 | 6/2005 |
| WO | 2005071190 A2 | 8/2005 |
| WO | 2005077307 | 8/2005 |
| WO | 2005086776 | 9/2005 |
| WO | 2005092208 A1 | 10/2005 |
| WO | 2005102226 A1 | 11/2005 |
| WO | 2005115261 A1 | 12/2005 |
| WO | 2006016384 A1 | 2/2006 |
| WO | 2006022644 A1 | 3/2006 |
| WO | 2006064356 | 6/2006 |
| WO | 2006102428 | 9/2006 |
| WO | 2007015028 | 2/2007 |
| WO | 2007016801 | 2/2007 |
| WO | 2007087535 | 8/2007 |
| WO | 2007121457 A1 | 10/2007 |
| WO | 2008034135 | 3/2008 |
| WO | 2008034140 | 3/2008 |
| WO | 2008098054 | 8/2008 |
| WO | 2008140551 A2 | 11/2008 |
| WO | 2009029074 A1 | 3/2009 |
| WO | 2009040840 A1 | 4/2009 |
| WO | 201003898 | 6/2010 |
| WO | 2010065015 A1 | 6/2010 |
| WO | 2011014135 A2 | 2/2011 |
| WO | 2011056172 | 5/2011 |
| WO | 2011097905 | 8/2011 |
| WO | 2012008279 | 1/2012 |
| WO | 2012010327 | 1/2012 |
| WO | 201103777 | 6/2012 |
| WO | 2013008111 | 1/2013 |

OTHER PUBLICATIONS

U.S. Appl. No. 29/621,557, filed Oct. 9, 2017, Trudeau Jeffrey L.
U.S. Appl. No. 62/555,966, filed Sep. 8, 2017, Trudeau.
Bao, Qi-Bin and Yuan, Hansen A., "Artificial Disc Technology", Neurosurg. Focus, vol. 9, No. 4, Oct. 2000, 7 pp.
Charite Artificial Disc Product Catalog, DePuy Spine, Inc., Dec. 2004, 17 pp.
Depuy Spine, Inc., Charite Artificial Disc Centreline TDR Instrumentation, Surgical Technique, Dec. 2004, 21 pp.
Feder, Barnaby J., "When F.D.A. Says Yes, but Insurers Say No", The New York Times, Jul. 6, 2005, 2 pp.
Invitation to Pay Additional Fees dated Nov. 8, 2018, in corresponding PCT/US2018/050001, 2 pages.
Medtronic Sofamor Danek, Union/Union L, Anterior & Lateral Impacted Fusion Devices, Clear Choice of Stabilization, 2001, (25 pages).
Millsaps, Bridget Butler, "3D Printed Spinal Implants: RTI Surgical Granted Exclusive License to OPM OsteoFab Technology Platform", 3Dprint.com, <https://3dprint.com/119715/rti-opm-spinal-implants/>, published Feb. 15, 2016, accessed Jul. 28, 2017, 11 pages.
Park et al, Kambin's Triangle Approach of Lumbar Transforaminal Epidural Injection with Spinal Stenosis, Dec. 30, 2011 (10 pages).
RTI Surgical, RTI Surgical Announces Agreement With Oxford performance materials, dated Feb. 11, 2016, 2 pages, accessed on Dec. 27, 2017 at the following website: https://www.businesswire.com/news/home/20160211006300/en/RTI-Surgical%C2%AE-Announces-Agreement-Oxford-Performance-Materials.
Zdeblick, T. et al, Cervical Interbody Fusion Cages, An Animal Model With and Without Bone Morphogenetic Protein, Spine, 1998, vol. 23, No. 7, 9 pp.
Zdeblick, Thomas, MD; Ghanayem, Alexander, MD; Rapoff, Andrew, MS; Swain, Carol, MS; Bassett, Tim, MD; Cooke, Mary, MS; Markel, Mark, DVM. Cervical Interbody Fusion Cages: An Animal Model With and Without Bone Morphogenetic Protein. Spine, vol. 23, No. 7., 1998. Lippincott Williams & Wilkins; Hagerstown, MD, USA. 8 pages.
Restriction Requirement dated Mar. 31, 2020, in corresponding Design U.S. Appl. No. 29/621,557 (5 pages).
PCT Search Report and Written Opinion from International Patent Application No. PCT/US2018/050001 dated Jan. 22, 2019; 22 pages.
Wang M, Bhardwaj B, Webster T; Antibacterial properties of PEKK for orthopedic applications. Int'l Journal of Nanomedicine. 2017: 12 6471-6476, published Sep. 5, 2017. (6 pages).
ProSpace Interbody System: Product Brochure, Aesculap Implant Systems, LLC, 2014, pp. 1-4 (4 pages).

(56) References Cited

OTHER PUBLICATIONS

Forza PTC Spacer System: Posterior & Transforaminal Lumbar Interbody Fusion, Orthofix Holdings, Inc., copyright Apr. 2020, describing implant publicly available before Sep. 8, 2017 (8 pages).
Ttitanium® PL Posterior Lumbar Cage: Surgical Technique, Stryker, 2018, pp. 1-32 (32 pages).
Endoskeleton® TT/TO: Posterior Interbody Fusion Device for the Lumbar Spine, Titan Spine, 2011 (2 pages).
A Revolution in Interbody Fusion: Cervical Interbody Fusion Device, Valeo II® C, CTL Amedica Corporation, copyright 2019, describing implant publicly available before Sep. 8, 2017 (2 pages).
A Revolution in Interbody Fusion: Transforaminal Lumbar Interbody Fusion Device, Valeo II® TL, CTL Amedica Corporation, copyright 2019, describing implant publicly available before Sep. 8, 2017 (2 pages).
Partial European Search Report and Written Opinion dated Apr. 22, 2021, in corresponding European Application No. 18853354.1 (20 pages).
Extended European Search Report and Written Opinion dated Sep. 6, 2021, in corresponding European Application No. 18853354.1 (20 pages).

\* cited by examiner

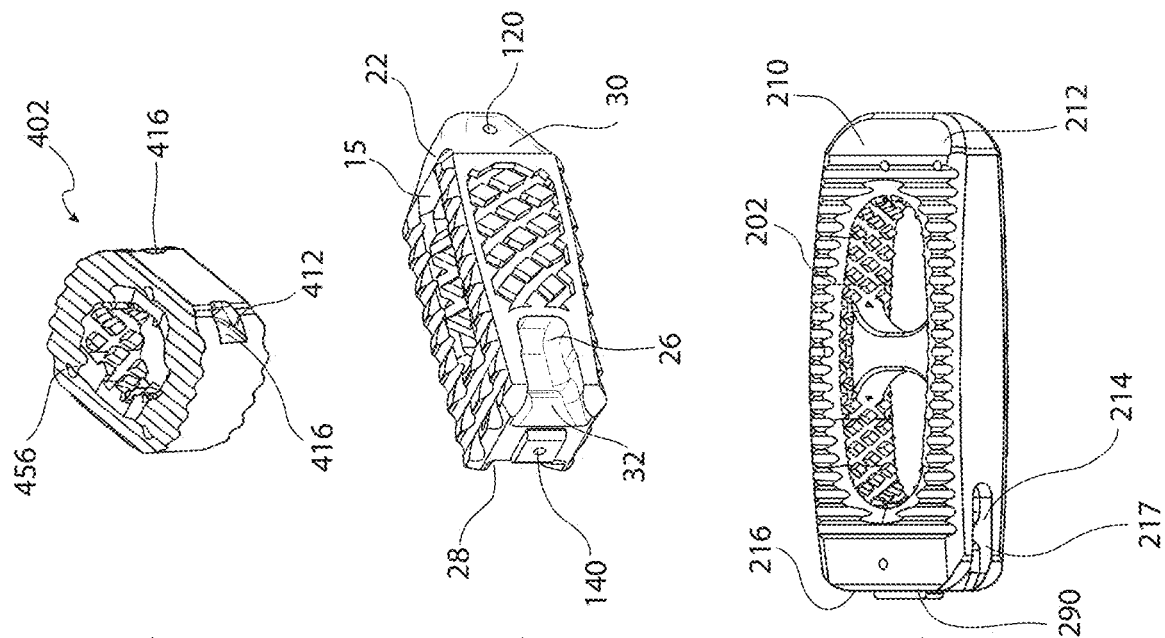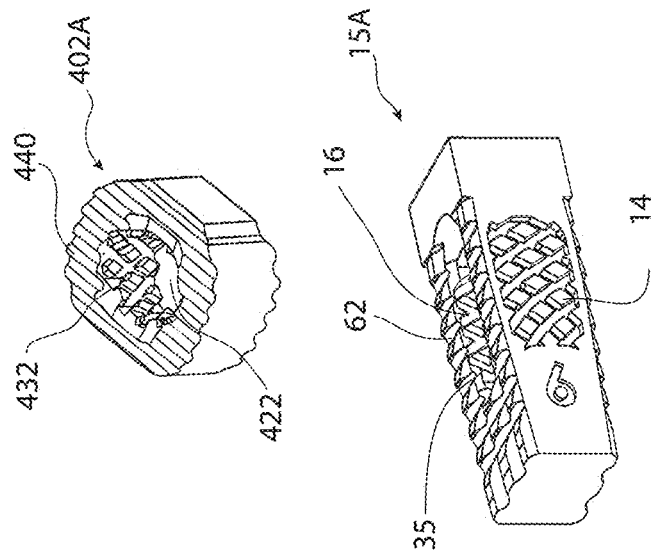

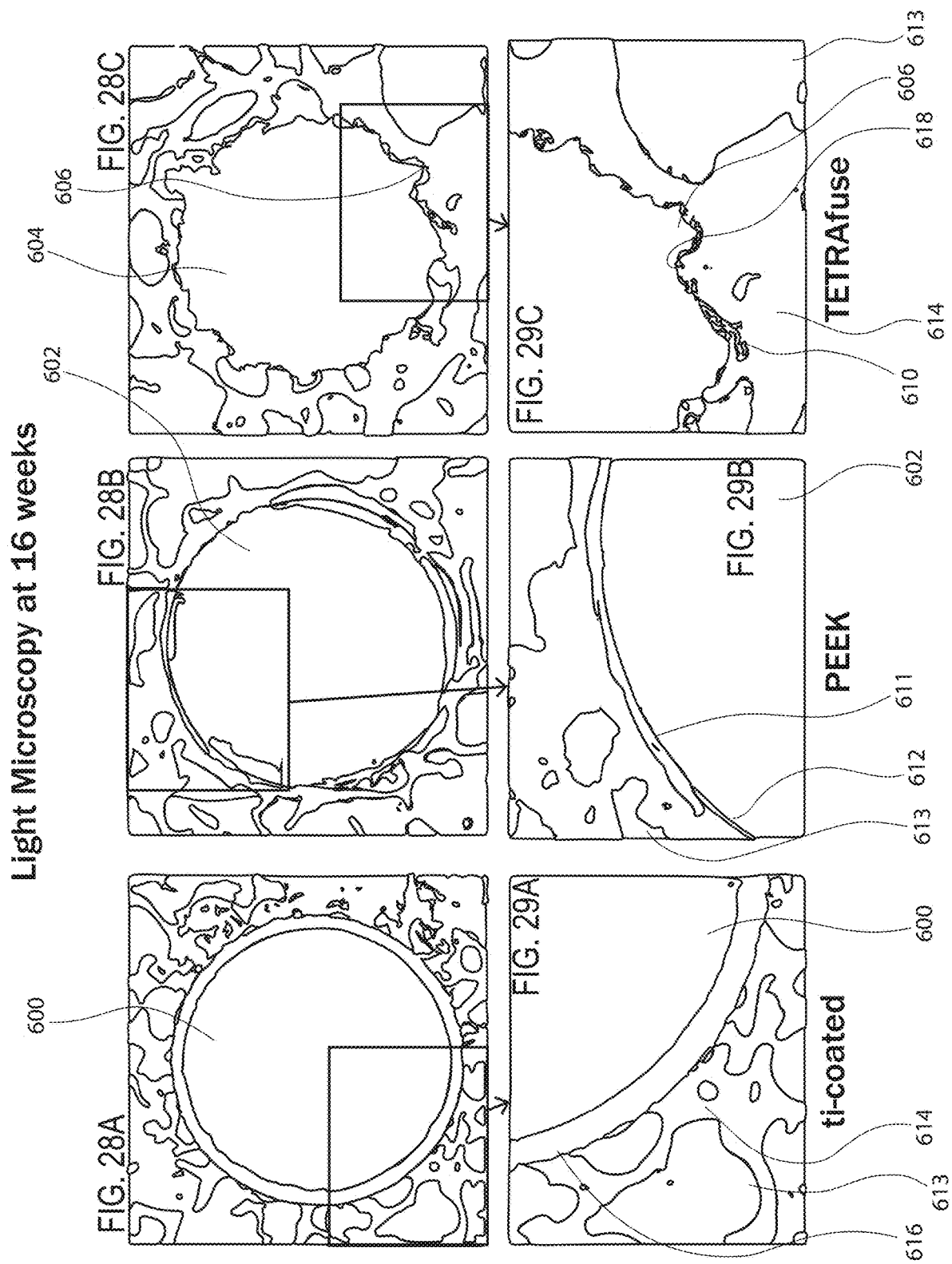

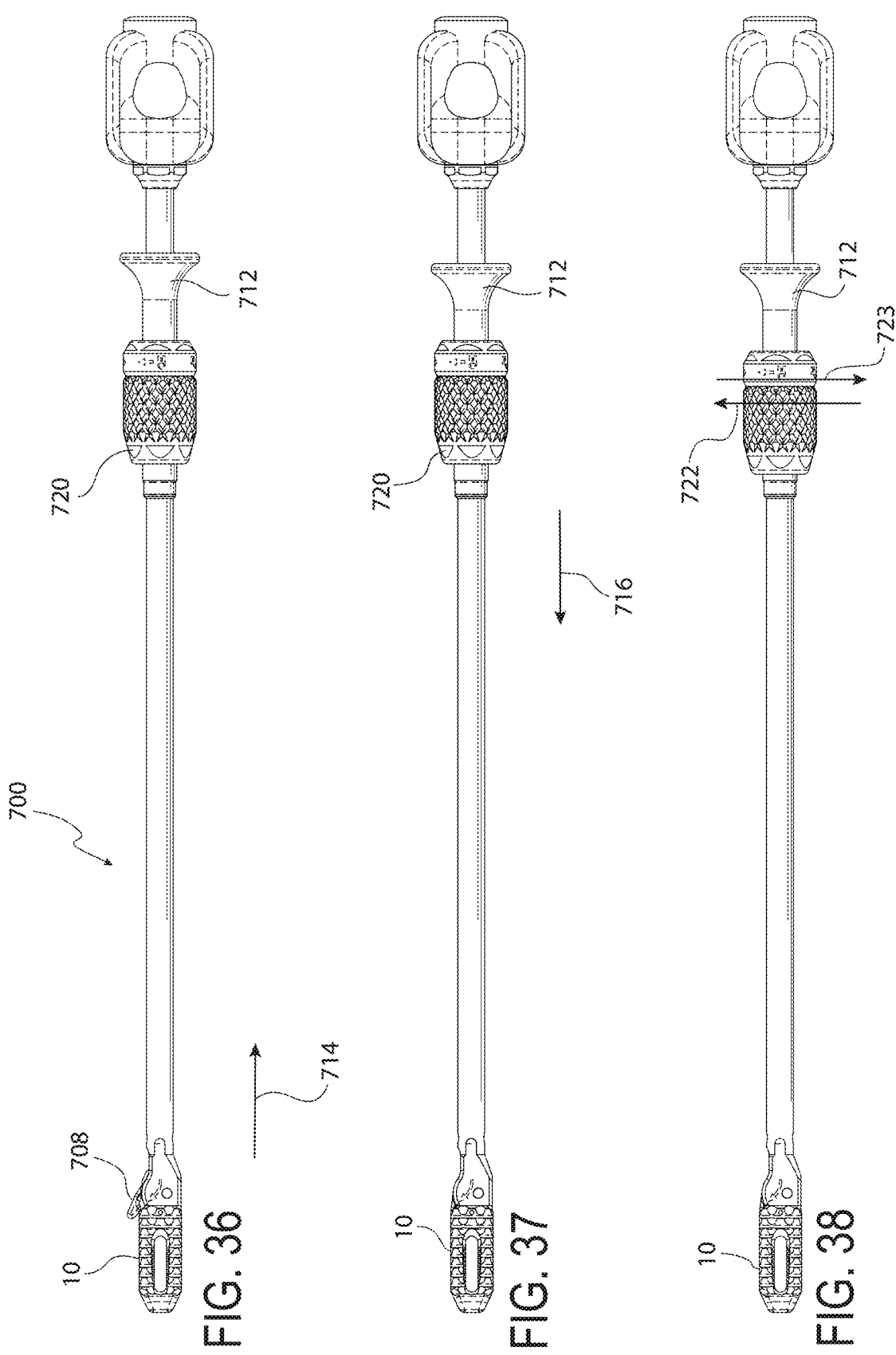

INTERVERTEBRAL IMPLANTS, INSTRUMENTS, AND METHODS

CROSS-REFERENCE TO RELATED APPLICATION

This application claims the benefit of U.S. Provisional Patent App. No. 62/555,966, filed Sep. 8, 2017, which is hereby incorporated by reference herein in its entirety.

FIELD

This disclosure relates generally to implantable medical devices and, more specifically, to implantable devices for intervertebral fusion and/or immobilization.

BACKGROUND

Many people develop back pain during their lifetimes due to injury, disease, or genetic defect. One source for back pain is if an intervertebral disc of a patient bulges outward from between the associated vertebrae. The bulging disc may impinge on the nerves of the spine and cause pain. To address this situation, a surgeon may trim the disc bulge or remove the disc entirely. The surgeon may then insert one or more implants to support and separate the vertebrae.

One type of implant used to support and separate vertebrae are interbody fusion devices ("IBDs"). IBDs often have a body with a large throughbore in which bone growth material can be packed to encourage bony ingrowth from the vertebrae and into the throughbore. One type of IBD is made of polyetheretherketone (PEEK). Although PEEK implants are radiolucent and do not obstruct x-ray viewing of the surgical site post-surgery, PEEK implants have been found to exhibit minimal amounts of bone growth onto the PEEK implant. PEEK IBDs may have a series of ridges in the throughbore that each extend continuously around the throughbore. These continuous ridges retain the bone growth material in the throughbore. The ridges extended continuously around the throughbore to maximize purchase with the bone growth material.

Another type of IBD is made of titanium-coated PEEK. The titanium coating has a roughened outer surface and encourages bone growth onto the implant. However, the titanium coating is radio-opaque and obstructs x-ray viewing of the surgical site post-surgery.

SUMMARY

In accordance with one aspect of the present disclosure, a spinal implant is provided for fusing vertebral bones. The spinal implant includes a monolithic body for being inserted between bones, a through opening of the body for receiving bone growth material, and a wall of the body extending about the through opening. The spinal implant further includes nubs of the wall extending into the through opening that increase the surface area of the wall available for bone on-growth. The increased surface area provides more area for bone to bond with the implant which increases the strength of the implant-vertebrae construct. The nubs of the wall also help retain the bone growth material within the through opening of the body which makes the implant easier to advance into the intervertebral space.

In one form, the monolithic body includes polyetherketoneketone (PEKK) and is fabricated using selective laser sintering. Fabricating the body by selective laser sintering PEKK produces rough surfaces of the body including surfaces of the nubs. For example, the rough surfaces of the body may have nanostructures that resemble peaks and valleys between the peaks, with an average peak-to-valley distance of approximately 125-129 nanometers and an average peak-to-peak distance of approximately 265-282 nanometers. It has been discovered that the combination of the increased surface area of the nubs and the roughness of the surfaces of the nubs encourages significant bone fusion interaction within the through opening of the body. Further, because the body is made from PEKK, the body is radiolucent to x-rays and permits a surgeon to view the surgical site post-surgery without obstruction by the implant body. This is an improvement over prior titanium-coated PEEK implants that are radio-opaque and obstruct viewing of the surgical site with x-rays. In this manner, the PEKK implant body provides both significant bone on-growth and a radiolucent implant for improving x-ray observation of the implant post-surgery.

In another aspect, an implant is provided for being inserted into an intervertebral space to stabilize vertebrae. The implant includes a monolithic body having a through opening for receiving bone growth material and an annular wall extending about the through opening. The annular wall is free of through apertures in communication with the through opening. In one embodiment, the monolithic body is made of PEKK and is fabricated using selective laser sintering. Although PEKK has a relatively high strength, PEKK becomes more brittle at narrow thicknesses. The absence of through apertures strengthens the annular wall of the body so that the annular wall can resist loading from the vertebrae after implantation, even at thin wall thickness such as 0.06 inches.

The body also includes an attachment member outward of the annular wall and recesses extending along opposite sides of the attachment member. The recesses are configured to receive clamping arms of an inserter tool. Because the inserter tool engages the implant by engaging the clamping arms with the attachment member, loading applied to the inserter tool such as by the surgeon moving the inserter tool in lateral directions is applied to the implant along opposite sides of the attachment member. Using opposite sides of the attachment member to receive loading from the inserter tool more evenly distributes loading from the inserter tool to the implant and minimizes stress concentrations on the implant due to the engagement with the clamping arms.

A spinal implant is also provided that includes a polymer body fabricated using additive manufacturing. The body has unmachined, irregular surfaces due to the body being fabricated by additive manufacturing. The irregular surfaces actively participate in bone on-growth which improves the strength of the engagement between the implant and bones. The body also includes a machined attachment portion for interfacing with an inserter tool. By machining the body, tight tolerances can be achieved for the attachment portion. The attachment portion has a surface roughness that is less rough than a surface roughness of the unmachined, irregular surfaces of the body. In this manner, the implant has both unmachined, irregular surfaces to encourage bone on-growth and a machined attachment portion with a reduced surface roughness that provides the high accuracy machined structures necessary to properly engage the inserter tool. In one embodiment, the plastic body is made of PEKK and is fabricated using selective laser sintering.

In accordance with another aspect of the present disclosure, a spinal implant system is provided that includes a spinal implant and an inserter tool. The spinal implant has a leading end portion, a trailing end portion, and a longitudinal axis extending therebetween. The tailing end portion includes an attachment member, and the attachment member has a boss extending axially outward from a trailing end surface of the attachment member. The inserter tool includes arms having a release configuration that permits the arms to be positioned on opposite sides of the attachment member and a gripping configuration wherein the arms clamp the attachment member therebetween. The inserter tool also includes a socket configured to engage the boss of the attachment member and increase the axial length of the engagement between the inserter tool and the implant. By increasing this axial length, the forces applied by the surgeon to the inserter tool as the surgeon manipulates the inserter tool (e.g., in the cephalad/caudal directions) is applied to the implant over a longer axial extent which more evenly distributes the forces and strengthens the connection between the implant and the inserter tool.

The present disclosure also provides a method of producing a spinal implant. The method includes fabricating a body of the spinal implant made of a polymer material using an additive manufacturing process. The body includes irregular outer surfaces having a first surface roughness produced by the additive manufacturing process. The method further includes machining the fabricated body to form an attachment portion of the body for interfacing with an inserter tool. The attachment portion has a second surface roughness that is less rough than the first surface roughness of the irregular outer surfaces of the body. The irregular outer surfaces of the fabricated body actively participate in bone on-growth which improves the strength of the engagement between the implant and bones. Further, by machining the fabricated body, tight tolerances can be achieved for the attachment portion. The method thereby provides a spinal implant having rougher irregular outer surfaces to encourage bone on-growth and a smoother attachment portion for precise engagement with an inserter tool.

In accordance with another aspect, a marker pin is provided for a spinal implant. The marker pin includes a body of a radiopaque material and a leading end portion of the body sized to fit into an opening of a body of a spinal implant. The body further includes an interference portion radially enlarged relative to the leading end portion and configured to engage the spinal implant body at a plurality of circumferentially spaced locations about the opening and retain the marker pin in the opening of the spinal implant body. Because the interference portion engages the spinal implant body at circumferentially spaced locations, there are undeformed portions of the spinal implant body separating localized deformations caused by the interference portion. This permits the marker pin to deform less of the material of the spinal implant body around the opening and makes the implant stronger.

BRIEF DESCRIPTION OF THE DRAWINGS

FIGS. 20, 21, and 22 are perspective views of bodies of implants fabricated by selective laser sintering PEKK and the bodies after the bodies have been machined;

FIG. 28A, 28B, 28C, 29A, 29B, 29C are cross-sectional pictures of pins similar to the pins of FIG. 26 in bone showing the most pronounced bone attachment to the pin implant formed by selective laser sintering PEKK;

FIG. 36 is a top plan view of the inserter tool of FIG. 31 and the implant of FIG. 2 showing the adjustment knob in a release position and the lock knob in an unlocked position;

FIG. 37 is a top plan view similar to FIG. 36 showing the adjustment knob in a gripping position and the lock knob in an unlocked position;

FIG. 38 is a view similar to FIG. 37 showing the lock knob turned to a locked position;

DETAILED DESCRIPTION

Figure 1:
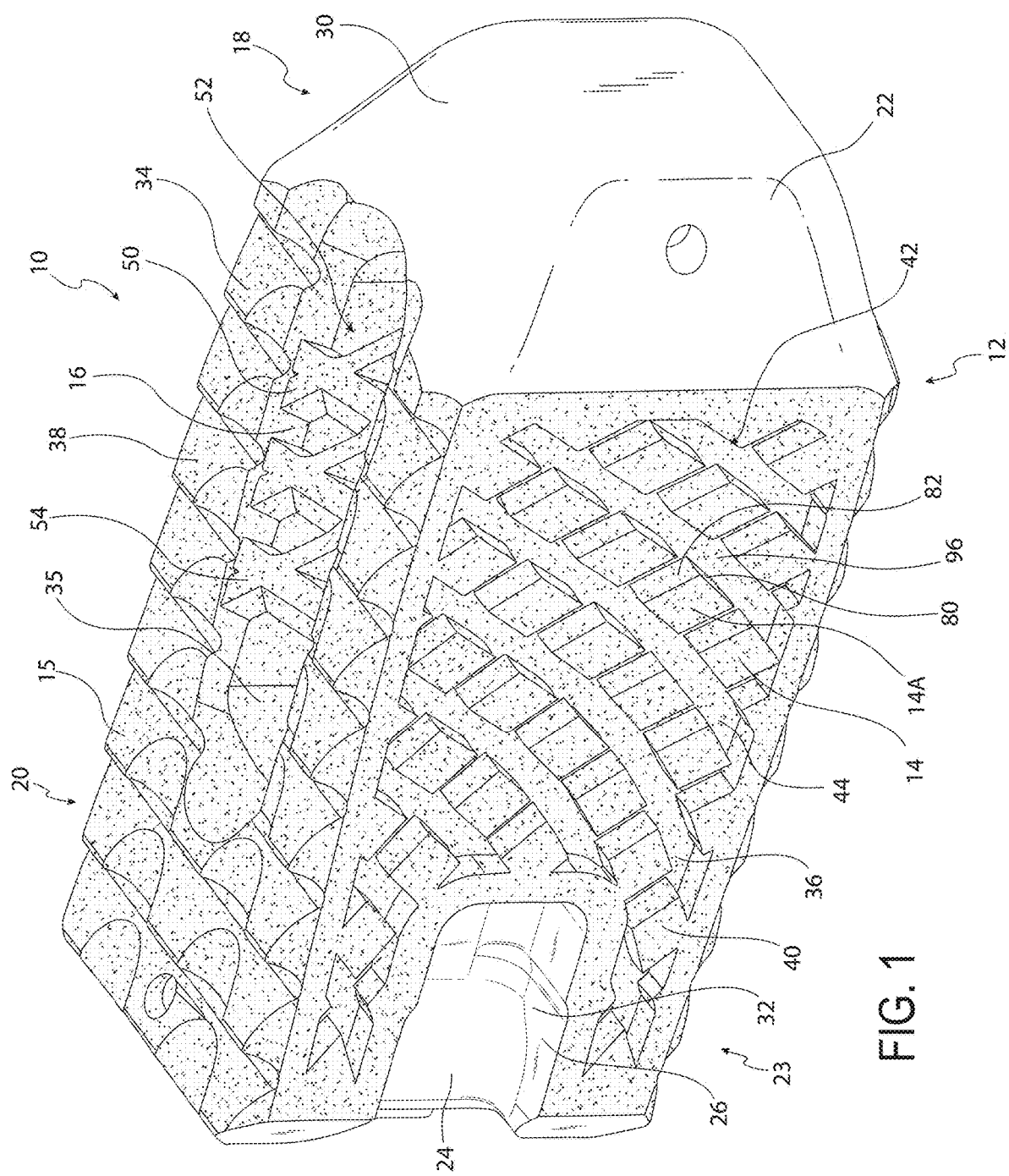
FIG. 1 is a perspective view of an implant showing rough, irregular surfaces of the implant formed by fabricating the implant by selective laser sintering PEKK and smoother surfaces of the implant formed by machining portions of the body.

With reference to FIG. 1, an implant 10 is provided for stabilizing vertebrae. The implant 10 has a body 15 that may be made of a plastic, such as polyetherketoneketone (PEKK), and may be fabricated using a 3D printing or additive manufacturing process, such as selective laser sintering. The fabrication of the implant 10 by selective laser sintering PEKK creates rough surfaces 12 of the body 15 due to the granule powder size and resolution of the selective laser sintering process. The rough surface texture of the rough surfaces 12 is indicated by stippling in the drawings. The rough surfaces 12 have nanostructures that resemble peaks and valleys between the peaks, with an average peak-to-valley distance of approximately 125-129 nanometers and an average peak-to-peak distance of approximately 265-282 nanometers. These parameters were measured using an XE7 atomic force microscope having a non-contact cantilever probe (from Park Systems of South Korea) with a force constant of 42 N/m, a scan size of 1×1 micrometer, and a scan frequency of 0.5 Hz.

The rough surface also includes micro-size pores having an average pore diameter in the range of approximately 500 micrometers to approximately 600 micrometers, such as approximately 530 micrometers. Further, the implant 10 has nubs 14 and 16 that are macro-size structures which increase the surface area of the surfaces 12 of the implant 10. The combination of the rough exterior surfaces 12 and the nubs 14, 16 results in deeper implant osseointegration than if the implant were made of PEEK or titanium plasma coated PEEK, as discussed in greater detail below. In other words, the rough exterior surfaces 12 and nubs 14, 16 allow more bone cells to attach to more of the implant 10.

The implant body 15 has a leading end portion 18 and a trailing end portion 20. The leading end portion 18 includes a tapered nose 22 and the trailing end portion 20 includes an attachment portion 23 including an attachment member 24 and recesses 26, 28. The body 15 may be machined after being fabricated to create the features of the nose 22, attachment member 24, and recesses 26, 28 in the body 15. The term machined is intended to mean that the implant is secured and a moving cutting member is brought into contact with the implant to remove material from the body of the implant. Machining can include, but is not limited to, CNC machining including mills and turning centers. Machining the body 15 to form the nose 22 forms smooth surfaces 30 of the nose 22 and machining the body 15 to form the attachment member 24 and recesses 26, 28 creates smooth surfaces 32. The smooth surfaces 30 of the nose 22 make it easier to advance the implant 10 into an intervertebral space. The smooth surfaces 30, 32 have a surface roughness approximately 30-60 roughness average or 30-65 root mean squared, compared to the unmachined surfaces 12 having a surface roughness in the range of 900 to 1100 roughness average, such as approximately 1000 roughness average (approximately 1100 root mean squared). The machining thereby smooths out the irregularities that create the rough surfaces 12 produced by selective laser sintering PEKK.

Machining the attachment member 24 and recesses 26, 28 into the body 15 provides high accuracy for the geometry of the attachment member 24 and recesses 26, 28 that may not be possible by selective laser sintering PEKK. High accuracy of the attachment member 24 and recesses 26, 28 provides desired tolerances so that the attachment member 24 may be properly secured to an inserter tool. In this manner, the implant 10 combines the rough surfaces 12 from fabricating of the body 15 that improve bone on-growth to the implant 10, the high-accuracy geometry of the attachment member 24 and recesses 26, 28 which allow the implant 10 to be securely grasped by an inserter tool, and the smooth profile of the nose 22 to improve insertion of the implant 10.

Figure 2:
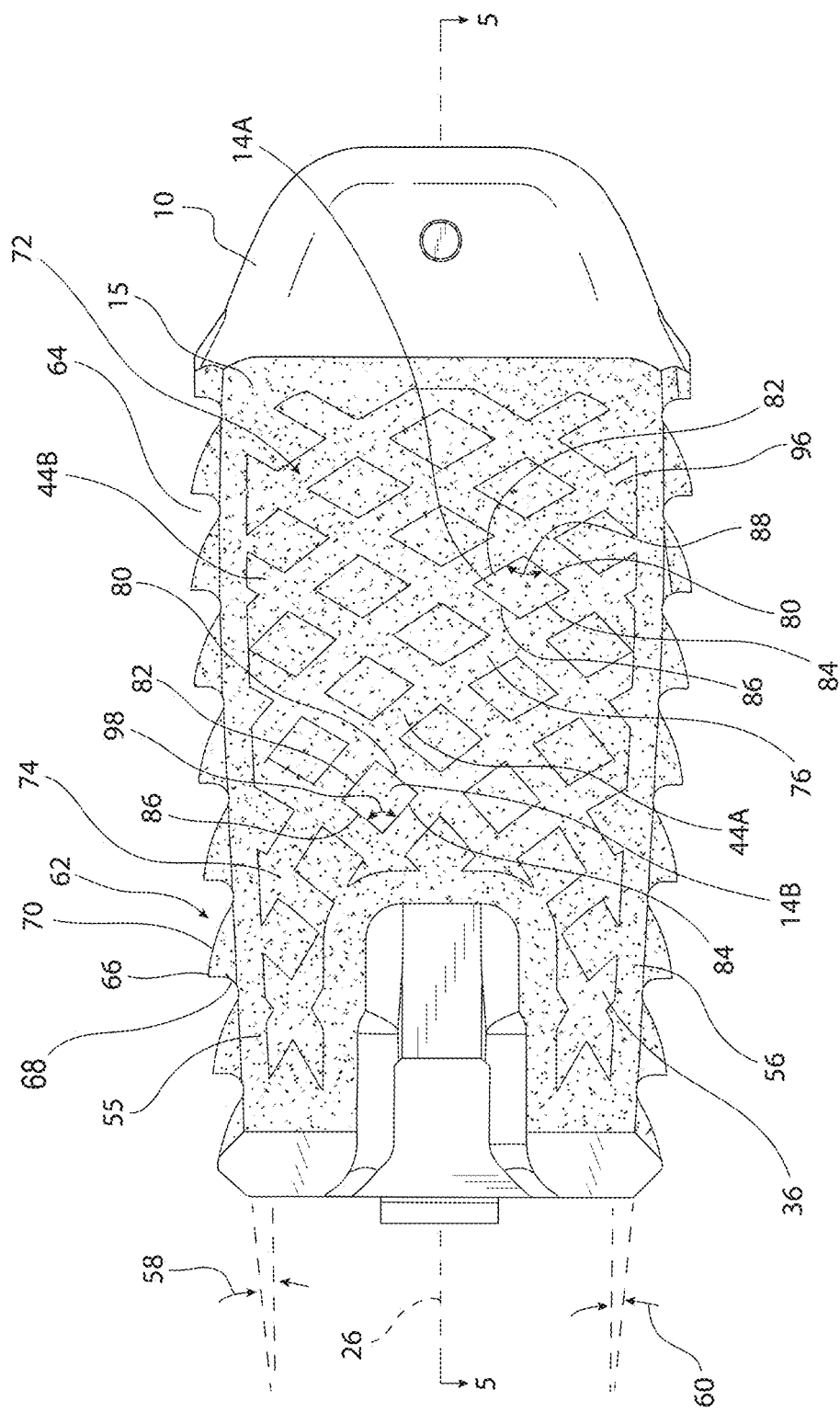
FIG. 2 is a side elevational view of the implant of FIG. 1 showing a pattern of nubs and pathways on a side of the implant.
Figure 3:
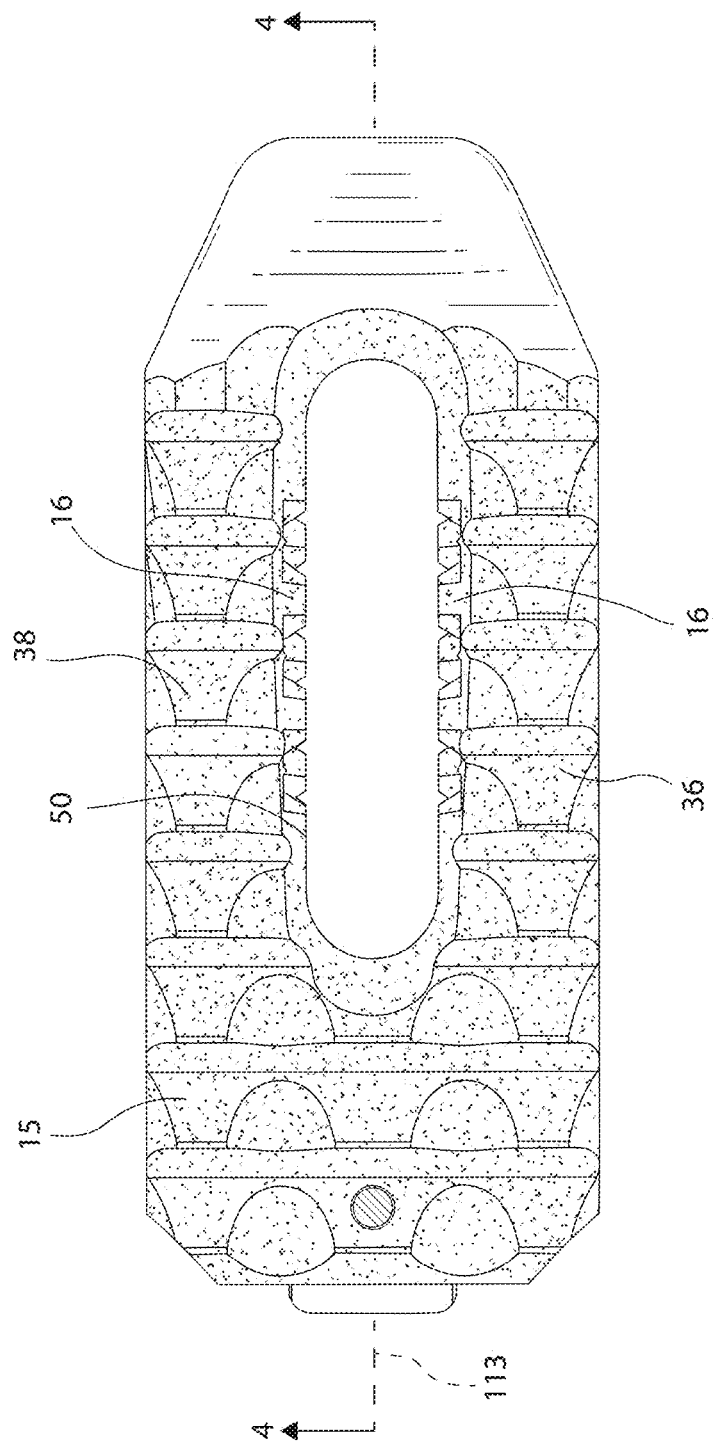
FIG. 3 is a top plan view of the implant of FIG. 2 showing an annular wall of the implant extending around a through opening of the implant for receiving bone growth material.

With reference to FIGS. 1 and 2, the body 15 includes an annular wall 34 encircling a compartment, such as formed by a through opening 35, for receiving bone growth material. The bone growth material may include autograph, allograph, allogenic bone graft, demineralized bone matrix, hydroxyapatite. The annular wall 34 includes lateral wall portions 36, 38 spaced apart from each other on opposite sides of the through opening 35. The lateral wall portions 36, 38 have an outer surface 40 with a pattern 42. The pattern 42 includes the nubs 14 and pathways 44 between the nubs 14. The nubs 14 increase the surface area of the outer surface 40 for bone to grow onto. The pathways 44 provide spaces for bone to grow along the outer surfaces 40 of the lateral walls portions 36, 38.

The lateral wall portions 36, 38 each have an inner surface 50 with a pattern 52 that includes the nubs 16 and pathways 54 as shown in FIG. 1. The nubs 16 increase the surface area of the inner surface 50 for on-growth of bone and assist in the retention of the bone growth material within the though opening 35 during installation of the implant 10 between adjacent vertebrae. The pathways 54 provide spaces between the nubs 16 through which bone growth material is packed and retained as the surgeon packs the through opening 35 with bone growth material.

Further, after the body 15 has been fabricated by selective laser sintering PEKK, the body 14 can be low pressure blasted to remove excess PEKK leftover from the selective laser sintering process. The leftover PEKK on the body 15 resembles hardened clumps of sand that is broken off from the body 15. The low pressure blasting may involve pressures less than 20-100 pounds per square inch, such as 50 pounds per square inch, and may utilize glass, bead, sand, and/or dry ice particles as the blasting medium. The pathways 54 permit particles from the low pressure blast process process to travel along the inner surface 50 and remove leftover PEKK from the inner surface 50. For example, with reference to FIG. 4, the low pressure blasting particles can travel in direction 104 through the pathway 54A. This allows the low pressure blasting particles to remove debris from difficult-to-reach portions of the inner surface 50, such as the undersides of the nubs 16. In this manner, the pathways 54 make it easier to clean the body 15 after fabricating the body 15.

With reference to FIG. 2, the annular wall 34 includes an upper bone engaging portion 55 and a lower bone engaging portion 56. The upper and lower bone engaging portions 55, 56 may be oriented to have angles 58, 60 of zero to eighteen degrees so that the upper and lower bone engaging portions 55, 56 match the patient's anatomy. The upper and lower bone engaging portions 55, 56 may thereby taper toward each other as the body 15 extends from the nose 22 to the attachment member 24. The upper and lower bone engaging portions 55, 56 include gripping members 62 separated by recesses 64. The gripping members 62 each have a peak 66 at which a trailing surface 68 and a leading surface 70 meet. The peak 66 may be sharp to engage the end plates of the vertebrae. The gripping members 62 may have various shapes, such as saw teeth, sine wave, pyramids, curved teeth, etc.

The pattern 42 extends from the upper bone engaging portion 55 to the lower bone engaging portion 56 along the outer surfaces 40 of each of the lateral wall portions 36, 38. The pathways 44 form a lattice pattern 72 as shown in FIG. 2. The lattice pattern 72 includes crisscrossing pathways 44 such as pathway 44A and pathway 44B that each extend from the upper bone engaging portion 55 to the lower bone engaging portion 56. The pathways 44A, 44B may have a variety of shapes including linear and non-linear. For example, the pathway 44A may have a first pathway portion 74 and a second pathway portion 76 that extend transversely to each other. One or more of the pathways 44 may be curved or have a portion that is curved.

The crisscrossing pathways 44 can define the general shape of the nubs 14. In one form, the nubs 14 have a diamond-like shape. With respect to nub 14A, the nub 14A has a continuous peripheral outer surface extending thereabout including sides 80, 82, 84, 86. The pairs of sides 80, 82 and 84, 86 are each oriented at angles 88 relative to each other. The shape of the nubs 14 may change throughout the pattern 42. For example, the nub 14B has sides 80, 82, 84, 86 and each pair of sides 80, 82, and 84, 86 are oriented at angles 98 that are smaller than the angles 88. The nub 14A therefore appears elongated while the nub 14B more resembles a square. With reference to FIGS. 1 and 2, the sides 80, 82, 84, 86 of the nubs 14 extend outward from base surfaces 96 of the pathways 44 generally perpendicular to the base surfaces 96.

Figure 4:
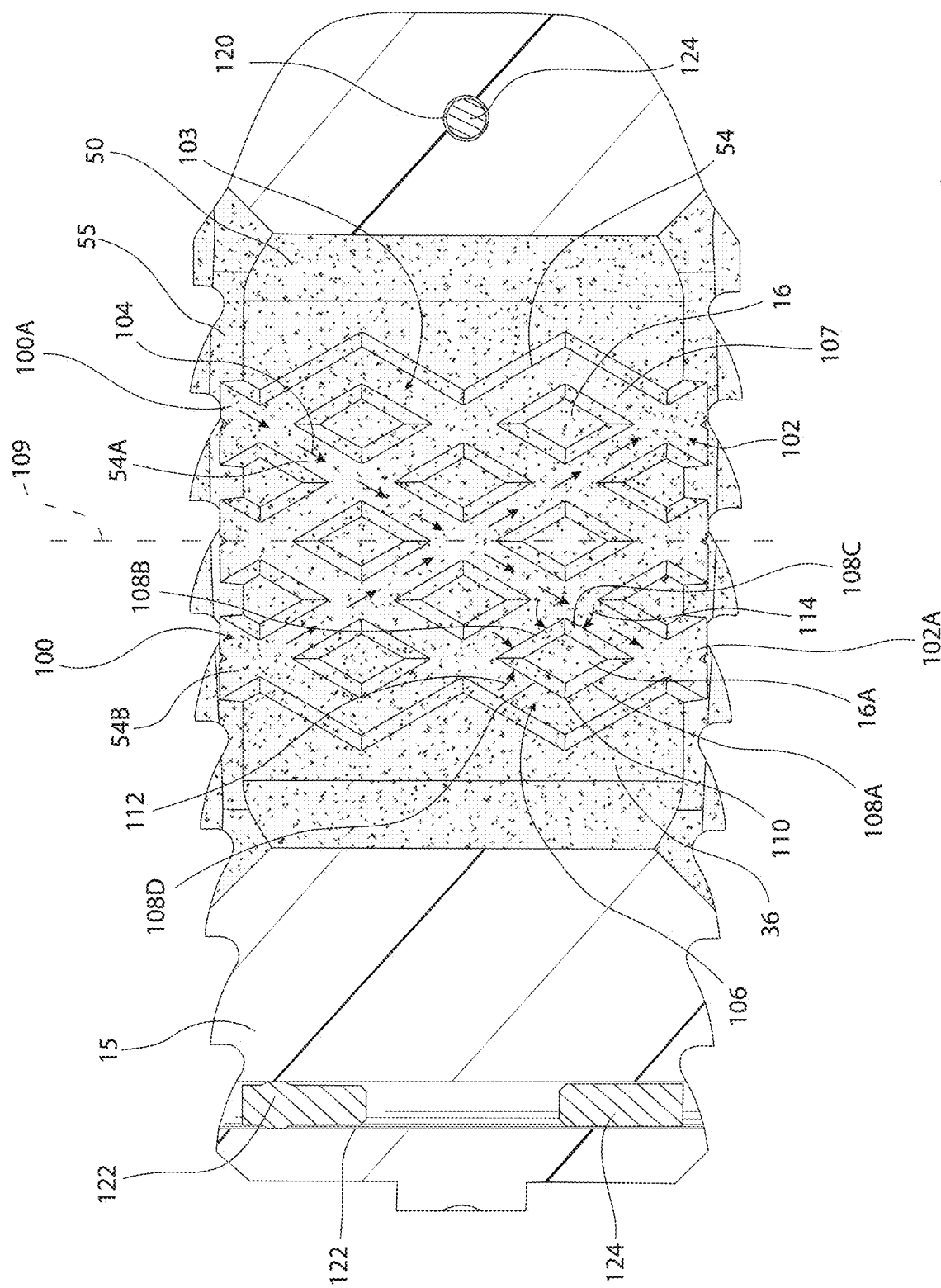
FIG. 4 is a cross-sectional view taken across line 4-4 in FIG. 3 showing a pattern of nubs and pathways on an inner surface of a wall of the implant.

With reference to FIG. 4, the pattern 52 on the inner surface 50 of each of the lateral wall portions 36, 38 includes the nubs 16 and pathways 54. The pathways 54 include openings 100 at the upper bone engaging portion 55 and openings 102 at the lower bone engaging portion 56. The pattern 52 includes recessed base surfaces 107 separating the nubs 16. Due to the openings 100, 102, the recessed base surfaces 107 extend all the way between the top and bottom of the body 15. The base surfaces 107 and nubs 16 define the pathways 54. For example, the pathway 54A extends from the opening 100A to the opening 102A. The pathway 54A permits bone growth material to move in the through opening 35 in direction 104 between the nubs 16. The pathways 54 intersect each other and form a lattice 103 of crisscrossing or intersecting pathways 54. For example, the pathway 54B extends from the upper bone engaging portion 55 to the lower bone engaging portion 56 and intersects the pathway 54A. The intersecting pathways 54 define the general shape of the nubs 16. The nubs 16 each have a continuous peripheral surface 106 that extends from the base surface 107 of the pathways 54. The peripheral surface 106 of each nub 16 is completely spaced from the peripheral surface 106 of the surrounding nubs 16. The nubs 16 are localized protrusions that extend into the through opening 35 from the base surfaces 107 of the pathways 54.

With reference to nub 16A, the peripheral surface 106 of the nub 16A includes side surfaces 108A, 108B, 108C, 108D that are interconnected by corner edges 110. The side surfaces 108B, 108D are oriented to extend to an angle 112 relative to one another, and the side surfaces 108A, 108C are oriented to extend at an angle similar to angle 112. The side surfaces 108B, 108C are oriented to extend at an angle 114 relative to one another and the side surfaces 108A, 108D are oriented to extend at an angle similar to angle 114. The angle 114 is larger than the angle 112 such that the nub 16A is elongated along a vertical axis 109 of the body 15. The angle 112 may be approximately 60 degrees and the angle 114 may be approximately 120 degrees. The side surfaces 108A-108D may each extend obliquely into the through opening 35 relative to the base surfaces 107 of the pathways 54. This provides a more tapered profile of the nubs 16 as the nubs 16 extend at an incline into the throughbore 35 than the nubs 14. The obliquely inclined side surfaces 108A-108D may function as ramps to direct debris off of the nubs 16 during low pressure blasting of the body 15 after the body 15 has been fabricated using selective laser sintering. This makes the body 15 easier to clean after fabrication.

Figure 5:
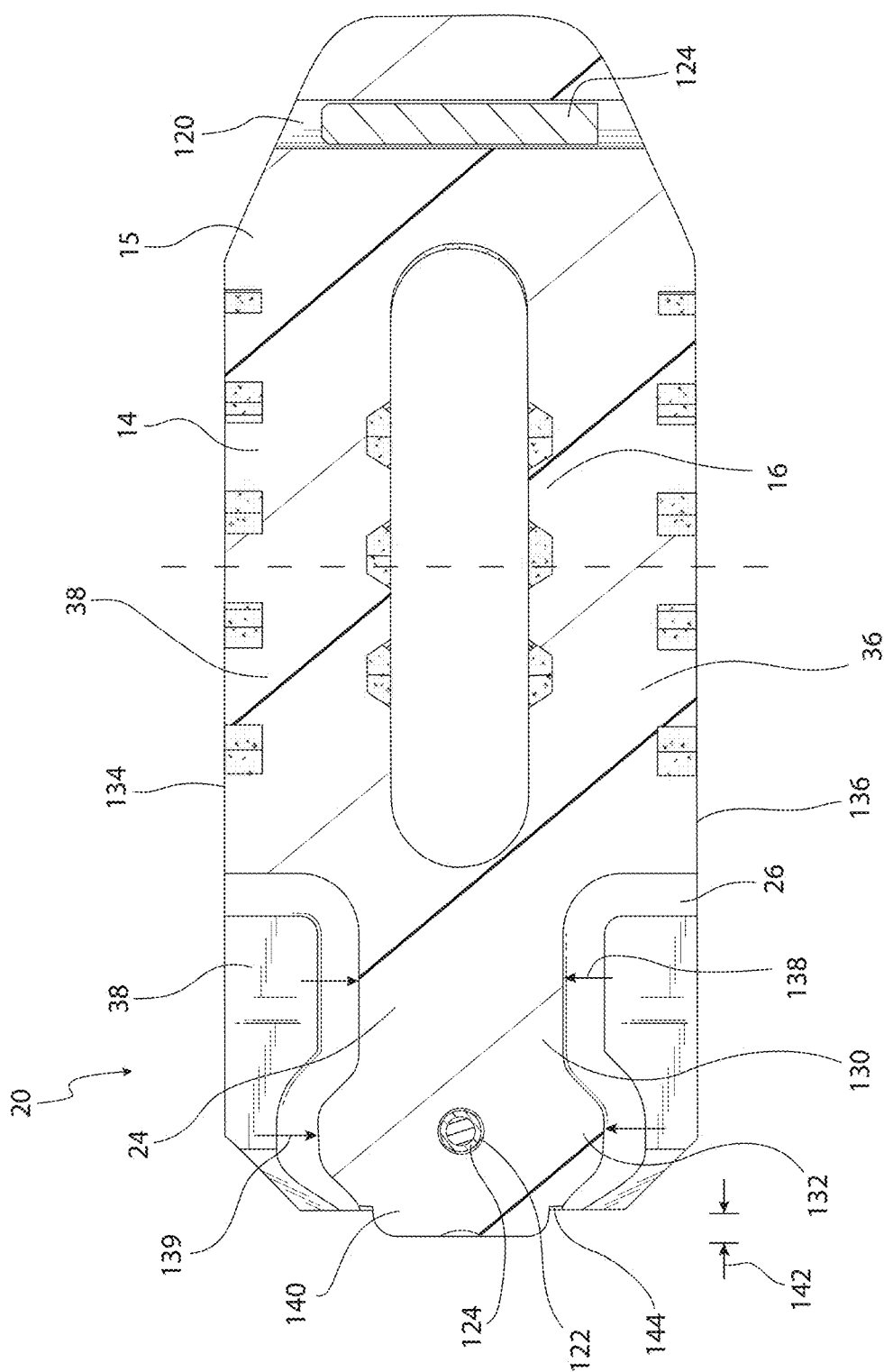
FIG. 5 is a cross-sectional view taken across line 5-5 in FIG. 2 showing an attachment member for being clamped between arms of an inserter tool.
Figure 6:
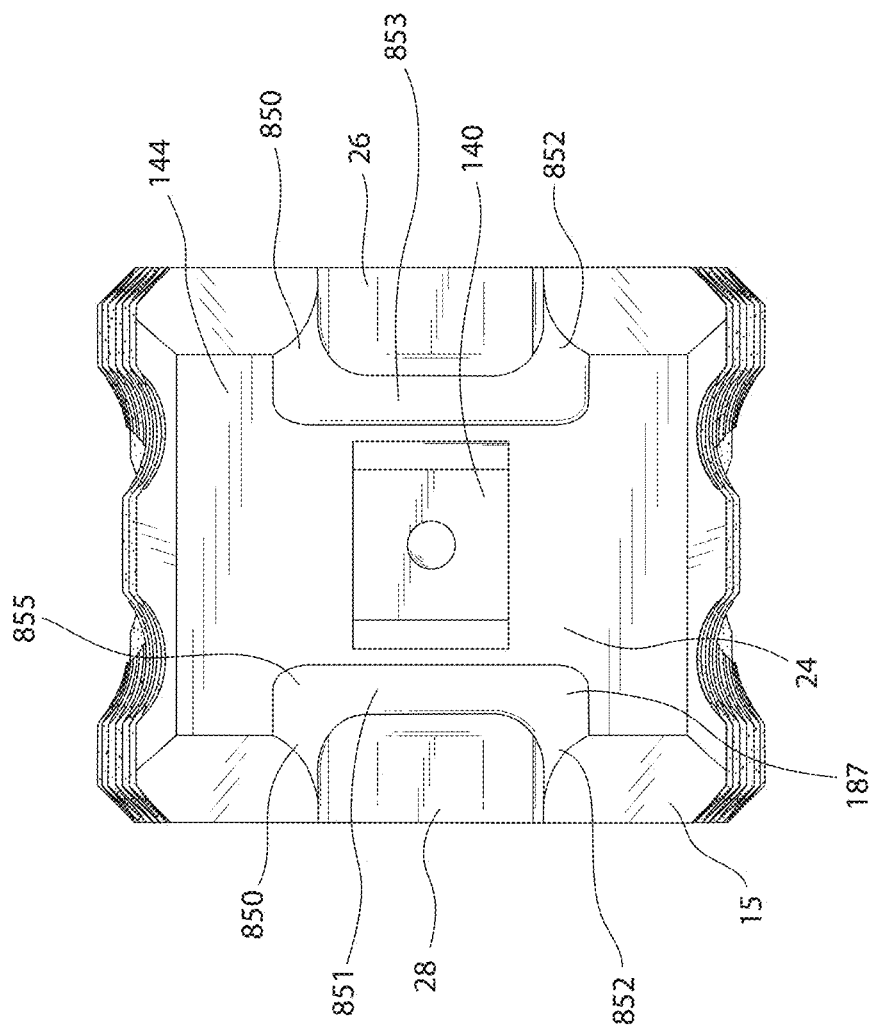
FIG. 6 is a rear elevational view of the implant of FIG. 2 showing recesses on opposite sides of the attachment member that receive the inserter tool arms.

With reference to FIGS. 5 and 6, the trailing end portion 20 includes the attachment member 24 and recesses 26, 28 on opposite sides of the attachment member 24. The recesses 26, 28 receive arms of an inserter tool. The attachment member 24 has a neck portion 130 and a head portion 132. The neck portion 130 is recessed from lateral sides 134, 136 of the lateral wall portions 36, 38. The head portion 132 and neck portion 130 permit the inserter tool arms to be received so that their outer surfaces are laterally inward from or flush with the lateral sides 134, 136. Because the inserter tool arms are inward from or flush with the lateral sides 134, 136, the inserter tool arms avoid becoming caught on tissue or bone as the implant 10 is advanced into the intervertebral space.

The neck portion 130 can have a width 138 of approximately 0.170 inches and the head portion 132 can have a width 139 of approximately 0.240 inches such that the head portion 132 is enlarged relative to the neck portion 130. The width 138 may be in the range of approximately 0.118 inches to approximately 0.197 inches and the width 139 may be in the range of approximately 0.197 inches to approximately 0.276 inches. The ratio of the width 139 to the width 138 may be in the range of 1.1 to 2.4, such as 1.3 to 2.0, and may be approximately 1.4. The head portion 132 and neck portion 130 provide a thick, block-like structure for the inserter tool arms to engage and grab. The overall width of the implant 10 between the sides 134, 136 may be approximately 0.394 inches.

The attachment member 24 also includes a boss 140 extending longitudinally for a distance 142 from a trailing end surface 144 of the attachment member 24. The trailing end surface 144 may be flat, and the boss 140 may have a generally cuboid shape that extends rearward from the trailing end surface 144. The boss 140 operates as a plug that fits within a socket of the inserter tool (see FIG. 35) to increase the length of the engagement between the implant 10 and the inserter tool. This improves the strength of the connection between the implant 10 and the inserter tool by providing better torque resistance as discussed in greater detail below.

With reference to FIG. 6, the implant body 15 includes ceilings 850, floors 852, and lateral sides 851, 853 of the attachment member 24 defining the recesses 26, 28. The body 15 includes corners 855, 857 connecting the ceilings 850 and floors 825 to the lateral sides 851, 853. The corners 855, 857 are relatively sharp, such as 90 degrees. By machining the PEKK material, the corners 855, 857 of the implant attachment portion 23 can be formed with tight tolerances. Further, the somewhat U-shaped recesses 26, 28 extending laterally inward into the body 15 as shown in FIG. 6 provide pockets to receive the arms of an inserter tool with the outer surfaces of the arms laterally inward from or flush with the lateral sides of the implant 10.

Figure 7:
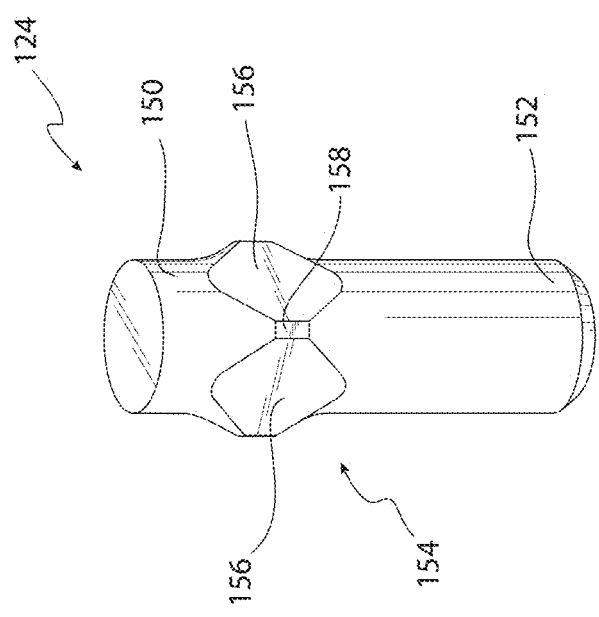
FIG. 7 is a perspective view of a marker pin of the implant of FIG. 2 showing flats and edges of the marker pin.

With reference to FIGS. 4 and 5, the body 15 includes through apertures 120, 122 for receiving marker pins 124. The marker pins 124 may be radiolucent to indicate the orientation of the implant 10 during x-ray imaging of the surgical site. Turning to FIG. 7, each marker pin 124 may have a trailing end portion such as an upper end portion 150, a leading end portion such as a lower end portion 152, and an interference portion such as an enlarged portion 154 intermediate the upper and lower end portions 150, 152. The enlarged portion 154 has a larger radius than the apertures 120, 122 to be in interference therewith.

The upper and lower portions 150, 152 have a circular cross-section and the enlarged portion 154 has a non-circular cross-section, such as a polygonal cross-section such as the illustrated generally rectangular cross section. As illustrated, the enlarged portion 154 includes flats 156 and corner junctures or edges 158 which connect the flats 156. When the marker pins 124 are received in the body apertures 120, 122, the edges 158 engage the surfaces about the apertures 120, 122 to deform the material of the body 15 and fix the marker pin 124 within the apertures 120, 122. By deforming the material of the body 15 with the edges 158, the marker pin 124 deforms a smaller portion of the body around the apertures 120, 122 which reduces the likelihood of the body 15 fracturing around the apertures 120, 122. Using the edges 158 to locally deform the material of the body 15 provides reduced stress in the body 15 in comparison to a cylindrical marker pin having a diameter larger than the apertures 120, 122 that is press fit into the apertures 120, 122 and engages the body 10 around the entire circumference of the marker pin.

Figure 8:
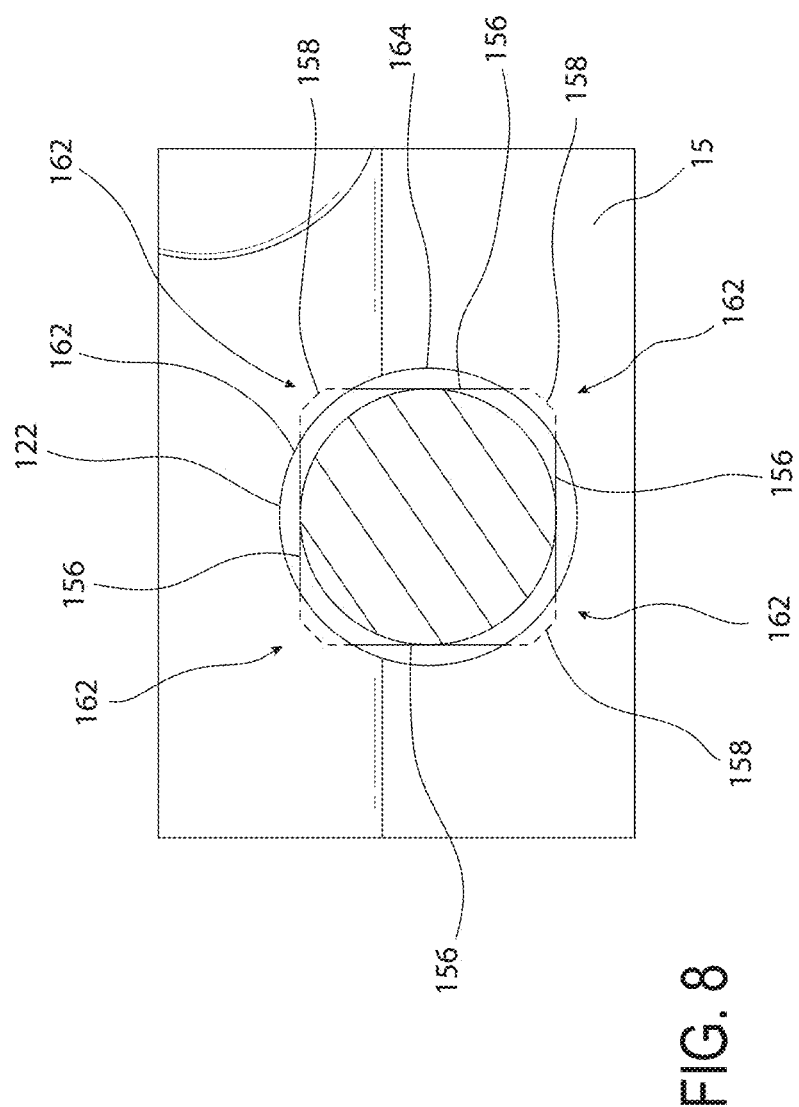
FIG. 8 is a top plan view of the marker of FIG. 7 in an opening of the implant of FIG. 2 and the edges of the marker pin engaging a body of the implant at spaced locations around the opening.

For example and with reference to FIG. 8, the through bore 122 has an opening surface 160 extending around the opening 122. As the marker pin 124 is advanced into the opening 122, the edges 158 bite into the surface 160 and create localized deformations 162 of the body 15 at each of the edges 158. Because the marker pin 154 has flats 156 separating the edges 158, the implant body 15 has undeformed portions 164 separating the localized deformations 162. By deforming less of the area of the opening surface 160, the implant 15 is stronger due to the reduced stress in the material of the body 15 surrounding the apertures 120, 122.

As noted above, PEKK is more brittle than PEEK at smaller features such as relatively thin wall portions 36, 38. To increase the strength of the annular wall 34, the annular wall 34 is free of through apertures in communication with the through opening 35 that extend between the inner and outer surfaces 40, 50 and would otherwise cause stress concentrations in the annular wall 34. The annular wall 34 is therefore stronger in compression which makes the implant 10 more durable. Through apertures are often used in the walls of PEEK implants to permit bone growth through the aperture. Although the annular wall 34 lacks through apertures that permit bone growth therethrough, the rough exterior surfaces 12 and the nubs 14, 16 provide significant implant osseointegration without through apertures.

Figure 9:
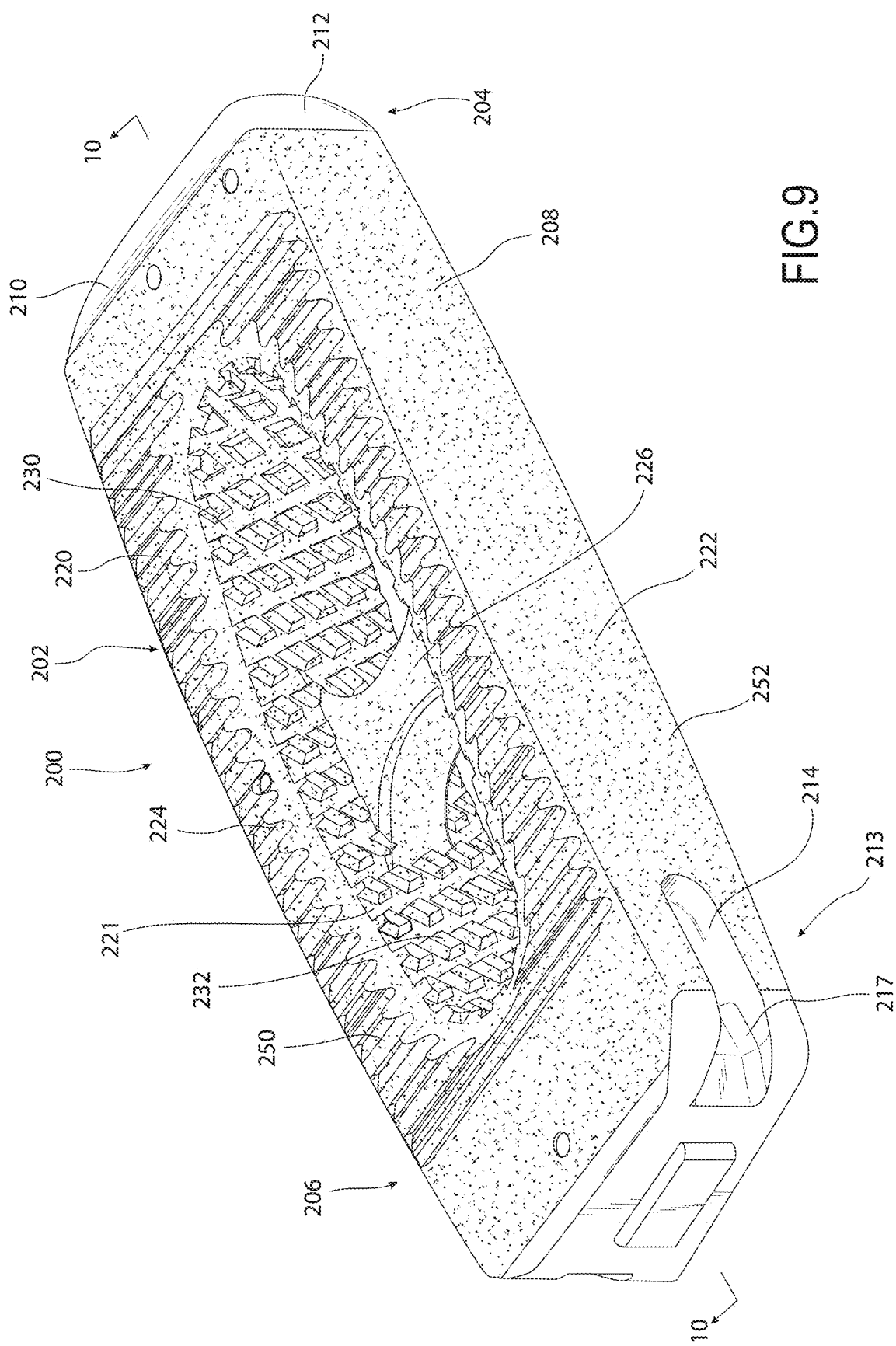
FIG. 9 is a perspective view of another implant showing rough, irregular surfaces of the implant formed by fabricating the implant by selective laser sintering PEKK and smoother, machined surfaces of the implant.

With reference to FIG. 9, an implant 200 is provided that a similar in many respects to the implant 10 discussed above such that differences between the implants 10, 200 will be highlighted. The implant 200 includes a body 202 having a leading end portion 204 and a trailing end portion 206. The body 202 may be formed by selective laser sintering PEKK and has rough, unmachined surfaces 208. The trailing end portion 206 includes an attachment portion 213 including an attachment member 215 and recesses 214, 216 on opposite sides of the attachment member 215. The nose 210 and attachment portion 213 are machined into the body 202 after the body 202 has been fabricated such that the nose 210 and attachment portion 213 have smooth, machined surfaces 212, 217.

With reference to FIG. 9, the body 202 includes an annular wall 220 extending around a compartment, such as a through opening 221. The through opening 221 receives bone growth material. The annular wall 220 includes lateral side walls 222, 224 and the body 202 includes a web 226 extending between the lateral side walls 222, 224. The annular wall 222 has an inner surface 230 defining at least a portion of the through opening 221. The inner surface 230 includes nubs 232.

Figure 10:
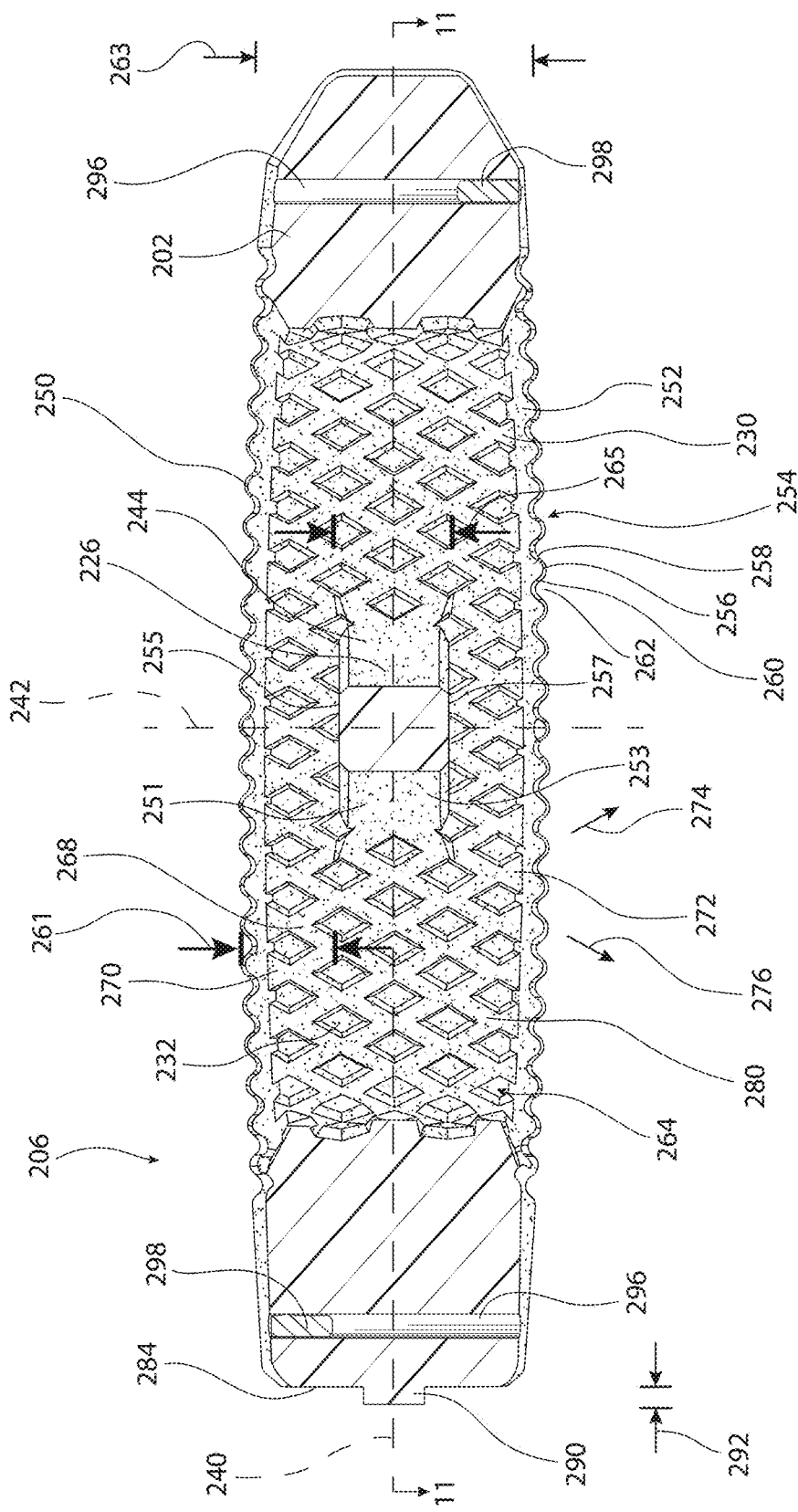
FIG. 10 is a cross-sectional view of the implant taken across line 10-10 in FIG. 9 showing a pattern of pathways and nubs on an inner surface of the implant.
Figure 11:
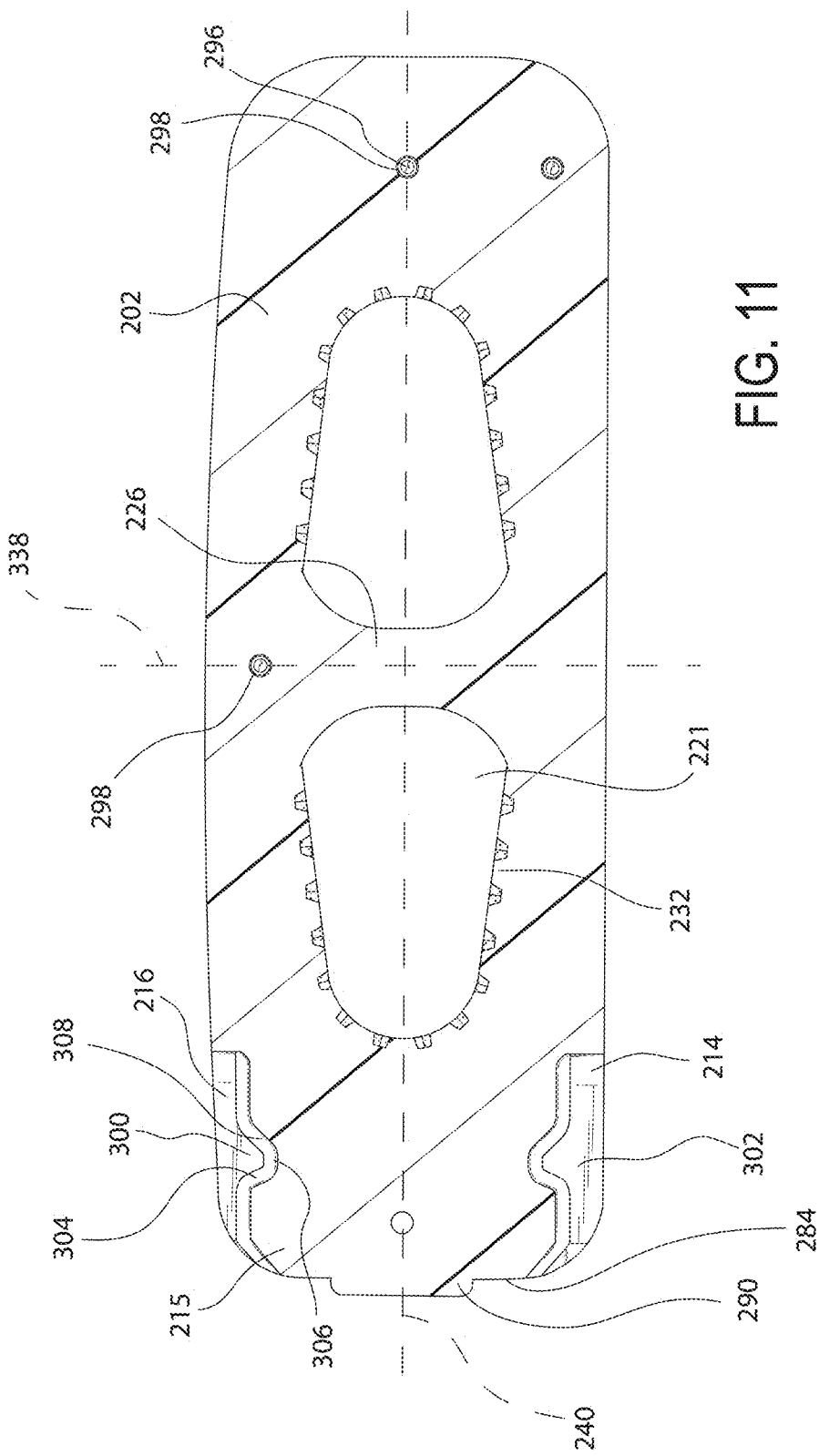
FIG. 11 is a cross-sectional view taken across line 11-11 in FIG. 10 showing a web of the implant extending across a through opening of the implant.

With reference to FIGS. 10 and 11, the implant 200 includes a longitudinal axis 240, a vertical axis 242, and a lateral axis 338. The web 226 extends across the through opening 221 transverse, such as perpendicular, to axes 240, 242 and along the lateral axis 338. The web 226 has a base 244 that tapers outwardly as the web 226 reaches the inner surface 230 at each of the lateral side walls 222, 224. The annular wall 220 includes an upper bone engaging portion 250 and a lower bone engaging portion 260. The upper and lower bone engagement portions 250, 252 include gripping members 254 that each have a peak 256, a leading surface 258, and a trailing surface 260. The upper and lower bone engaging portions 250, 252 include recesses 262 between the gripping members 254. The peaks 256 may be rounded and the leading and trailing surfaces 258, 260 may also be rounded to form an undulating surface of the upper and lower bone engaging portions 250, 252.

The web 226 has an uppermost portion 251 and a lowermost portion 253 that include, respectively, a top surface 255 and a bottom surface 257. The uppermost and lowermost portions 251, 253 are recessed relative to the upper and lower bone engaging portions 250, 252. Because the uppermost and lowermost portions 251, 253 of the web 226 are recessed, the web 226 avoids contacting bones during insertion of the implant 200 into an intervertebral space between the bones. This reduces the surface area of the implant 200 that can contact the bones and resist advancing of the implant 200 into the intervertebral space. If the body 202 is fabricated by selective laser sintering PEKK, the body 202 may be more brittle than an implant milled from a block of PEEK. The recessed web 226 may reduce the resistance to advancing the implant 200 such that the surgeon may apply less force to the implant 200 via an inserter tool.

The web 226 may have a rectangular cross-section taken normal to the lateral axis 338 and the web 226 has top and bottom surfaces 255, 257 that may be flat or rounded. The top and bottom surfaces 255, 257 extend from one lateral side wall 222, 224 to the other. The top and bottom surfaces 255, 257 of the web 226 may each be spaced from the peaks 256 of the gripping members 254 of the respective upper and lower bone engaging portions 250, 252 by a distance 261. The implant 200 may be provided in various heights 263 and the web 226 has a height 265 that may be the same for different heights 263 of the implant 200. Thus, the distance 261 may be greater for taller implants 200 than for implants 200 with shorter heights 263.

With reference to FIG. 10, the annular wall 220 includes a pattern 264 and includes the nubs 232 and intersecting or crisscrossing pathways 268 that form a lattice. The pathways 268 include openings 270 at the upper bone engaging portion 250 and openings 272 at the lower bone engaging portion 252. The pathways 268 permit low pressure blasting particles to travel therethrough and remove debris left on the nubs 232 from fabrication of the body 202. The pathways 268 also permit bone growth material to travel between the nubs 232 as the bone growth material is packed into the through opening 221. The nubs 232 have a shape similar to the nubs 16 discussed above and extend inwardly from base surfaces 280 of the pathways 268. The nubs 232 therefore increase the surface area of the inner surface 230 of the annular wall 220 to improve bone on-growth. The nubs 232 also operate to retain bone growth material in the through opening 221.

With reference to FIGS. 10 and 11, the trailing end portion 206 includes a substantially flat trailing end surface 284 and the attachment member 215 includes a rectangular boss 290 that extends longitudinally outward from the trailing end surface 284 a distance 292. The boss 290 forms a plug-fit engagement with a socket of an inserter tool as discussed in greater detail below with reference to FIG. 42. The boss 290 increases the longitudinal length of engagement between the inserter and the implant 200 to distribute loading from the inserter to the implant 200 over a larger portion of the implant 200 which limits stress concentrations in the body 202. The leading and trailing end portions 204, 206 also include bores 296 for receiving marker pins 298.

With reference to FIG. 11, the attachment member 215 includes secondary recesses, such as cavities 300, 302, for receiving projections of arms of an inserter tool. The attachment member 215 includes walls 304, 306, 308 that define the cavities 300, 302. The wall 304 on each side of the attachment member 215 is oriented to extend transverse to the longitudinal axis 240 such that the engagement between the inserter tool arms and the walls 304 cams the attachment member 215 toward the inserter tool as the arms clamp the attachment member 215 therebetween. In this manner, the more tightly the arms of the inserter clamp the attachment member 215, the more the implant 200 is urged proximally into the inserter tool.

Figure 12:
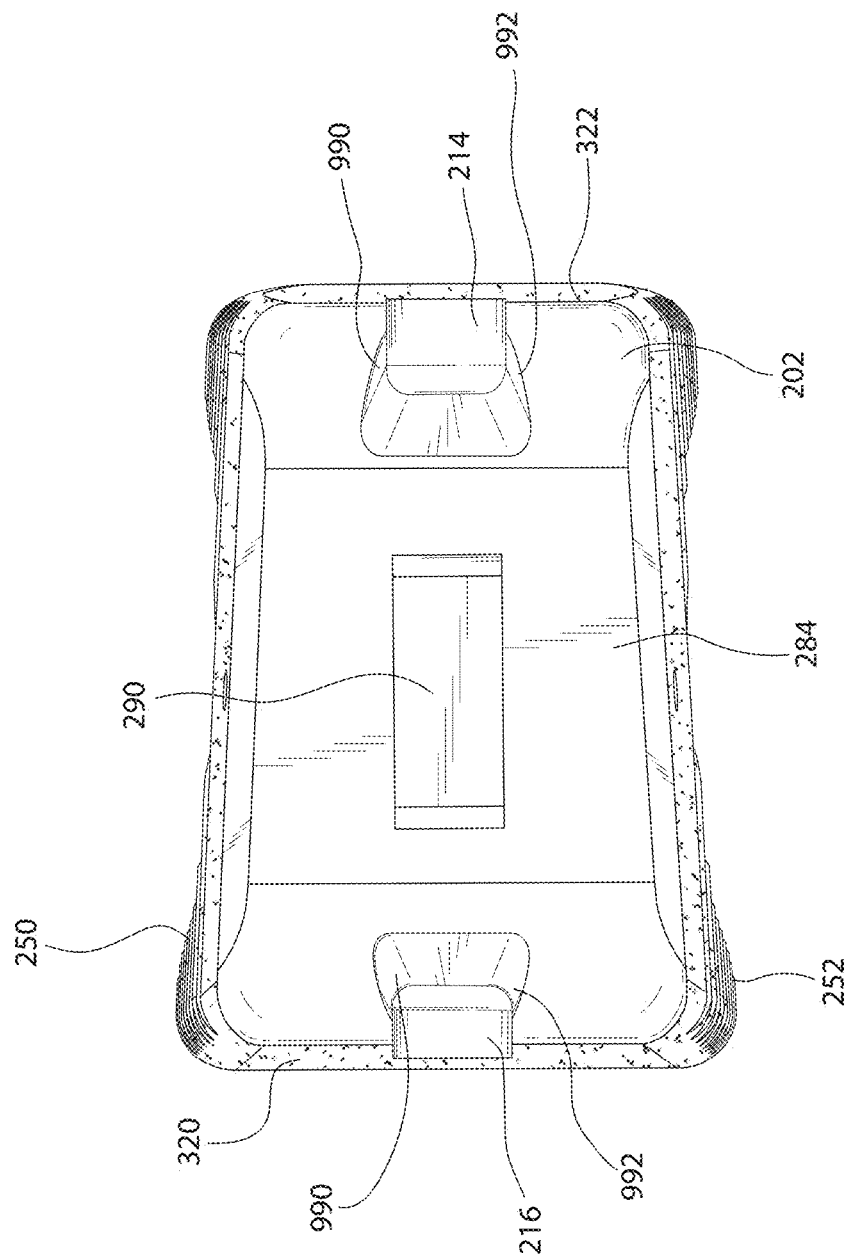
FIG. 12 is a rear elevational view of the implant of FIG. 9 showing recesses on opposite sides of an attachment member of the implant for receiving arms of an inserter tool.

With reference to FIG. 12, the body 202 includes outer lateral surfaces 320, 322 extending from the upper bone engaging portion 250 to the lower bone engaging portion 252. In one form, the lateral surface 320 is taller than the lateral surface 322 such that one lateral side of the implant 200 is taller than the other side. This allows the implant body 202 to match the patient anatomy.

In some forms, the body 15 of the implant 10 is fabricated using additive manufacturing and materials other than PEKK. For example, the body 15 may be made of various types of polymers and metallic materials. Further examples include ceramic, hydroxylapatite, titanium, and PEEK.

Figure 13:
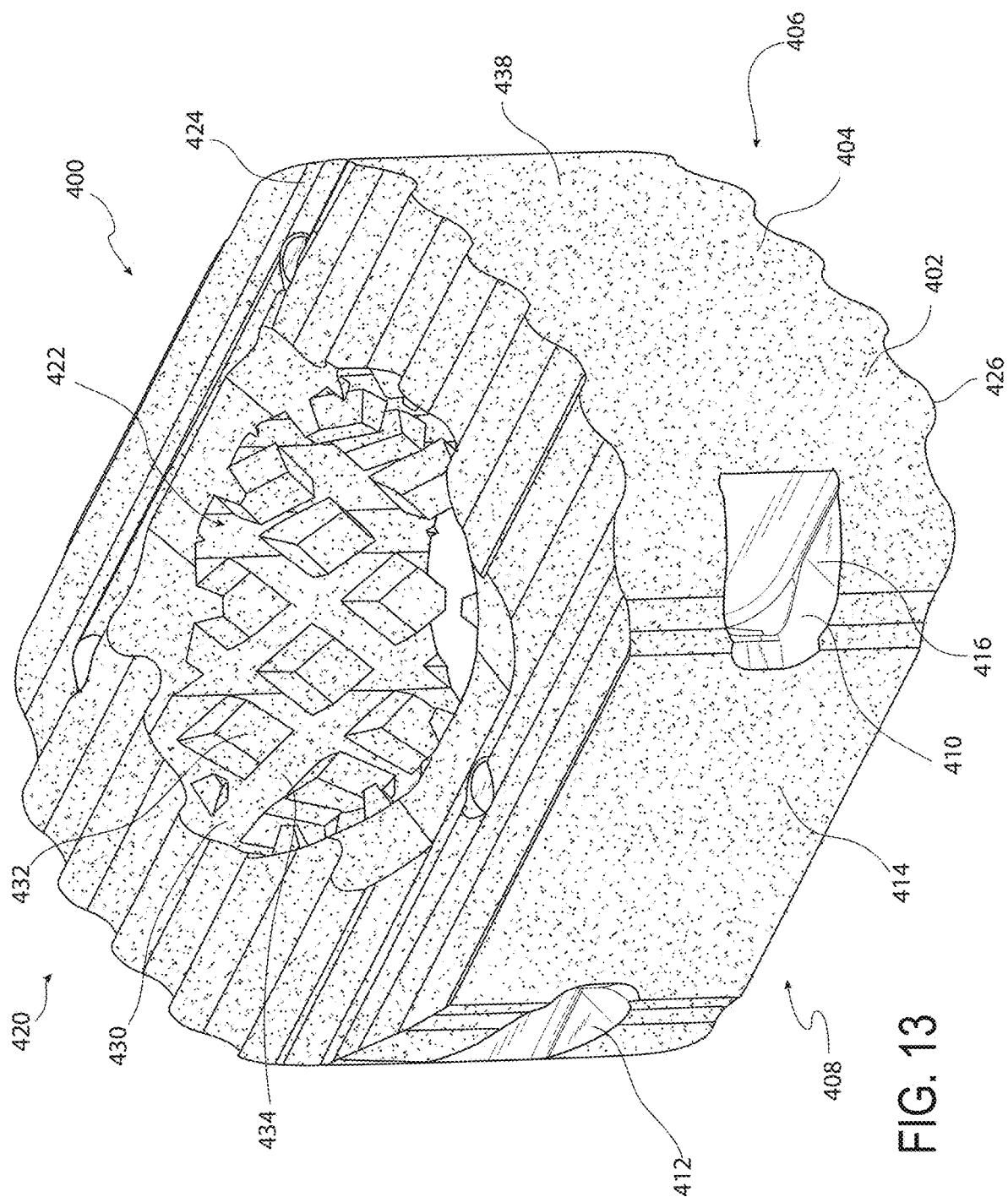
FIG. 13 is a perspective view of an implant showing rough, irregular surfaces of the implant formed by fabricating the implant by selective laser sintering PEKK and smoother, machined surfaces of the implant.
Figure 14:
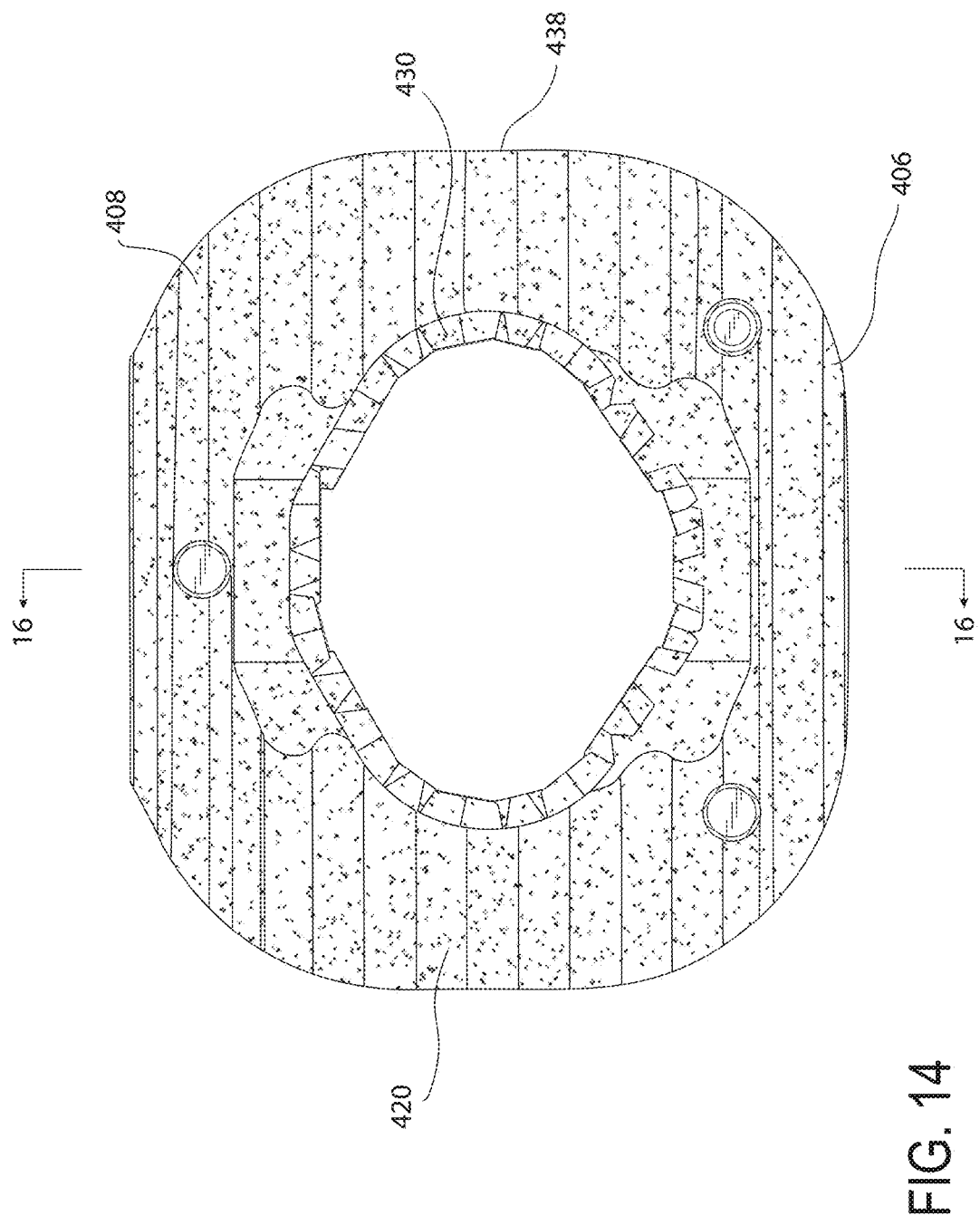
FIG. 14 is a top plan view of the implant of FIG. 13 showing a through opening of the implant and an annular wall extending around the through opening.

With reference to FIG. 13, an implant 400 is provided for being positioned between vertebrae, such as cervical vertebrae, and is similar in many respects to the implants 10, 200 discussed above. The implant 400 has a body 402 that may be fabricated by selective laser sintering PEKK, which results in rough outer surfaces 404 of the body 402. The body 402 includes a leading end portion 406 and a trailing end portion 408. The trailing end portion 408 includes recesses 410, 412 and an attachment member such as a dovetail projection 414 intermediate the recesses 410, 412. The recesses 410, 412 and the dovetail projection 414 are machined into the body 402. This causes the trailing end portion 408 to have smooth machined surfaces 416.

The body 402 includes an annular wall 420 surrounding a compartment, such as a through opening 422, for receiving bone growth material. The annular wall 420 includes an upper bone engaging portion 424 and a lower bone engaging portion 426. The annular wall 420 extends from the upper to the lower bone engaging portion 424, 426 and around the through opening 422 without interruption. By extending without interruption, it is intended to mean that there are no through apertures in communication with the through opening 422 that extend from the inner surface 430 to the outer surface 438. This increases the strength of the annular wall 420 by limiting stress concentrating features.

Figure 15:
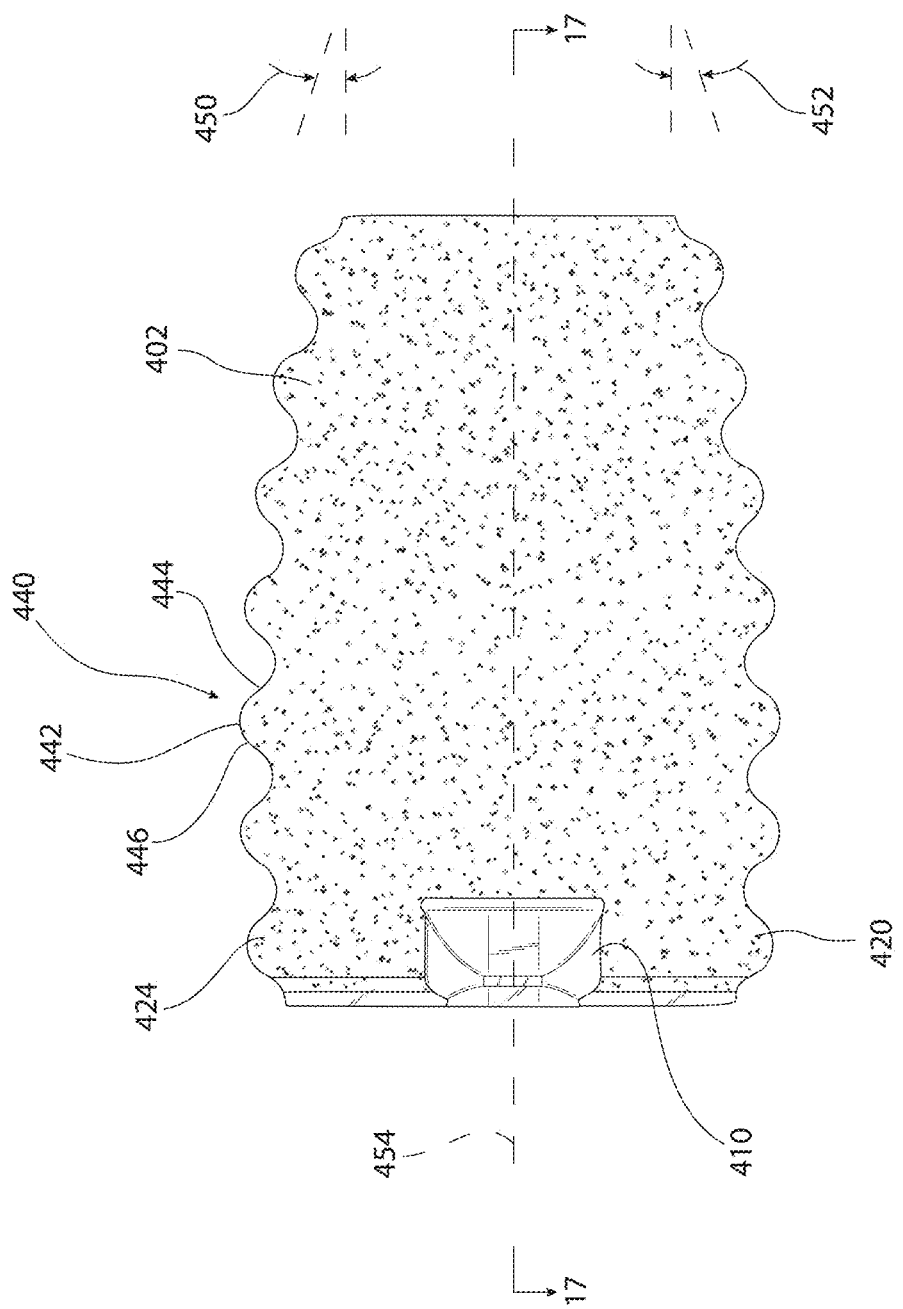
FIG. 15 is a side elevational view of the implant of FIG. 14 showing a wedge-like profile of the implant.

With reference to FIG. 15, the upper and lower bone engaging portions 424, 426 include a plurality of gripping members 440 each having a rounded peak 442 and rounded leading and trailing surfaces 444, 446. The gripping members 440 thereby have an undulating shape along the upper and lower bone engagement portions 424, 426. The upper and lower bone engaging portions 424, 426 are tapered to have angles 450, 452 relative to a longitudinal axis 454 of the body 202. This tapered profile of the implant 200 aids in insertion of the implant 200 between vertebrae.

Figure 16:
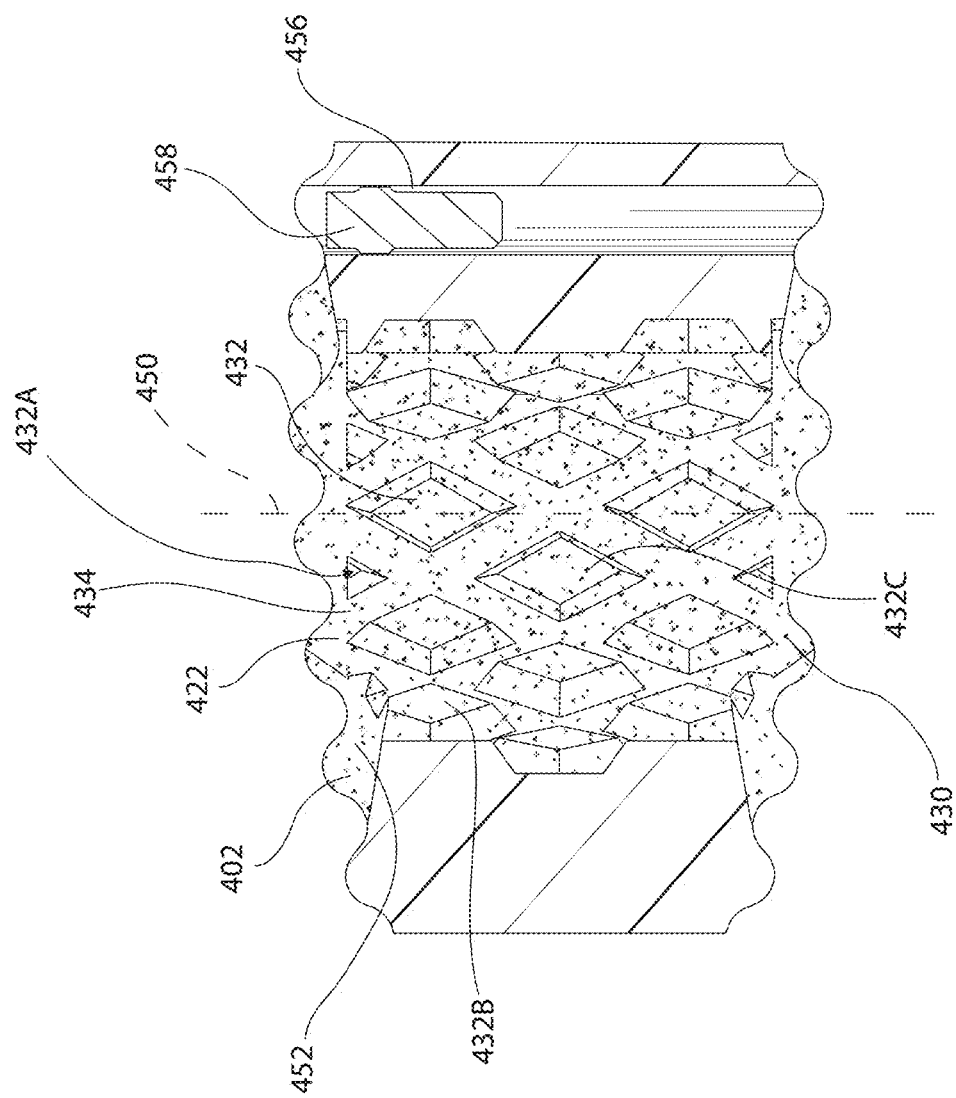
FIG. 16 is a cross-sectional view taken across line 16-16 in FIG. 14 showing a pattern of nubs and pathways of an inner surface of the annular wall.

With reference to FIG. 16, the inner surface 430 of the annular wall 420 extends around a central, vertical axis 450 of the body 402. The annular wall 420 includes nubs 432 and crisscrossing or intersecting pathways 434. The nubs 432 and pathways 434 are similar to the nubs 16, 232 and pathways 54, 268 discussed above. The nubs 432 have varying sizes along the inner surface 430. For example, the nubs 432 include nubs 432A that are truncated or reduced in size near an upper surface 452 of the annular wall 420. The nubs 432 include nubs 432B that are larger than nubs 432A but are partially truncated or reduced in size relative to nubs 432C. The nubs 432C are more toward the middle of the annular wall 420 and not truncated and have a full diamond shape. The body 402 may also include one or more bores 456 that receive marker pins 458.

Figure 17:
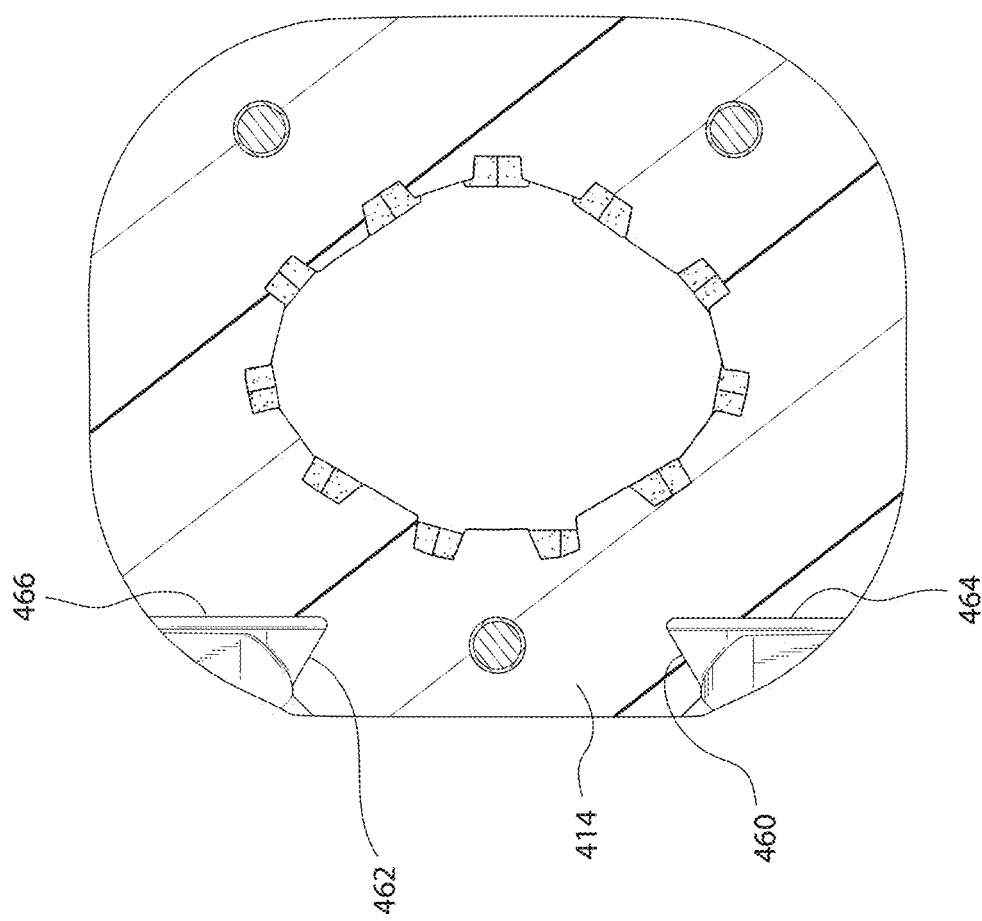
FIG. 17 is a cross-sectional view taken across line 17-17 in FIG. 15 showing an attachment member of the implant for being clamped by arms of an inserter tool.
Figure 18:
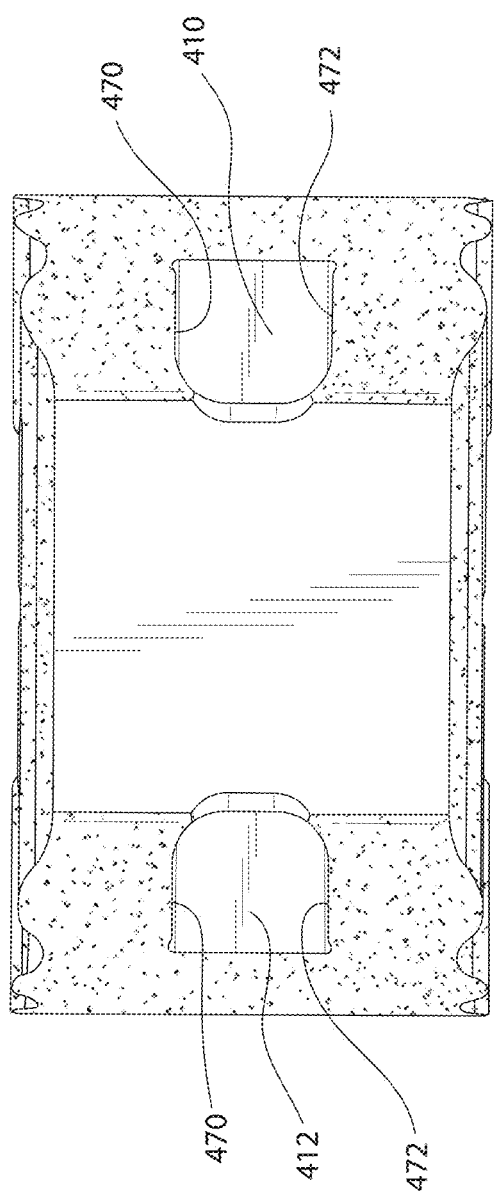
FIG. 18 is a rear elevational view of the implant of FIG. 13 showing recesses on opposite sides of the attachment member for receiving the inserter tool arms.

With reference FIG. 17, the dovetail projection 414 includes inclined walls 460, 462 and walls 464, 466 that extend transversely to the inclined walls 460, 462. The dovetail projection 414 provides a thick structure to receive the compressive forces from the arms of an inserter tool. Further, the walls 464, 464 may abut surfaces of the inserter tool to absorb impacts from the inserter tool such as impacts due to a surgeon striking the inserter tool with a mallet to urge the implant 400 into an intervertebral space. As shown in FIG. 18, the body 402 includes ceilings 470 and floors 472 that form upper and lower boundaries of the recesses 410, 412.

Figure 19:
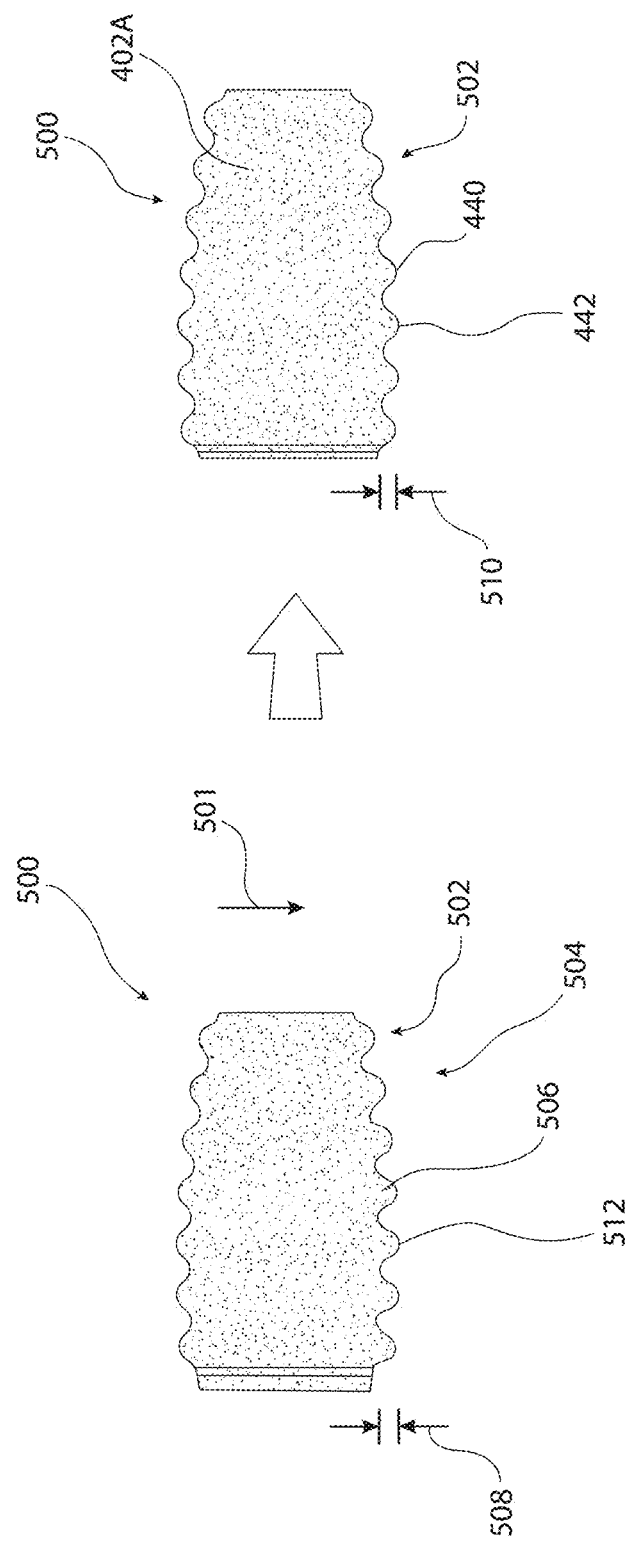
FIG. 19 shows an engineering model of an implant body and the implant body that results from selective laser sintering PEKK based on the model.

With reference to FIG. 19, the process of fabricating the body 402 of the implant 400 involves providing a model 504 to a computer that controls operation of a selective laser sintering machine. The computer uses the model 504 to direct a laser of the machine to fuse particles of a bed of PEKK into layers and forms a printed body 402A by progressively printing one layer after another. The machine starts building the layers of the body 402 by first fusing particles of PEKK to form a skin down surface 500. The machine progressively forms layers one below another in direction 501 until the machine reaches a skin up surface 502 of the printed body 402A. Due to the sintering method used to melt the particles in the PEKK bed, the process may have a lower resolution at the skin down surface 500 then the skin up surface 502. More specifically, the laser hits the particles of the PEKK bed with the most energy when the laser begins to form a first layer, i.e., the skin down surface 500 of the printed body 402A. More particles are added to bed above the first layer, and the laser is directed to form a second layer above the first layer. This process is repeated until the final layer including the skin up surface 502 has been formed. The laser has less energy when it is forming the second and higher layers such that those layers have more accuracy than the first layer.

To compensate for this, the model 504 provided to the computer associated with the selective laser sintering machine may have exaggerated geometry so that printed body 402A that results from the selective laser sintering has the desired geometry. For example, the model 504 may have lower gripping members 506 that have a peak-to-valley height 508 that is greater than a peak-to-valley height 510 of the gripping members 440 of the body 402A that result from the selective laser sintering process. In other words, the gripping members 506 of the model 504 provided to the selective laser sintering machine are more exaggerated than the gripping members 440 that result from the 3D printing process. The difference in a height 508, 510 is due to the lower resolution at the skin down surface 502 causing the gripping members 440 to be smaller than the gripping members 506. Other features of an implant may be emphasized or reduced in the model 504 provided to the selective laser sintering machine. For example, the curvature of peaks 512 of the gripping members 506 may be different than the curvatures of the peaks 442 of the printed body 402A.

With reference to FIG. 20, the selective laser sintering machine produces the printed body 402A. The printed body 402A includes the gripping members 440, the nubs 432, and the through opening 422. The printed body 402A is then machined 520 to impart structural details to the printed body 402A that require higher precision than provided by the selective laser sintering process. For example, the recesses 412, 416 and marker pin bores 456 are machined into the printed body 402A to produce the body 402. The process of machining the recesses 412, 416 into the 3D body 402 produces the smooth machined surfaces 416 of the body 402.

With reference to FIG. 21, fabricating the body 15 includes producing a printed body 15A by selective laser sintering PEKK. The printed body 15A includes the gripping members 62, nubs 14, 16, and through opening 35. The printed body 15A is machined 530 to form the nose 22, recesses 26, 28, boss 140, trailing end surface 144, and marker pin apertures 120, 122 into the printed body 15A. This produces the body 15 discussed above. The machining 530 imparts the smooth machined surfaces 30, 32 of the body 15.

With reference to FIG. 22, fabricating the body 202 includes producing a printed body 202A by selective laser sintering PEKK. The printed body 202A includes the through opening 221, the web 226, the gripping members 254, and the nubs 232. The printed body 202 is then machined 540 to form the nose 210, recesses 214, 216, trailing end surface 284, and boss 290 into the body 202A. The machining 540 imparts the smooth machined surfaces 212, 217.

Figure 25:
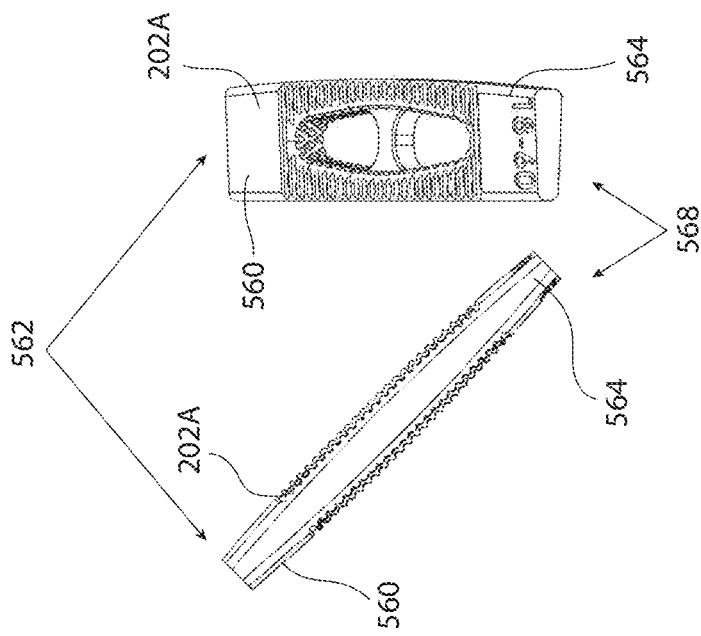
FIGS. 23, 24, and 25 are views showing the orientation of the implant bodies of FIGS. 20, 21, 22 during the selective laser sintering procedure.
Figure 24:
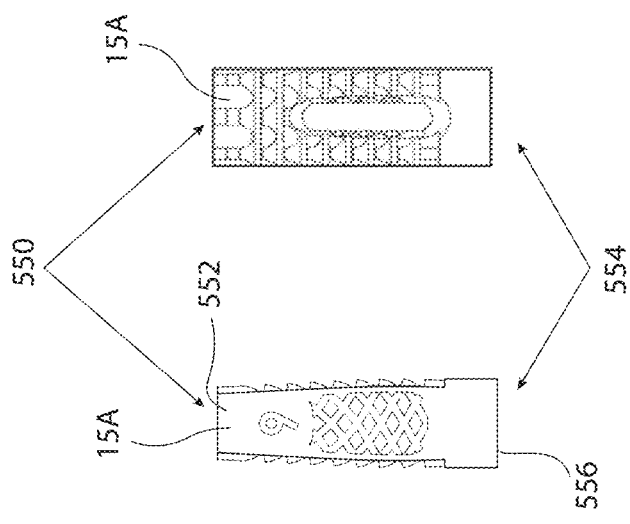
Figure 23:
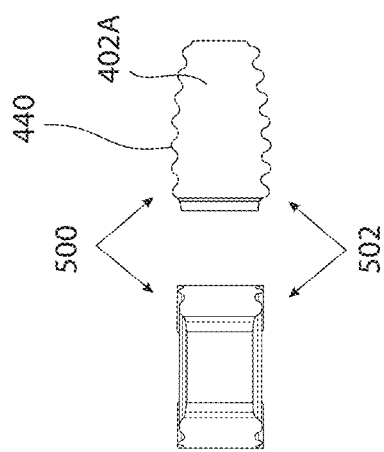

With reference to FIGS. 23, 24, and 25, the implant bodies are shown in their respective orientations during fabricating of the implant bodies by selective laser sintering the particles of the PEKK bed. As shown in FIG. 23, the printed body 402A is positioned so that the skin up surface 500 and the skin down surface 502 contain the gripping members 440.

With reference to FIG. 24, the orientation of the implant body during the selective laser sintering process may be selected to position lower accuracy portions of the implant body at regions of the implant body that are machined off. For example, the printed body 15A may be positioned to have the skin up surface 550 be at the trailing end portion 20 of the printed body 15A and a skin down surface 554 be at the leading end portion 18 of the body 15A. As discussed above, the printed body 15A is machined 530 to form the nose 22, recesses 26, 28, boss 140, and trailing end surface 144. Because the printed body 15A is being machined to form these features at the leading and trailing end portions 18, 20, inaccuracies at the skin up and skin down surfaces 550, 554 are removed by the machining process.

With reference to FIG. 25, the printed body 202A may be positioned so that the trailing end portion 206 of the printed body 202A is at a skin up surface 562 and the leading end portion 208 is at a skin down surface 568. In this manner, any imperfections that occur at the skin up and skin down surfaces 562, 568 are machined off when the recesses 214, 216, boss 290, and nose 210 are machined into the printed body 202A. Additionally, orienting the body 202A so that it prints along a diagonal path, rather than vertical or horizontal, reduces unintended curvature of the body 202A that may result from the selective laser sintering process.

Figure 26:
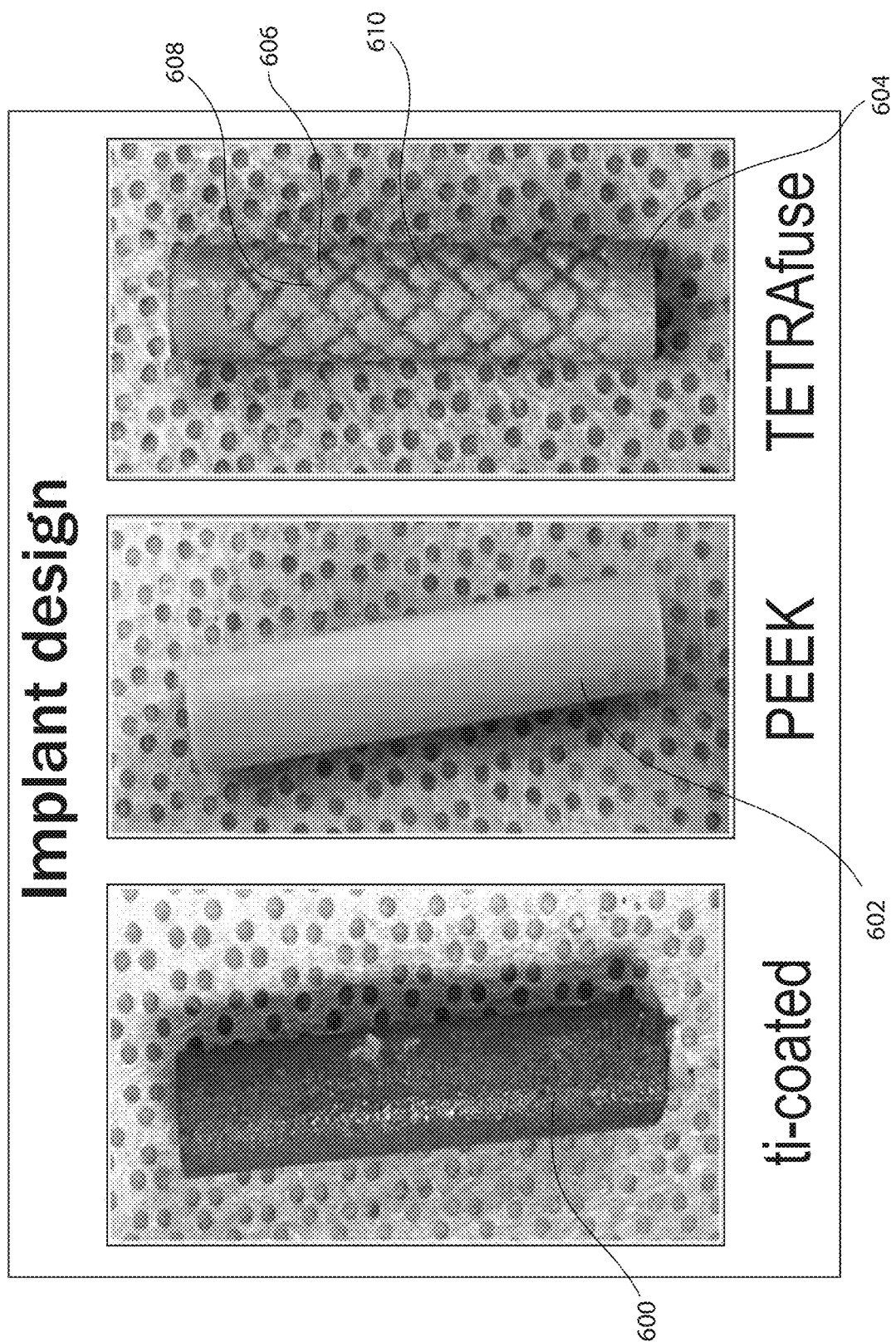
FIG. 26 is an image of different types of pins implanted during a surgical trial including a pin that was formed by selective laser sintering PEKK and includes nubs.

With reference to FIG. 26, testing was performed to provide an understanding of the bone fusion properties provided by the implants 10, 200, 400 discussed above. The testing included an in vivo ovine bone defect study. The study was designed to evaluate biomechanical push-out strength, bone apposition, and bone area of implants including titanium coated PEEK implants 600, uncoated PEEK implants 602, and implants 604 manufactured by selective laser sintering PEKK material. The implants 600 had a roughened outer surface of the titanium material. The implants 604 included diamond-shaped nubs 606 and pathways 608 separating the nubs 606. Because the implants 604 were produced by selective laser sintering PEKK, the implants 604 had a rough exterior surface 610 similar to the rough exterior surfaces of the implants 10, 200, and 400 discussed above.

The implants 600, 602, 604 were cylinder shaped with an outer diameter of 6 mm and a total length of 30 mm. The implants 600, 602, 604 were randomly placed into distal femurs of sheep and allowed to heal for an eight-week time period or a sixteen-week time period. Six implants of each type of implant 600, 602, 604 were implanted for each time period, with three samples per implant type per time period analyzed for push-out testing and three for histological analysis. Histological analysis included fibrosis and immune response assessment using scanning electron microscopy and light microscopy methods. Biomechanical push-out testing was also performed to assess a peak push-out force.

The imaging and histological analyses demonstrated new viable bone surrounding the implants 600, 602, 604. Osteoblast activity suggested the bone to be viable and actively remodeling in the periprosthetic bone region with all three implant types. Bone area in periprosthetic region increased from 26.7 to 40.1% with implant 604, from 14.9 to 35.4% with implant 600, and 40.1 to 47.6% with implant 602. Bone organization and maturation progressed between 8 and 16 week time points.

Periprosthetic regions had similar distribution of trabecular bone and marrow space in all groups but the groups using implant 602 showed higher degree of fibrotic membrane formation around the implants. Bone apposition increased from 3.6% to 34.1% of implant area with implants 604, from 10.5 to 52.3% with implants 600, and decreased from 40% to 16% with implants 602 by 16 weeks. Excellent osseointegration was achieved when implants 604 and 600 were implanted in close approximation to the bone. The implants 602 showed more "spot welding" osseointegration with limited mechanical interlock. No adverse reaction was observed to any implant type.

The histological analysis showed that the topography of the implants 604, which included the nubs 606 and rough exterior surface 610 resulting from selective laser sintering PEKK to fabricate the implants 604, provided larger area for progressive bone growth beyond the eight week time point differently from the implants 600, 602. Bony ingrowth on the implants 604 followed surface topography and filled the micro pores of the implants 604 demonstrating excellent osteoconductive characteristics of the implants 604.

Figure 30:
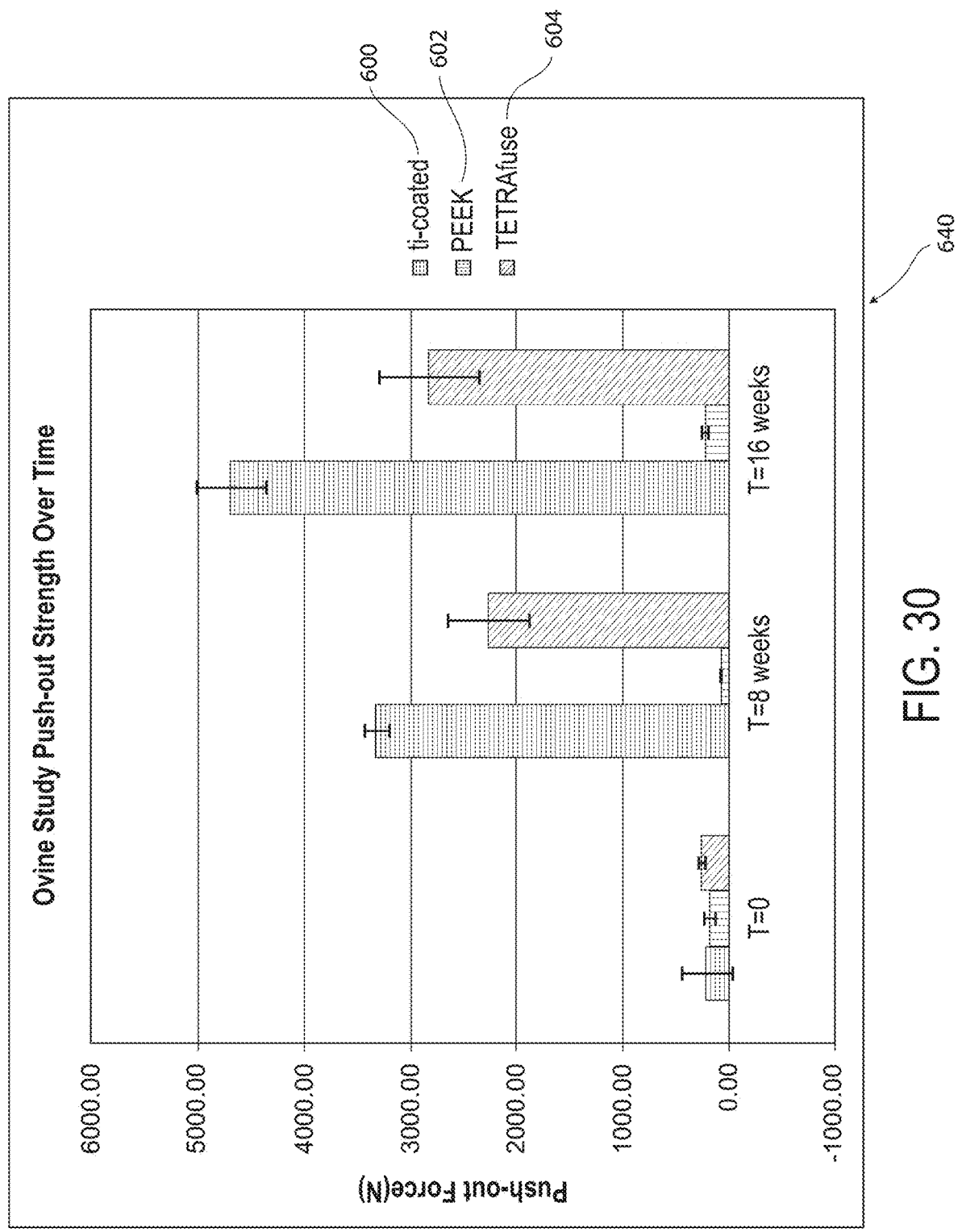
FIG. 30 is a graph showing the push-out resistance of different materials.

Push-out strength significantly increased with the implants 604 and 600 by eight weeks, which is indicative of early and rapid osseointegration. The overall peak force in the group of implants 604 (2819.9 N) was over ten fold higher than the group of implants 602 (230.0N) and about 40% lower than group of implants 600 (4682.9N) by the sixteen-week end point. The results of the pushout testing are provided in a graph 640 of FIG. 30.

Figure 27:
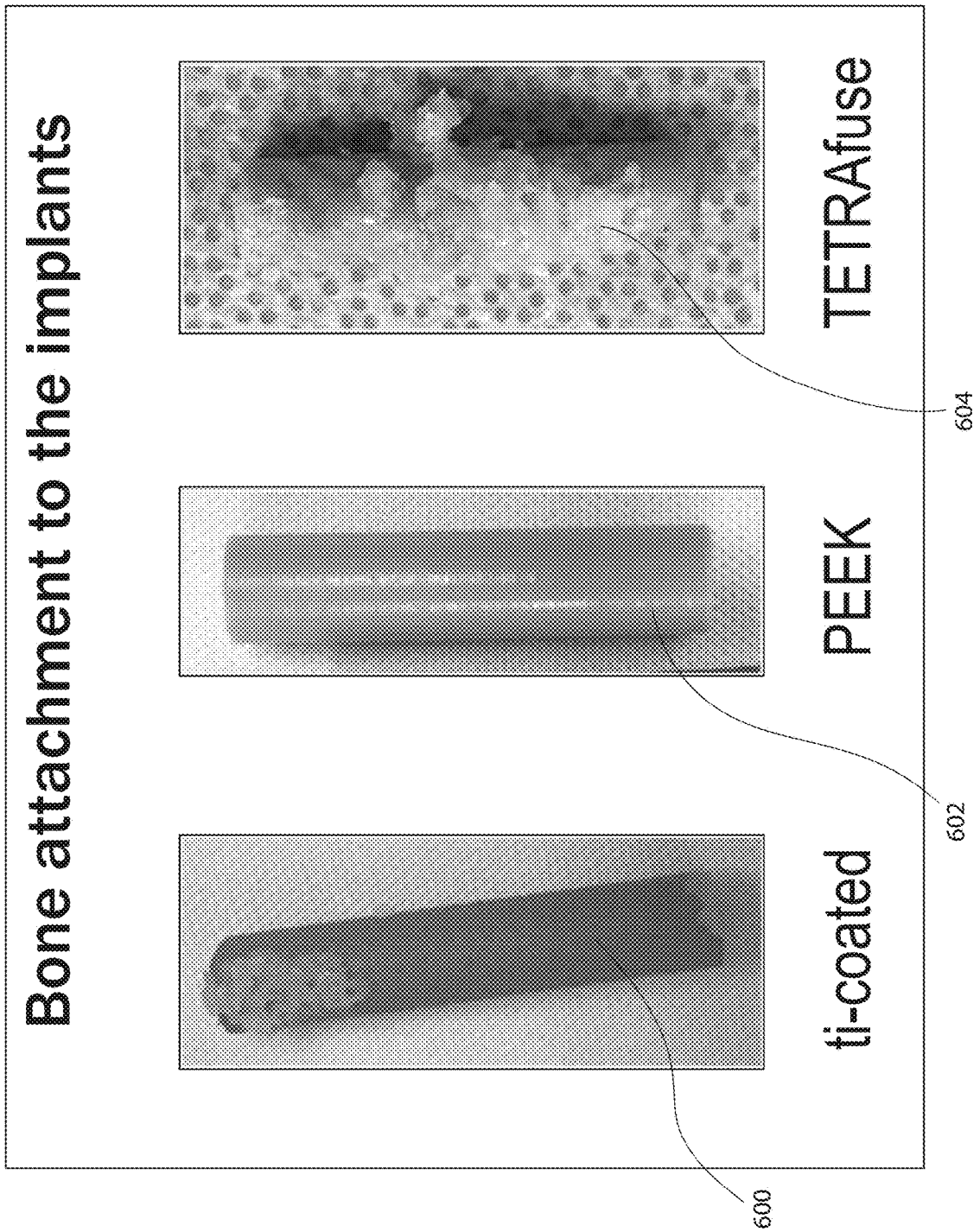
FIG. 27 is an image of the pin implants of FIG. 26 after being removed from the test subjects.

FIG. 27 contains pictures of implants 600, 602, 604 removed during push-out testing at the sixteen week end point. The abundance of cancellous bone attached to the pushed-out implants 604 supported histological observations of significant osseointegration of implants 604 and suggested that the bond between implant and host bone was stronger than the breaking point of native cancellous bone.

On the other hand, the implants 600 had minimal amount of attached bone. The implants 602 had no bone attached.

With reference to FIGS. 28A-C and 29A-C, the study included performing light microscopy after the sixteen week end point for the implants 600, 602, 604. The images of FIGS. 28A-C and 29A-C are cross-sectional views of implants 600, 602, 604 showing bone apposition and ingrowth. The images of FIGS. 29A-29C show marrow spaces 613 and bone 614 around the implants 600, 602, 604. The implant 600 had apposition of bone with minimal fibro-connective tissue ingrowth. The implant 602 had large areas of fibro-connective membrane 611 between the bone and the implant 602 and only regional areas 612 of the bone 614 stitching to the implant 602. The implant 604 had bone ingrowth into the surface structure of the implant 604 that filled the topography of the implant 604 with good bone apposition. The bone ingrowth into the topography of the implant 604 included bone 614 surrounding and engaging with the nubs 606 as well as the bone 614 filling in and engaging pores 618 of the rough exterior surface 610 of the implant 604.

In sum, the implants 604 demonstrated superior osteoconductive properties over the implants 602 with excellent osseointegration into cancellous bone of distal femur similar to implants 600. There was no or minimal fibrosis next to implants 604 and 600 when compared to implants 604. The typography of the implants 604, including the nubs 602 and the rough exterior surface 610, endorsed superior bone ingrowth and integration into cancellous bone which occurred by new bone ingrowth instead of apposition as with the implants 600, 602. The peak push out force significantly increased overtime with implants 604, 600 but not with implants 602. The implants 604 did not show interference with routine imaging methods (such as x-rays) used in clinic, unlike the implant 600 which would be radiopaque due to the titanium coating.

It has also been discovered that an implant fabricated by selective laser sintering PEKK has better antibacterial properties in comparison to a conventional PEEK implant. In particular, bacteria and biofilm formation were studied for these two types of implants. Bacteria cell lines used in this study were *S. epidermidis* and *P. aeruginosa*. Fluorescence confocal microscopy was used to visualize the colonization of bacteria on the samples of interest. The results of this study revealed that both of these two bacteria adhered and grew less on the nano-featured PEKK material substrates as compared to the PEEK material. In particular, the Gram-negative bacteria (*P. aeruginosa*) attached and grew less on the PEKK implant when compared to the Gram-positive bacteria (*S. epidermidis*) on the PEEK implant. More specifically, the PEKK implant had more than a 55% anti-bacterial effect for *P. aeruginosa* and a 40% anti-bacterial effect for *S. epidermidis* as compared to the PEEK implant. It is believed that the nano-rough surface of the PEKK implant changes surface energy which in turn can enhance select protein absorption important for inhibiting bacteria attachment and growth.

Figure 31:
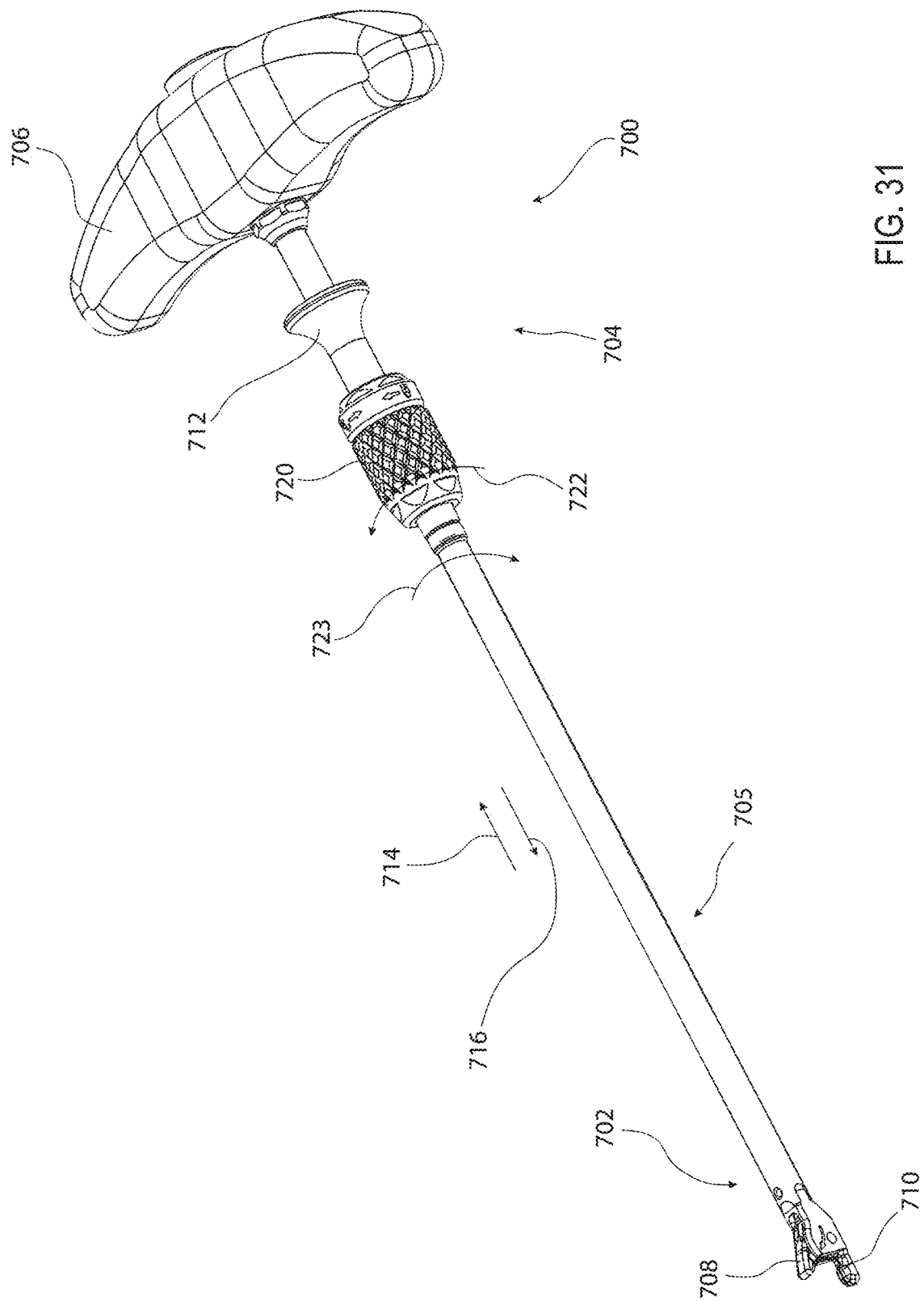
FIG. 31 is a perspective view of an inserter tool for inserting the implant of FIG. 1.

With reference to FIG. 31, an inserter tool 700 is provided for advancing the implant 10 through a surgical passageway and into position between vertebrae. The inserter tool 700 includes a distal end portion 702 for selectively engaging the implant 10 and a proximal end portion 704 having a handle 706. The inserter tool 700 includes a shaft assembly 705 that supports a pivotal clamping arm 708 and a fixed arm 710. The inserter 710 includes an actuator, such as an adjustment knob 712, which may be shifted in direction 714 toward the handle 706 to an open position to pivot the clamping arm 708 to a release position. This allows a user to position the attachment member 24 of the implant 10 between the arms 708, 710. The user then shifts the adjustment knob 712 in direction 716 away from the handle 706 to a closed position to pivot the clamping arm 708 to a clamping position and clamp the attachment member 24 between the arms 708, 710. The inserter tool 700 includes a lock knob 720 having a body 739 that a user may turn in direction 722 to lock the adjustment knob 712 in the closed position. This provides a positive mechanical lock to resist movement of the arm 708 away from the arm 710 and maintain the connection between the distal end portion 702 and the implant 10.

Figure 32:
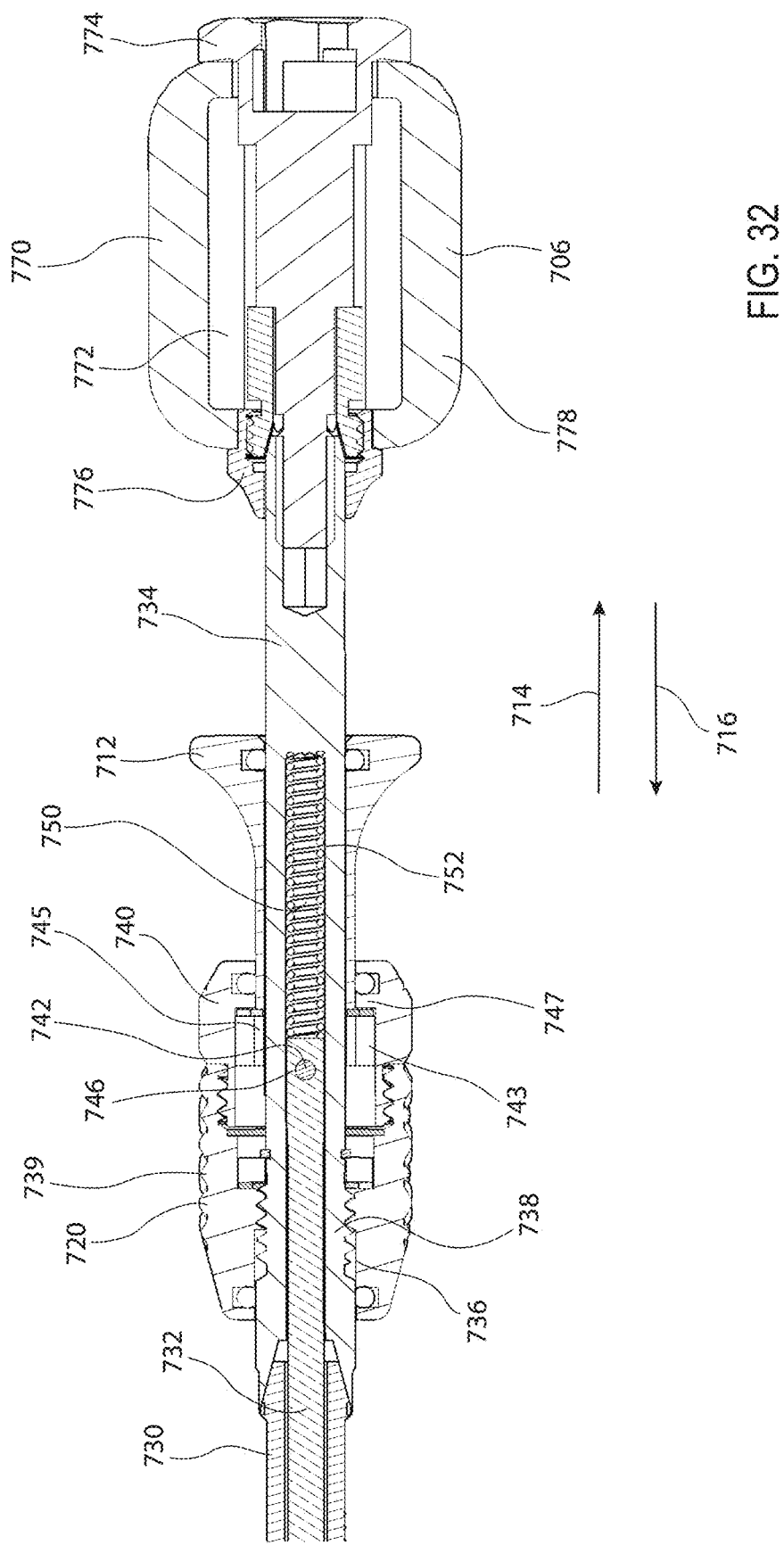
FIG. 32 is a cross-sectional view of a proximal portion the inserter tool of FIG. 31 showing a plunger-shaped adjustment knob that controls connecting of the implant to the inserter tool and a rotatable lock knob for securing the adjustment knob in a locked position.

With reference to FIG. 32, the shaft assembly 705 includes an outer sleeve 730 and an inner shaft 732 within the sleeve 730 that is moveable in directions 714, 716 to pivot the clamping arm 708. The inserter tool 700 includes a rear shaft 734 releasably secured to the outer sleeve 730. The lock knob body 739 has internal threads 736 that engage external threads 738 of the rear shaft 734. The lock knob 720 includes a knob cap 740 connected to the body 739.

The adjustment knob 712 includes a pin 742 that extends through an axially elongated opening of the rear shaft 734 and through a non-axially elongated opening 746 of the inner shaft 732. Thus, when the adjustment knob 712 is shifted in direction 714, the pin 742 transfers the movement of the adjustment knob 712 into movement of the inner shaft 732 in direction 714. The elongated opening of the rear shaft 734 permits the pin 742 to travel within a predetermined range of motion within the rear shaft 734.

The lock nob 720 houses a ring 743 extending around a distal end portion 745 of the adjustment knob 712. The pin 742 has ends that are received in non-axially elongated openings of the ring 743. The pin 742 thereby joins the ring 743, adjustment knob 712, and inner shaft 732 so that the ring 743, adjustment knob 712, and inner shaft 732 shift together in directions 714, 716.

Shifting the knob 712 and inner shaft 732 in direction 714 further compresses a spring 750 received in a cavity 752 of the rear shaft 734. The spring 750 may be partially compressed when the adjustment knob 712 and inner shaft 732 are in the closed position such that the surgeon must further compress the spring 750 in order to shift the adjustment knob 712 and inner shaft 732 to the open positions thereof. The surgeon holds the adjustment knob 712 in the open position to keep the arm 708 pivoted to its release position.

Figure 33:
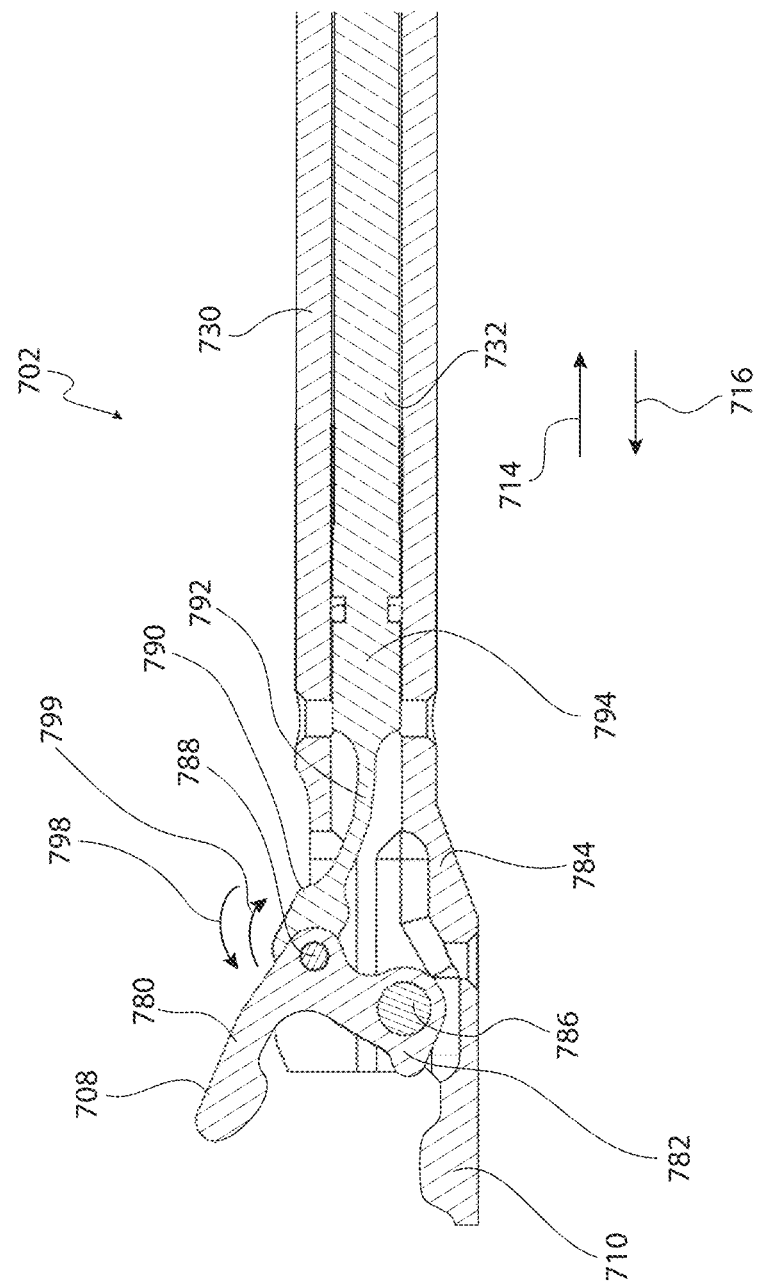
FIG. 33 is a cross-sectional view of a distal portion of the inserter tool of FIG. 31 showing a clamping arm of the inserter tool in an open position.

In one form, the clamping arm 708 is part of an ejecting clamp 780 (see FIG. 33). Once the surgeon positions the implant attachment member 24 between the arms 708, 710, the surgeon releases the adjustment knob 712. The spring 750 urges the inner shaft 732 and adjustment 712 distally in direction 716 which pivots the ejecting clamp 780 in direction 798 and causes the arms 708, 710 to clamp the implant attachment member 24 therebetween.

To lock the ejecting clamp 780 and arm 708 thereof in the clamping position, the surgeon turns the lock knob 720 in direction 722 which causes the lock knob 720 to shift distally in direction 716. The locking knob cap 740 has a flange 747 that abuts the ring 743 and urges the ring 743/pin 742 assembly in direction 716. The surgeon tightens the locking knob 720 in direction 722 so that the engagement between the threads 736, 738 of the lock knob 720 and outer shaft 734 keeps the flange 747 urging the pin 742 in direction 716. In this manner, tightening the lock knob 720 in direction 722 causes the lock knob flange 740 to inhibit the pin 742, inner shaft 732, and adjustment knob 712 from shifting in direction 714 and permitting the arm 708 to pivot to its release position. This locks the arm 708 in the clamping position thereof until the surgeon turns the lock knob 720 in direction 723 to shift the lock knob flange 740 in direction 714, which spaces the flange 747 axially up the rear shaft 734 from the pin 742 and provides space for the pin 742 to shift in direction 714.

With reference to FIG. 32, the handle 706 includes a handle outer portion 770, a handle inner portion 772, and a handle adaptor bolt 774 that connects the handle outer and inner portions 770, 772 to the rear shaft 734. The handle 706 includes a handle lock nut 776 and a spacer 778 for securing the handle inner portion 772 to the rear shaft 734.

With reference to FIG. 33, in one form, the ejecting clamp 780 has a protrusion 782. When the ejecting clamp 780 is pivoted in direction 799, the protrusion 782 contacts the head portion 132 of the implant attachment member 24 and pushes the implant attachment member 24 out from between the arms 708, 710 which assists the surgeon in disconnecting the inserter tool 700 from the implant 10.

The outer sleeve 730 includes a clamp housing 784 and the fixed arm 710 is integrally formed with the clamp housing 784 as shown in FIG. 33. The inserter distal end portion 702 includes a pin 786 that pivotally connects the ejecting clamp 780 to the clamp housing 784. The inserter distal end portion 702 further includes a pin 788 connecting the ejecting clamp 780 to an end portion 790 of the inner shaft 732. The inner shaft 732 includes a flexible portion 792 that may have a reduced cross-sectional thickness as compared to a proximal portion 794 of the inner shaft 732. The flexible portion 792 may bend to compensate for pivoting of the ejecting clamp 780 in direction 799 when the inner shaft 732 is shifted proximally in direction 714. Conversely, the inner shaft 732 shifting in distally direction 716 causes the ejecting clamp 780 to pivot in direction 798. The components of the inserter tool 700 including the shaft 732, sleeve 730, arm 710, clamp 780 may be made of stainless steel such as 17-4 or 465 stainless steel.

Figure 34:
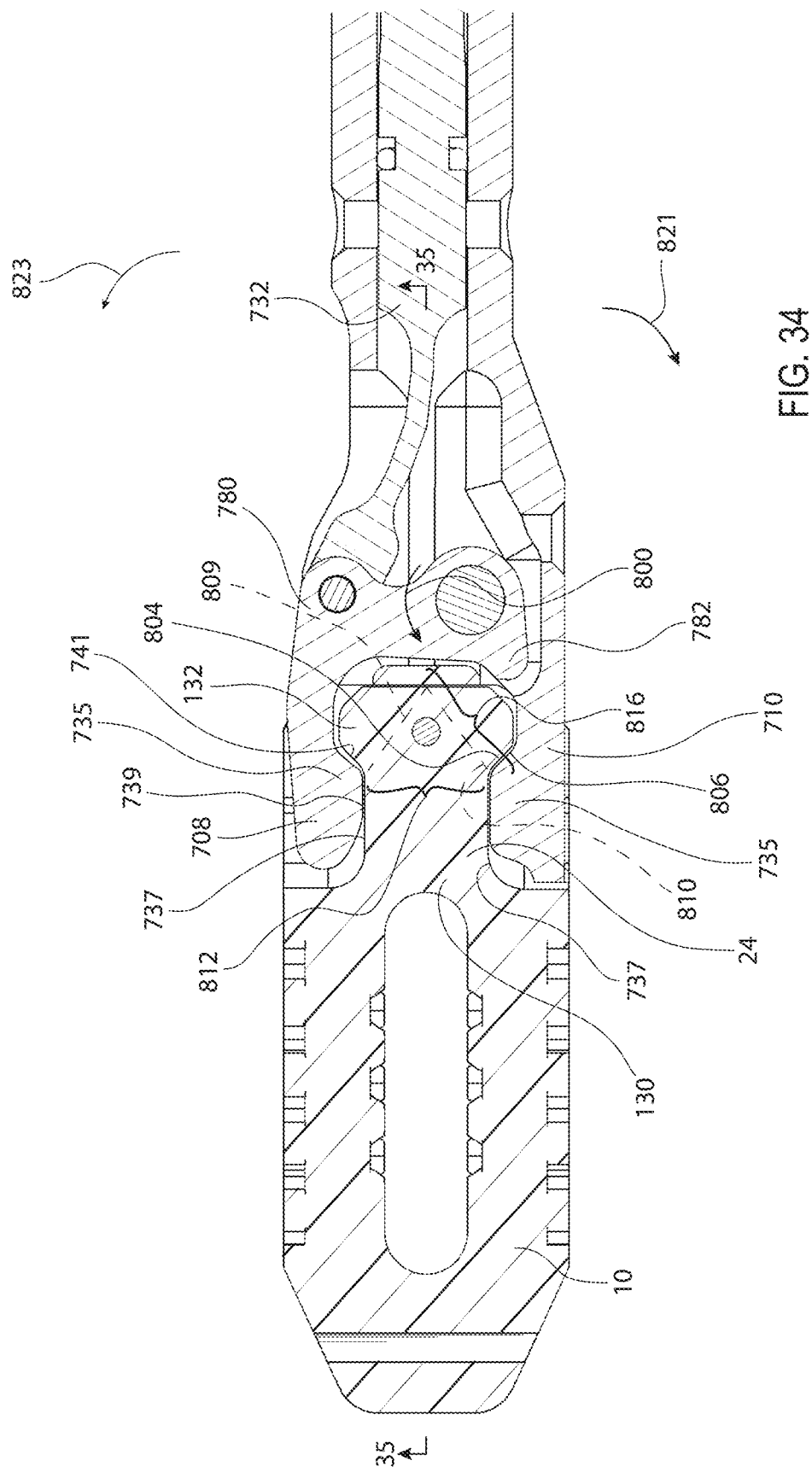
FIG. 34 is a view similar to FIG. 33 showing the clamping arm pivoted to a closed position to clamp an attachment member of the implant between the clamping arm and a fixed arm of the inserter.

With reference to FIG. 34, the arms 708, 710 and implant 10 have mating portions configured to fix the implant 10 to the arms 708, 710 with the arms 710 clamping the attachment member 24 therebetween. The mating portions provide a positive mechanical interlock between the inserter tool 700 and the implant 10 that ensures the implant 10 is correctly and firmly grasped by the inserter tool 700. For example, the arms 708, 710 may have protrusions 735 configured to fit into recesses 737 formed by the neck 130 and head 132 of the attachment member 24. The arms 708, 710 have surfaces 739 that conform to surfaces 741 of the neck 130 and head 132 of the attachment member 24. In this manner, the implant 10 is locked to the inserter distal end portion 702 and generally cannot twist or slide relative to the distal end portion 702.

The attachment member 24 includes tapered surfaces 804 on opposite sides of the head portion 132 of the attachment member 24 and the protrusions 735 of the arms 708, 710 include tapered surfaces 806 that engage the surfaces 804. The surfaces 804, 806 are inclined relative to the longitudinal axis 113 of the implant 10.

In FIG. 34, the inner shaft 732 has been shifted distally in direction 716 to pivot the ejecting clamp 780 to the clamping position thereof. The clamping arm 708 of the ejecting clamp 780 compresses the implant attachment member 24 against the arm 710. This compression urges the surface 804 of the head portion 132 of the attachment member 24 against the surfaces 806 of the arms 708, 710. The surfaces 804, 806 extend transversely to the longitudinal axis 113 of the implant 10. The engagement of the surfaces 804, 806 urges the attachment member 24 in proximal direction 714 and presses the implant trailing end surface 144 against upper and lower portions 820, 822 (see FIG. 35) of the clamp housing 784. In this manner, the material of the attachment member 24 is compressed generally between the protrusions 735 of the arms 708, 710 and the clamp housing upper and lower portions 820, 822.

The engaged surfaces 804, 806 of the implant attachment member 24 and the arms 708, 710 also direct compression of the attachment member 24 due to manipulation of the inserter tool 700 along diagonal paths oblique to the longitudinal axis 26 of the body 15. More specifically, manipulating the inserter tool 700 in lateral direction 821 when the implant 10 has been advanced partially between vertebrae causes compression of the attachment member 24 generally along a transverse path 809. The compression is due at least in part on the arm 710 pushing distally on the attachment member 24 and the arm 708 pulling proximally on the attachment member 24. The transverse path 809 extends from the protrusion 735 of the arm 708 to the trailing end surface 144 of the attachment member. Similarly, manipulating the inserter tool 700 in lateral direction 823 causes compression of the attachment member 24 to act generally along a transverse path 810 between the protrusion 735 of the arm 710 and the trailing end surface 144. If the clamping arms 708, 710 only applied compression in a lateral path across the attachment member 24 when the inserter tool 700 was manipulated in directions 821, 823, such compression would act through a distance 812 of the attachment member 24. As shown in FIG. 34, the distance 816 along transverse path 810 is greater than the distance 812. This means that a greater thickness of material of the attachment member 24 is subjected to the compressive forces due to the engagement between surfaces 804, 806 when the inserter tool is manipulated in directions 821, 823. By increasing the material of the attachment member 24 subject to the compression forces, the attachment member 24 may be strengthened to resist loading during manipulation of the inserter tool 700.

Figure 35:
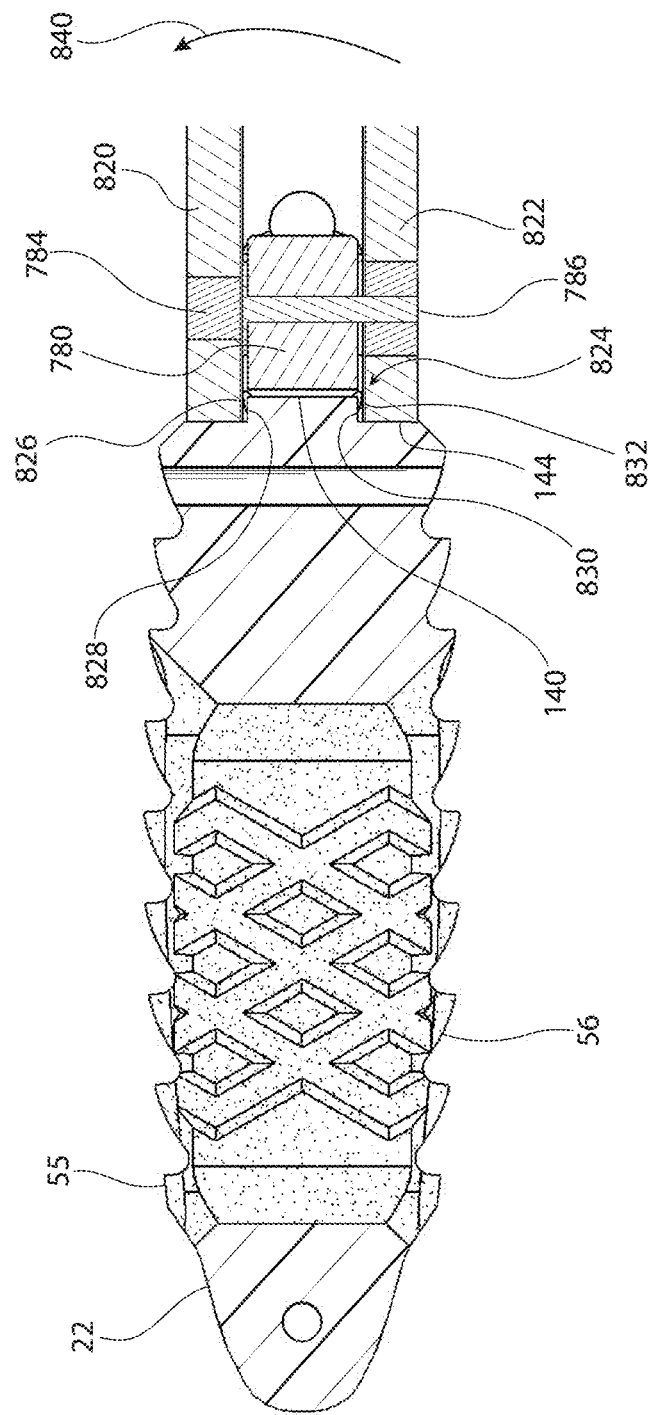
FIG. 35 is a cross-sectional view taken across line 35-35 in FIG. 34 showing the boss of the implant received as a plug in a socket of a distal end of the inserter tool.

With reference to FIG. 35, the upper and lower portions 820, 822 of the clamp housing 784 define a socket 824 for receiving the boss 140 of the implant 10. This creates confronting surfaces 826, 828 and 830, 832 that can transfer loading from the inserter tool 700 to the implant 10. More specifically, if the upper and lower bone engaging portions 55, 56 are positioned partway into a space between vertebrae, and the surgeon lifts up the handle 706 in direction 840, the surfaces 826, 828 and 830, 832 can abut and transfer the loading from the inserter tool shaft 705 to the implant 10. The boss 140 thereby increases the axial length of engagement between the implant 10 and the inserter tool 700 along the longitudinal axis 113 of the implant 10. The loading from the lifting of the shaft 705 in direction 840 is also transferred to the implant 10 by way of the arms 708, 710 pressing against the ceilings 850 and floors 852 (see FIG. 6) of the body 15.

With reference to FIGS. 36, 37, and 38, a method of connecting the implant 10 to the inserter tool 700 is provided. Initially, the lock knob 720 is in an unlocked position and the adjustment knob 712 has been shifted in direction 714 to the proximal, open position as shown in FIG. 36. This causes the clamp arm 708 to pivot to the release position. The implant 10 may be then be advanced in direction 714 to position the attachment member 24 between the arms 708, 710. Next, the adjustment knob 712 is released and the spring 750 urges the inner shaft 732 and adjustment knob 712 distally in direction 716 as shown in FIG. 37. The shifting of the inner shaft 732 in direction 716 causes the arm 708 to pivot in direction 798 and clamp the attachment member 24 between the arms 708, 710. As shown in FIG. 37, the arms 708, 710 are within the envelope of the implant 10 and do not extend laterally outward from the implant 10 which makes the implant 10 easier to advance into the patient.

Next, the lock knob 720 is turned in locking direction 722 as shown in FIG. 38. This shifts the locking knob 720 in direction 716, brings the locking knob flange 720 into contact with the ring 747, and inhibits the pin 742 and inner shaft 732 connected to the ring 747 from shifting in direction 714. This locks the clamping arm 708 in the clamping position and keeps the arms 708, 710 clamping the implant attachment member 24 therebetween.

Figure 39:
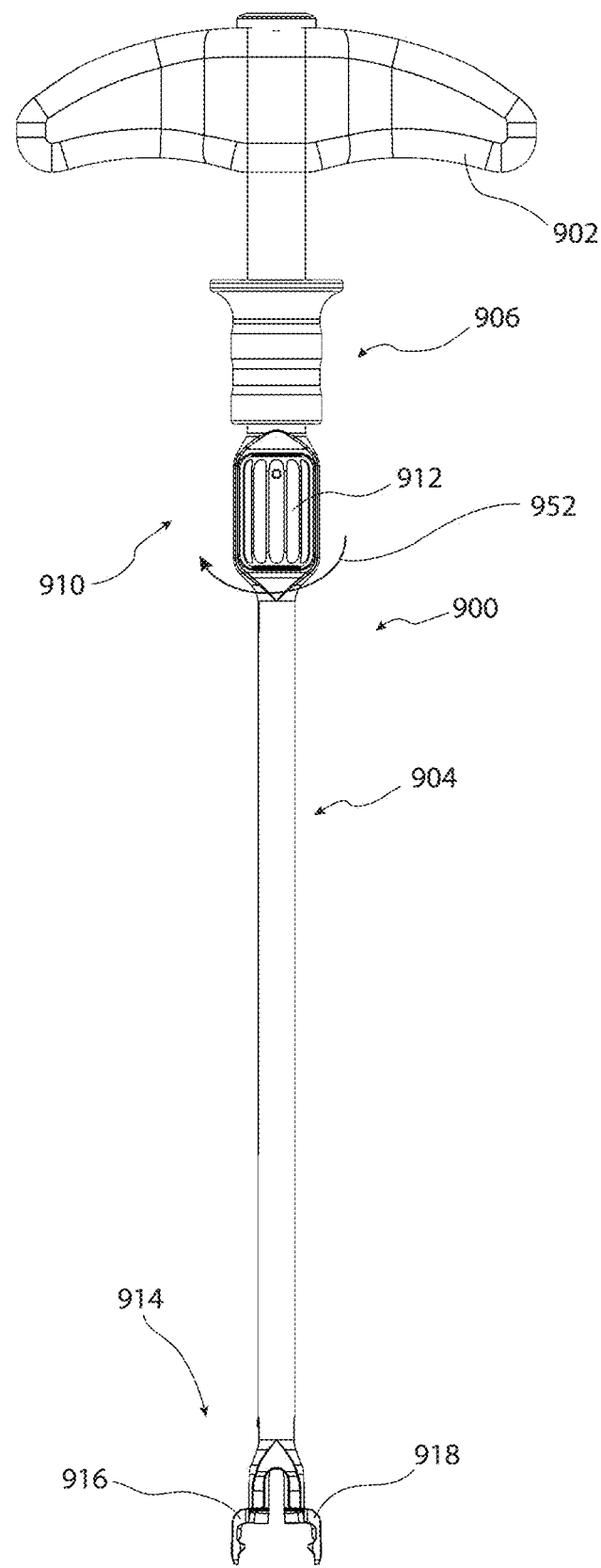
FIG. 39 is an elevational view of an inserter tool for inserting the implant of FIG. 9.

With reference to FIG. 39, an inserter 900 is provided for positioning the implant 200 between vertebrae. The inserter 900 includes a handle assembly 902 and a shaft assembly 904 that is releasably connected to the handle assembly 902 by a quick release mechanism 906 of the handle assembly 902. The shaft assembly 904 includes a proximal end portion 910 having a control knob 912 and a distal end portion 914 having arms 916, 918.

Figure 40:
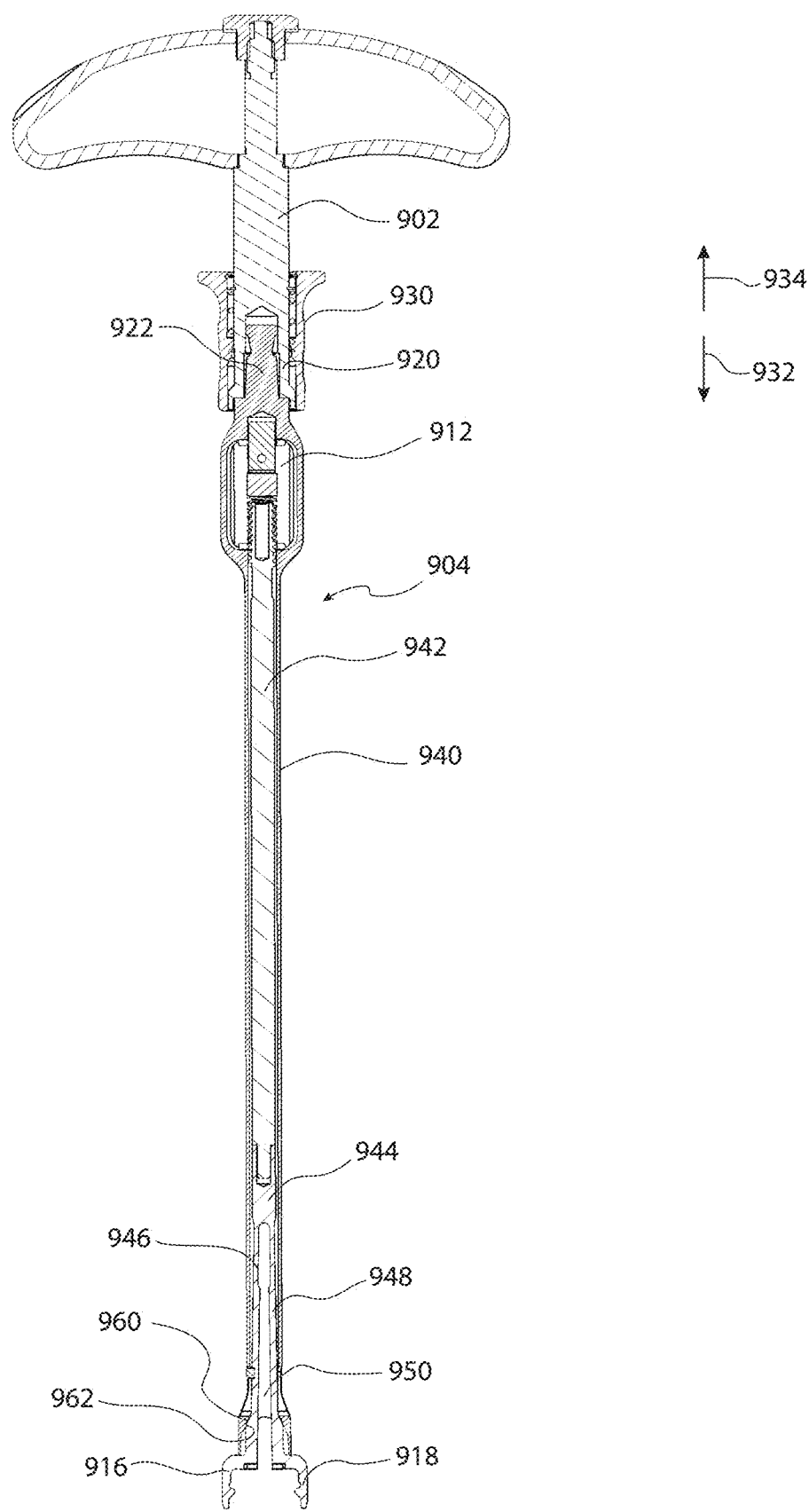
FIG. 40 is a cross-sectional view of the inserter tool of FIG. 39 showing a handle assembly and a shaft assembly of the inserter tool.

With reference to FIG. 40, the handle assembly 902 has a socket 920 that receives a drive member 922 of the shaft assembly 904. The quick release mechanism 906 includes a spring and a sleeve 930 that is urged by the spring in direction 932 to a retention position. When the sleeve 930 is in the retention position, the sleeve 930 shifts detent balls of the quick release mechanism 906 radially inward such that the detent balls resist removal of the drive member 922. To release the shaft assembly 904 from the handle assembly 902, the sleeve 930 is shifted in direction 934 against the bias of the spring which permits the detent balls to shift radially outward and allows the drive member 922 to be withdrawn from the socket 920.

The shaft assembly 904 includes an outer sleeve 940 and an inner shaft 942. The inner shaft 942 is threadedly engaged with the knob 912. The inner shaft 942 is connected to an inserter fork 944 having resilient fork members 946, 948 that are separated from each other by a gap 950. The fork members 946, 948 include the arms 916, 918. To shift the arms 916, 918 toward one another, the knob 912 is turned in direction 952 which draws the inserter shaft 952 proximally in direction 934. The proximal shifting of the inserter shaft 942 in direction 934 causes camming engagement between surfaces 960, 962 of the outer sleeve 940 and fork members 946, 948. This camming engagement shifts the arms 916, 918 toward each other. To release the inserter arms 916, 918 from the implant 200, the knob 912 is turned in a direction opposite direction 952 to shift the inner shaft 942 and inserter fork 944 distally and the resilient properties of the fork members 946, 948 urge the arms 916, 918 apart.

Figure 41:
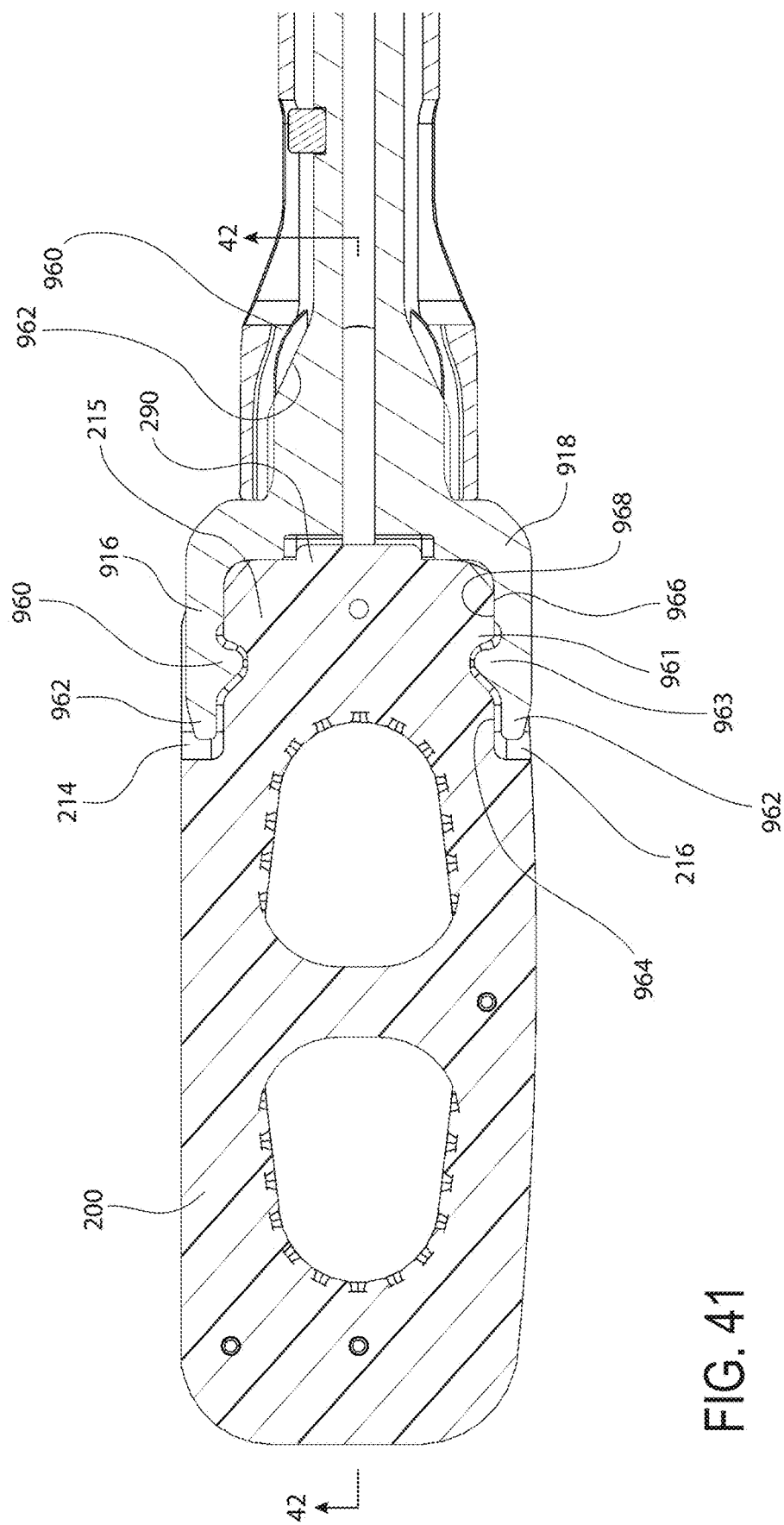
FIG. 41 is a cross-sectional view of a distal end of the shaft assembly of FIG. 40 connected to the implant of FIG. 9.

With reference to FIG. 41, the inserter tool 900 engages the implant 200 in a manner similar to engagement between the inserter tool 700 and the implant 10. The arms 916, 918 have projections 963 that extend into the cavities 300, 302 and mate with walls 961 of the attachment member 215. The arms 916, 918 also include tips 962 that extend along walls 964 of the implant 200. The arms 916, 918 also include inner surfaces 966 that press against and engage surfaces 968 of the attachment member 215.

Figure 42:
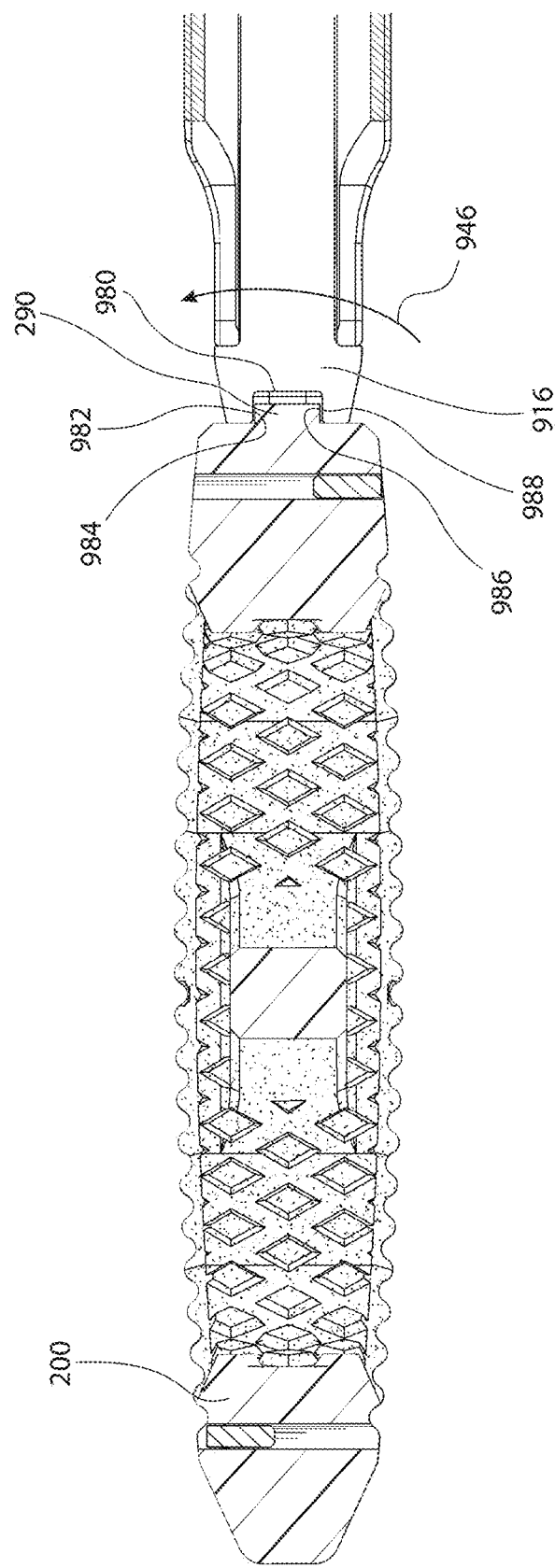
FIG. 42 is a cross-sectional view taken across line 42-42 in FIG. 41 showing a boss of the implant received as a plug in a socket of arms of the shaft assembly of FIG. 40.

With reference to FIG. 42, one difference between the inserter tools 700, 900 is that the inserter 900 has a socket 980 defined by the arms 916, 918 rather than the outer sleeve 940. The socket 980 engages the boss 290 of the implant 200 to improve the strength of the connection between the implant 200 and the inserter 900. The socket 980 includes surfaces 982, 988 that contact surfaces 984, 986 of the boss 290 and increase the longitudinal extent of the engagement between the implant 200 and the inserter 900. The arms 916, 918 also engage the ceilings 990 and floors 992 (see FIG. 12) of the body 202 to transfer loading such as by lifting of the shaft assembly 904 in direction 996 to the implant 200.

Figure 43:
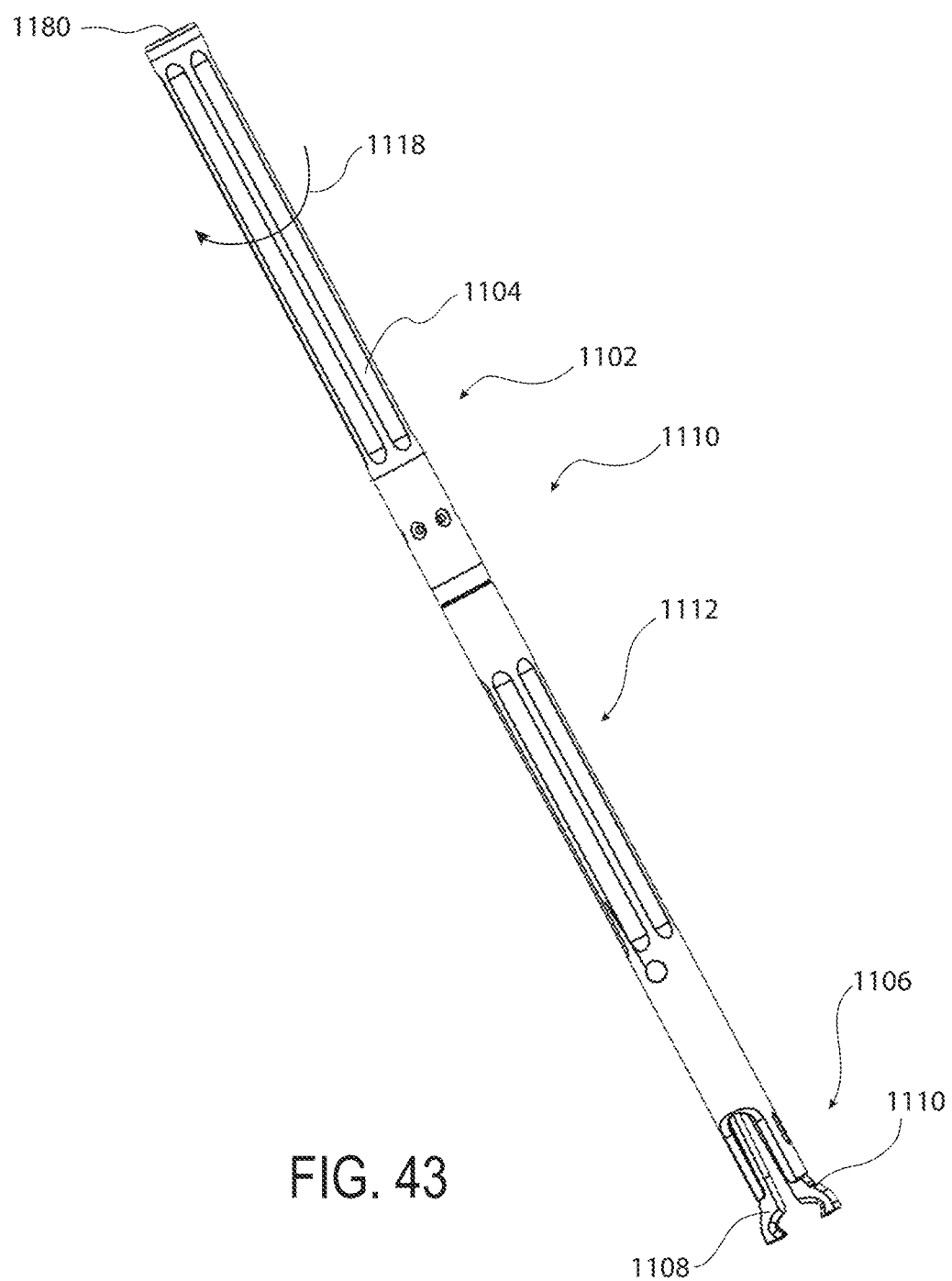
FIG. 43 is a perspective view of an inserter tool for inserting the implant of FIG. 13.
Figure 44:
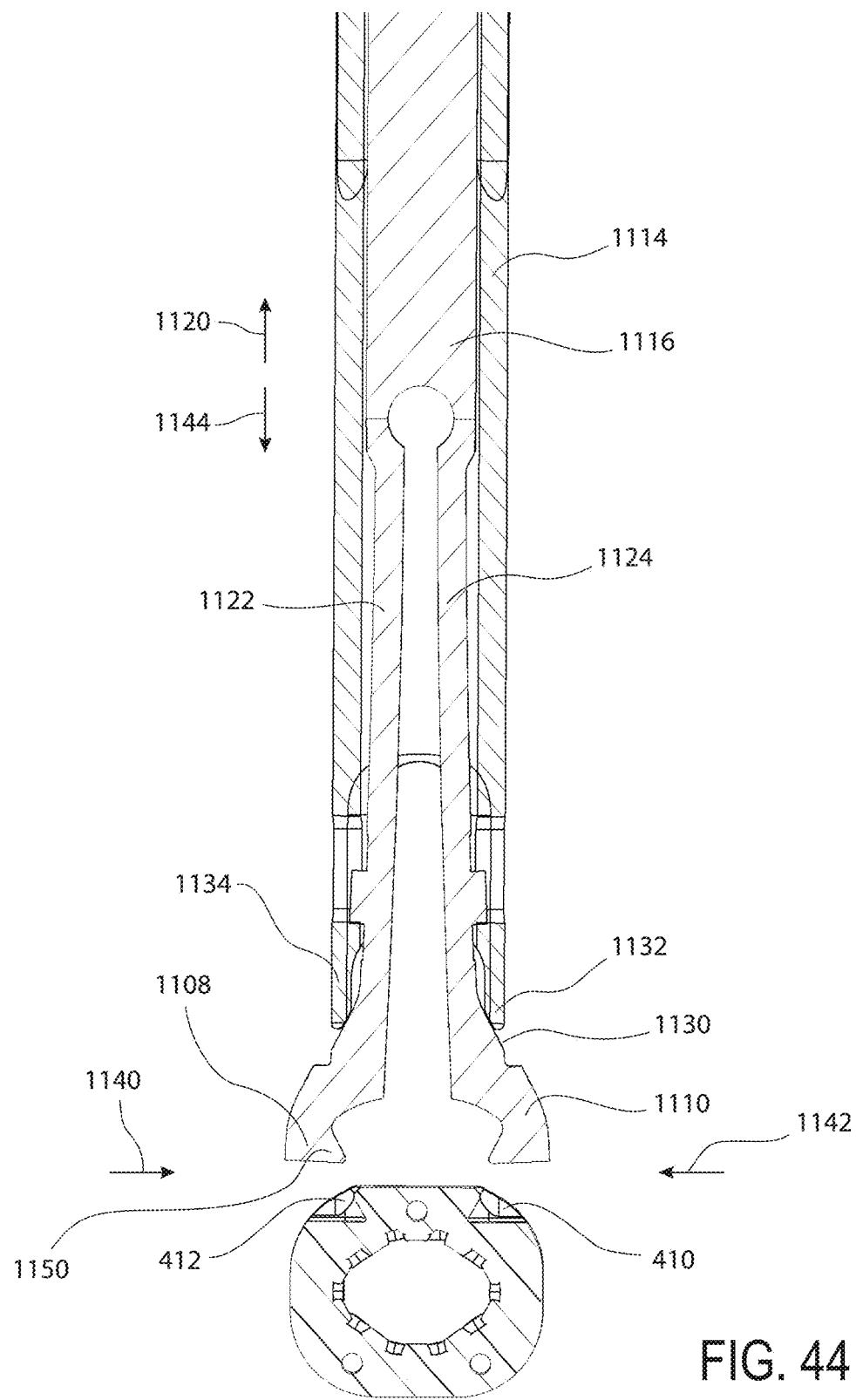
FIG. 44 is a cross-sectional view of a distal end of the inserter of the FIG. 43 and the implant of FIG. 13 showing arms of the inserter in a release position ready to receive the attachment member of the implant.

With reference to FIG. 43, an inserter tool 1100 is provided for positioning the implant 400. The inserter tool 1100 is similar in many respects to the inserter tools 700, 900 discussed above such that differences between the inserters will be discussed. The inserter tool 1100 has a proximal end portion 1102 with a rotatable handle 1104 and a distal end portion 1106 with arms 1108, 1110 for releasably clamping the implant 400. The inserter tool 1100 includes a shaft assembly 1112 having an outer shaft 1114 and an inner shaft 1116. Turning the handle 1104 in direction 1118 draws the inner shaft 1116 proximally in direction 1120. The inner shaft 1116 includes resilient fork members 1122, 1124 that include the arms 1108, 1110. The shifting of the inner shaft 1116 proximally in direction 1120 causes camming engagement between surfaces 1130 of the arms 1108, 110 and a surface 1132 of a distal end portion 1134 of the outer shaft 1114. This urges the arms 1108, 1110 together in directions 1140, 1142 to clamp the dovetail projection 414 of the implant 400 therebetween. Conversely, turning the handle 1104 in a direction opposite to direction 1118 shifts the inner shaft 1116 distally in direction 1144 and the resiliency of the fork members 1122, 1124 causes the arms 1108, 1110 to shift apart.

Figure 45:
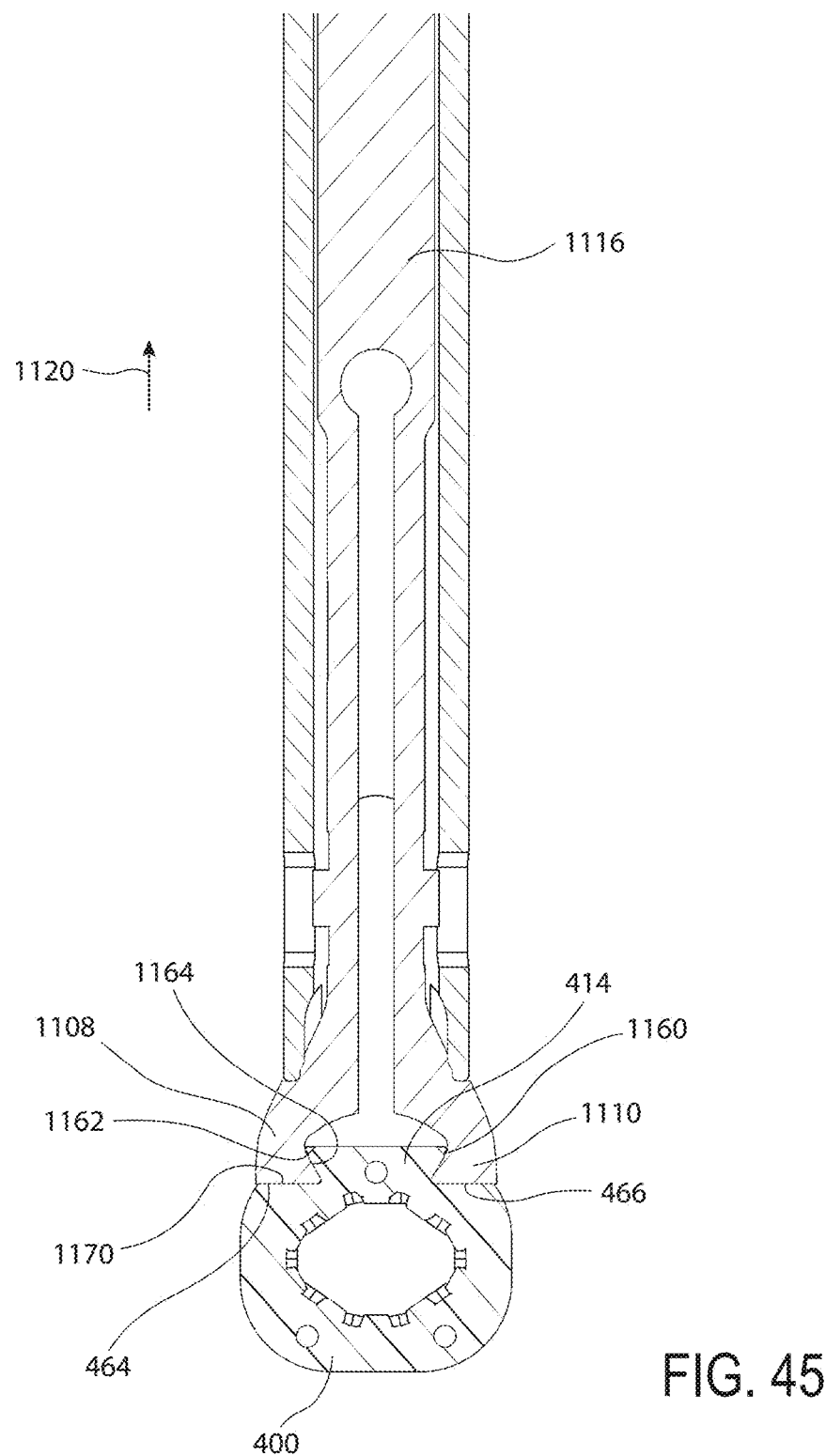
FIG. 45 is a cross-sectional view similar to FIG. 44 showing the arms of the inserter in clamping positions to secure the arms to the implant.

The arms 1110, 1112 include projections 1150 that are positioned in the recesses 410, 412 on opposite sides of the dovetail projection 414. With reference to FIG. 45, turning of the handle 1104 in direction 1118 has urged the inner shaft 1116 proximally in direction 1120 and has engaged the arms 1108, 1110 against the dovetail projection 414. The arms 1108, 1110 are shaped to form a dovetail recess 1160 between the arms 1108, 1110 that has a mating fit with the dovetail projection 414. Further, the projections 1150 have inclined surfaces 1162 that engage inclined surfaces 1164 of the dovetail projection 414 and urge the implant 400 tightly into engagement with the arms 1108, 1110 as the arms 1108, 1110 clamp the dovetail projection 414 therebetween.

The arms 1108, 1110 include flats 1170 that abut the walls 464, 466 of the implant 400. During insertion of the implant 400, the surgeon may tap a hammer on a proximal end 1180 of the handle 1104 and the inserter 1100 transmits these impacts against the implant 400 by way of the engagement between the flats 1170 and the walls 464, 466.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A spinal implant for fusing vertebral bones, the spinal implant comprising:
    a monolithic polymer body for being inserted between bones;
    a through opening of the body for receiving bone growth material;
    a wall of the body extending about the through opening; and
    nubs of the wall extending into the through opening for increasing surface area of the wall available for bone on-growth,
    the nubs having surfaces that include nanostructures comprising peaks and valleys to encourage bone fusion interaction in the through opening of the body;
    wherein the body includes an attachment member outward of the wall;
    opposite lateral sides of the attachment member;
    recesses of the body extending along the opposite lateral sides of the attachment member configured to receive distal end portions of clamping arms of an inserter tool that clamp the opposite lateral sides of the attachment member therebetween;
    a narrower portion of the attachment member adjacent the wall, the narrower portion including a first pair of opposite side surface portions having a first width therebetween across the attachment member; and
    a wider portion of the attachment member spaced from the wall with the narrower portion intermediate the wider portion and the wall along the attachment member, the wider portion including a second pair of opposite side surface portions with a second width therebetween across the attachment member that is larger than the first width, the wider portion configured to be interference with the distal end portions of the clamping arms to inhibit separation of the polymer body from the inserter tool while the clamping arms clamp the attachment member therebetween.

2. The spinal implant of claim 1 wherein the wall includes a plurality of intersecting pathways for the bone growth material that separate the nubs.

3. The spinal implant of claim 1 wherein the wall includes an upper bone engaging portion and a lower bone engaging portion and the wall includes pathways extending from the upper bone engaging portion to the lower bone engaging portion.

4. The spinal implant of claim 1 wherein the wall includes a base surface separating the nubs and each nub has a continuous side surface projecting from the base surface and defining an outer periphery of the nub spaced from the continuous side surface of adjacent nubs.

5. The spinal implant of claim 4 wherein the continuous side surface of each nub includes at least three side wall surface portions connected by edges of the nub.

6. The spinal implant of claim 1 wherein the body is of polyetherketoneketone (PEKK) and the body is fabricated using selective laser sintering.

7. The spinal implant of claim 1 wherein the nubs each have a diamond shape.

8. The spinal implant of claim 1 wherein the wall includes an inner surface that includes the nubs and an outer surface opposite the inner surface and the outer surface includes a plurality of secondary nubs.

9. The spinal implant of claim 8 wherein the nubs and the secondary nubs each have a diamond shape.

10. The spinal implant of claim 1 wherein the wall of the body includes wall portions extending along opposite sides of the through opening, the wall portions each having an upper bone-engaging portion and a lower bone-engaging portion;
    a web of the body interconnecting the wall portions and extending across the through opening;
    uppermost and lowermost portions of the web that are recessed relative to the corresponding upper and lower bone-engaging portions of the wall to avoid contact between the web and the bones during insertion of the implant into a space between the vertebral bones.

11. The spinal implant of claim 10 wherein the wall portions each include nubs above and below the web.

12. The spinal implant of claim 1 wherein the peaks and valleys of the nanostructures have an average peak-to-valley distance of approximately 125-129 nanometers.

13. The spinal implant of claim 1 wherein the peaks of the nanostructures have an average peak-to-peak distance of approximately 265-282 nanometers.

14. The spinal implant of claim 1 wherein the body has an upper bone-engaging portion and a lower bone-engaging portion; and
wherein the nubs each include a pair of upper straight side walls extending transverse to one another and a pair of lower straight side walls extending transverse to one another.

15. The spinal implant of claim 1 wherein the monolithic polymer body is of polyetherketoneketone (PEKK).

16. The spinal implant of claim 1 wherein the monolithic polymer body is of polyetheretherketone (PEEK).

17. An implant for being inserted into an intervertebral space between vertebrae to stabilize the vertebrae, the implant comprising:
a monolithic body of polyetherketoneketone (PEKK), the body being fabricated using selective laser sintering;
a through opening of the body for receiving bone growth material;
an annular wall of the body extending about the through opening and having upper and lower bone engaging portions;
the annular wall being free of through apertures in communication with the through opening;
an attachment member of the body outward of the annular wall;
recesses of the body extending along opposite sides of the attachment member configured to receive distal end portions of clamping arms of an inserter tool that clamp the opposite sides of the attachment member therebetween;
a narrower portion of the attachment member adjacent the annular wall, the narrower portion including a first pair of opposite side surface portions having a first width therebetween across the attachment member; and
a wider portion of the attachment member spaced from the annular wall with the narrower portion intermediate the wider portion and the annular wall along the attachment member, the wider portion including a second pair of opposite side surface portions with a second width therebetween across the attachment member that is larger than the first width, the wider portion of the attachment member configured to be in interference with the distal end portions of the clamping arms to inhibit separation of the body from the inserter tool while the clamping arms clamp the attachment member therebetween.

18. The implant of claim 17 wherein the body has a leading end portion and a trailing end portion and a longitudinal axis extending therebetween and the attachment member includes a boss that increases the axial length of the attachment member for being engaged by the inserter tool.

19. The implant of claim 17 wherein the attachment member includes ramp surfaces at the opposite sides of the attachment member that define at least a portion of the recesses and extend transverse to each other, the ramp surfaces configured so that the body shifts toward the inserter tool as the clamping arms clamp the attachment member.

20. The implant of claim 17 wherein the attachment member includes lateral cavities at the opposite sides of the attachment member that receive projections of the inserter instrument clamping arms.

21. The implant of claim 17 wherein the attachment member is unthreaded.

22. The implant of claim 17 wherein the annular wall has an inner surface extending along the throughbore and an outer surface opposite the inner surface, and the annular wall has a minimum thickness between the inner and outer surfaces thereof of at least approximately 0.06 inches throughout the entire wall.

23. The implant of claim 17 wherein the body includes pores having an average diameter in the range of approximately 500 to approximately 600 micrometers to encourage bone cell on-growth.

24. The implant of claim 17 wherein the inner surface of the annular wall includes nubs projecting into the through opening.

25. The implant of claim 24 wherein the annular wall includes a plurality of intersecting pathways separating the nubs.

26. The implant of claim 17 wherein the body includes openings and marker pins received in the openings, and the marker pins each have a plurality of edges spaced from each other about the marker pin that engage the body and retain the marker pin in the body opening.

27. The implant of claim 17 wherein the body includes a leading end portion and a trailing end portion, the trailing end portion including the attachment member.

28. A spinal implant comprising:
a polymer body fabricated by additive manufacturing a polymer material;
unmachined, irregular surfaces of the body;
nanostructures of the unmachined, irregular surfaces of the body, the nanostructures configured to encourage bone ingrowth into engagement with the unmachined, irregular surfaces of the body; and
a machined attachment portion of the body configured to interface with an inserter tool, the machined attachment portion having a surface roughness that is less rough than a surface roughness of the unmachined, irregular surfaces of the body;
wherein the polymer body includes a through opening of the body for receiving bone growth material and an annular wall extending about the through opening;
wherein the machined attachment portion of the body comprises:
an attachment member;
recesses extending along opposite lateral sides of the attachment member configured to receive distal end portions of clamping arms of an inserter tool that clamp the opposite lateral sides of the attachment member therebetween;
a narrower portion of the attachment member adjacent the annular wall, the narrower portion including a first pair of opposite side surface portions having a first width therebetween across the attachment member; and
a wider portion of the attachment member spaced from the annular wall with the narrower portion intermediate the wider portion and the annular wall along the attachment member, the wider portion including a second pair of opposite side surface portions with a second width therebetween across the attachment member that is larger than the first width, the wider portion configured to be interference with the distal end portions of the clamping arms to inhibit separation of the polymer body from the inserter tool while the clamping arms clamp the attachment member therebetween.

29. The spinal implant of claim 28 wherein the body includes a leading end portion and a trailing end portion and a longitudinal axis extending therebetween, and the machined attachment portion includes an axially extending boss.

30. The spinal implant of claim 28 wherein the body includes a nubs extending into the through opening and the unmachined, irregular surfaces of the body include surfaces of the nubs.

31. The spinal implant of claim 28 wherein the body includes a machined nose portion having a surface roughness that is less rough than the surface roughness of the unmachined body surfaces.

32. The spinal implant of claim 28 wherein the body is made of polyetherketoneketone (PEKK) and is fabricated using selective laser sintering.

33. The spinal implant of claim 28 wherein the annular wall includes nubs extending into the through opening for increasing the surface area of the annular wall available for bone on-growth.

34. The spinal implant of claim 28 wherein the the annular wall including upper and lower bone engaging portions and being free of through apertures in communication with the through opening.

35. The spinal implant of claim 28 wherein the surface roughness of the unmachined, irregular surfaces of the body is in the range of 30-60 roughness average and the surface roughness of the machined attachment portion is in the range of 900-1100 roughness average.

36. The spinal implant of claim 28 wherein the body includes:
    wall portions of the annular wall extending along opposite sides of the through opening, each wall portion including an upper bone engaging portion and a lower bone engaging portion;
    a web of the body interconnecting the wall portions and extending across the through opening; and
    uppermost and lowermost portions of the web that are recessed relative to the corresponding upper and lower bone-engaging portions of the wall to avoid contact between the web and vertebral bones during insertion of the implant into a space between the vertebral bones.

37. The spinal implant of claim 28 wherein the nanostructures include peaks and valleys; and
    wherein the peaks and valleys have an average peak-to-valley distance of approximately 125-129 nanometers.

38. The spinal implant of claim 28 wherein the nanostructures include peaks having an average peak-to-peak distance of approximately 265-282 nanometers.

39. The spinal implant of claim 28 wherein the polymer material includes polyetherketoneketone (PEKK).

\* \* \* \* \*